United States Patent
Pariza et al.

(10) Patent No.: US 11,655,244 B2
(45) Date of Patent: May 23, 2023

(54) CARBAZOLE COMPOUNDS AND METHODS OF USE THEREOF

(71) Applicant: GSNO Therapeutics, Inc, Shelton, WA (US)

(72) Inventors: Richard J. Pariza, Zion, IL (US); Matthews O. Bradley, Kalispell, MT (US)

(73) Assignee: GSNO Therapeutics, Inc., Shelton, WA (US)

( * ) Notice: Subject to any disclaimer, the term of this patent is extended or adjusted under 35 U.S.C. 154(b) by 0 days.

(21) Appl. No.: 16/604,532

(22) PCT Filed: Apr. 11, 2018

(86) PCT No.: PCT/US2018/027170
§ 371 (c)(1),
(2) Date: Oct. 10, 2019

(87) PCT Pub. No.: WO2018/191418
PCT Pub. Date: Oct. 18, 2018

(65) Prior Publication Data
US 2020/0181129 A1    Jun. 11, 2020

Related U.S. Application Data

(60) Provisional application No. 62/565,044, filed on Sep. 28, 2017, provisional application No. 62/484,128, filed on Apr. 11, 2017.

(51) Int. Cl.
| | | |
|---|---|---|
| *C07D 409/14* | (2006.01) | |
| *C07D 209/88* | (2006.01) | |
| *C07D 209/86* | (2006.01) | |
| *C07D 403/06* | (2006.01) | |
| *C07D 403/04* | (2006.01) | |
| *C07D 401/04* | (2006.01) | |
| *C07D 413/12* | (2006.01) | |
| *C07D 417/12* | (2006.01) | |

(52) U.S. Cl.
CPC ......... *C07D 409/14* (2013.01); *C07D 209/86* (2013.01); *C07D 209/88* (2013.01); *C07D 401/04* (2013.01); *C07D 403/04* (2013.01); *C07D 403/06* (2013.01); *C07D 413/12* (2013.01); *C07D 417/12* (2013.01)

(58) Field of Classification Search
None
See application file for complete search history.

(56) References Cited

U.S. PATENT DOCUMENTS

| | | |
|---|---|---|
| 3,956,295 A | 5/1976 | Biere et al. |
| 2003/0229073 A1 | 12/2003 | Booth et al. |
| 2005/0031899 A1 | 2/2005 | Nomura et al. |
| 2009/0047246 A1 | 2/2009 | Beigelman et al. |
| 2009/0170906 A1 | 7/2009 | Gudmundsson et al. |
| 2012/0039804 A1 | 2/2012 | Diaz et al. |

FOREIGN PATENT DOCUMENTS

| | | |
|---|---|---|
| CN | 104672257 | 6/2015 |
| CN | 106543150 | 3/2017 |
| CN | 106543151 | 3/2017 |
| EP | 2119704 | 11/2009 |
| JP | 2016-527206 | 9/2016 |
| WO | WO 2008/096791 | 8/2008 |
| WO | WO 2008/100867 | 8/2008 |
| WO | WO 2012/011642 | 1/2012 |
| WO | WO 2012/170371 | 12/2012 |
| WO | WO 2014/206931 | 12/2014 |
| WO | WO2014206931 | * 12/2014 |

OTHER PUBLICATIONS

Chemical Abstract Registry No. 303756-73-2, indexed in the Registry File on STN CAS Online Nov. 21, 2000.*
Chemical Abstract Registry No. 1373049-14-9, indexed in the Registry File on STN CAS Online May 7, 2012.*
Krahl et al., First total synthesis of the 7-oxygenated carbazole alkaloids clauszoline-K, 3-formyl-7-hydroxycarbazole, clausine M, clausine N and the anti-HIV active siamenol using a highly efficient palladium-catalyzed approach. Organic & Biomolecular Chemistry, 2006, 4, 3215-3219.*
Bautista et al., Palladium-Catalyzed Synthesis of Natural and Unnatural 2-, 5-, and 7-Oxygenated Carbazole Alkaloid from N-Arylcyclohexane Enaminones. Molecules, 2013, 18, 10334-10351.*
Machine-generated English Translation of Foreign Patent Application Publication No. WO2014/206931, published on Dec. 31, 2014.*
CAPLUS prinout of Foreign Patent Application Publication No. CN106543151, published on Mar. 29, 2017.*
Machine-generated English translation of of Foreign Patent Application Publication No. CN 106543151, published on Mar. 29, 2017.*
Saxena et al., S-Nitrosoglutathione reductase (GSNOR) inhibitor as an immune modulator in experimental autoimmune encephalomyelitis. Free Radical Biology & Medicine, 2018, 121, 57-68.*
Schafer, S., Kolkhof, P. Failure is an option: learning from unsuccessful proof-of-concept trials. Drug Discovery Today. Nov. 2008, 13, 913-916.*
Horig, H., Pullman, W. From bench to clinic and back: Perspective on the 1st IQPC Translational Research conference. Journal of Translational Medicine. Dec. 2004, 2, 44.*
Extended European Search Report and Opinion dated Oct. 28, 2020 for EP Application No. 18783804.0. 10 pages.

(Continued)

*Primary Examiner* — Po-Chih Chen
(74) *Attorney, Agent, or Firm* — Sheppard Mullin Richter & Hampton LLP

(57) ABSTRACT

Described herein are compounds, pharmaceutical compositions and methods that are useful as S-nitrosoglutathione reductase (GSNOR) inhibitors.

14 Claims, 14 Drawing Sheets

(56) References Cited

OTHER PUBLICATIONS

Favia, et al. Identification and characterization of carprofen as a multitarget fatty acid amide hydrolase/cyclooxygenase inhibitor. J Med Chem. Oct. 25, 2012;55(20):8807-26.

International Search Report and Written Opinion dated Jul. 23, 2018 for PCT/US2018/027170. 13 pages.

Sun, et al. Structure-activity relationship of pyrrole based S-nitrosoglutathione reductase inhibitors: Carboxamide modification. Bioorganic & Medicinal Chemistry Letters. Mar. 15, 2012; 22(6):2338-2342.

Zhang, et al. Syntheses, structures, luminescent and gas adsorption properties of five new interpenetrated, 2D and 3D metal-organic frameworks based on a semi-rigid bis(imidazole)-carbazole ligand. Polyhedron. Dec. 14, 2015; 102:401-409.

Zhou, et al. A new ligand for the formation of a 3D structure by C—H•••O, O—H•••O hydrogen-bonds and π-π interactions. Journal of Molecular Structure. Dec. 15, 2008; 892(1-3) 316-319.

\* cited by examiner

CARBAZOLE COMPOUNDS AND METHODS OF USE THEREOF

CROSS REFERENCE TO RELATED APPLICATIONS

This application is the U.S. national stage application of International Application No. PCT/US2018/027170, filed Apr. 11, 2018, which claims the benefit under 35 U.S.C. § 119(e) to U.S. Provisional Application No. 62/484,128, filed Apr. 11, 2017, and U.S. Provisional Application No. 62/565,044, filed Sep. 28, 2017, the entireties of which are incorporated herein by reference.

FIELD

This disclosure relates to compounds, pharmaceutical compositions and methods that are useful as S-nitrosoglutathione reductase (GSNOR) inhibitors. In some embodiments, this disclosure provides methods for treating various diseases or disorders involving S-nitrosoglutathione reductase (GSNOR). These include diseases mediated at least in part by the cytokine Interleukin-6 (IL-6), Interleukin-17 (IL-17), or Interleukin-23 (IL-23). In one embodiment, the compounds and compositions of this disclosure are generally applicable toward the treatment of disorders including inhibition of tissue and/or organ inflammation due to IL-6, IL-17, or IL-23 over expression. In one embodiment, the compounds and compositions of this disclosure are generally applicable toward the treatment of disorders including inhibition of tissue and/or organ inflammation due to IL-6 over expression.

BACKGROUND

The discovery that nitric oxide (NO) has important physiological roles in many different cells and organs led to the Nobel Prize in 1998. Research efforts have tried to utilize the nitric oxide pathway for disease treatment. For example, it was believed that the synthesis of nitric oxide donors or nitric oxide releasing compounds would provide therapeutic results. Most of those research efforts failed, in part, because nitric oxide has a short half-life in vivo measured in seconds. Further, intracellular delivery of effective doses to target tissues has been generally insufficient for therapeutic effects, except in limited applications, such as in premature infants.

However, it has been suggested that the enzyme GSNOR might be used to produce benefits similar to nitric oxide. GSNOR breaks down s-nitroso-glutathione (GSNO). GSNO is a chemical conjugate of glutathione and nitric oxide and is the cellular stable, storage form of nitric oxide. This enzyme enables the formation of nitrosylated proteins albeit by a different chemical mechanism than that used by nitric oxide itself. Inhibition of GSNOR thereby increases intracellular GSNO concentrations and its bioavailability. This results in increased nitrosylation of the cysteines on proteins that regulate signal transduction pathways important to diseases, including diseases mediated at least in part by excessive amount of IL-6, IL-17, or IL-23. Accordingly, inhibition of GSNOR correlates to reduced expression of IL-6, IL-17, or IL-23 in vivo. In turn, IL-6, IL-17, or IL-23 over-expression has been implicated in a wide variety of diseases.

Accordingly, inhibition of GSNOR will be efficacious in those conditions and diseases which are mediated by IL-6, IL-17, or IL-23. As such, there is a continuing need for inhibitors of GSNOR and for methods of treating IL-6, IL-17, or IL-23 related diseases or disorders which can be affected by GSNOR inhibition.

SUMMARY

This disclosure is directed, in part, to aromatic nitrogen-containing compounds which inhibit GSNOR thereby increasing the endogenous pool of GSNO. This increase in the amount of endogenous GSNO affects a chain of cellular effects that elicit therapeutic benefits including the reduction of IL-6, IL-17, or IL-23 production. Aromatic nitrogen-containing compounds of this disclosure are broadly effective in treating conditions arising from IL-6 over-expression. In some embodiments, compounds of this disclosure may be useful in treating conditions arising from IL-6, IL-17, or IL-23 overexpression.

Certain embodiments of this disclosure is directed toward using these aromatic nitrogen-containing compounds to treat conditions in a subject which include those mediated at least in part by over-expression of IL-6. Accordingly, in one embodiment, this disclosure is directed toward methods of alleviating or ameliorating a condition or disorder, mediated at least in part by GSNOR, including conditions arising from over-expression of IL-6.

Certain embodiments of this disclosure is directed toward using these aromatic nitrogen-containing compounds to treat conditions in a subject which include those mediated at least in part by over-expression of IL-17. Accordingly, in one embodiment, this disclosure is directed toward methods of alleviating or ameliorating a condition or disorder, mediated at least in part by GSNOR, including conditions arising from over-expression of IL-17.

Certain embodiments of this disclosure is directed toward using these aromatic nitrogen-containing compounds to treat conditions in a subject which include those mediated at least in part by over-expression of IL-23. Accordingly, in one embodiment, this disclosure is directed toward methods of alleviating or ameliorating a condition or disorder, mediated at least in part by GSNOR, including conditions arising from over-expression of IL-23.

In some embodiments, the methods, compounds, and/or compositions of this disclosure are used prophylactically.

This disclosure is also directed to compounds, pharmaceutical compositions, and methods of use to inhibit GSNOR. This disclosure is also generally applicable toward the treatment of diseases and disorders which can be treated by inhibition of GSNOR.

In particular, in one embodiment, provided is a compound of Formula I:

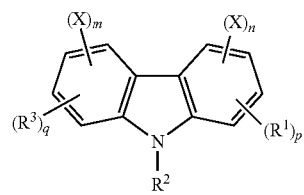

wherein:
m and n independently are 0 or 1;
p and q are 1;
each X is independently F or $CF_3$;
$R^2$ is selected from the group consisting of hydrogen, alkyl, substituted alkyl, acyl, acylamino, aryl, substituted aryl, heteroaryl, and substituted heteroaryl;

R¹ is selected from the group consisting of carboxyl, carboxyl ester, -aryl-carboxyl, -alkyl-carboxyl, and -alkyl-carboxyl ester; and R³ is selected from the group consisting of alkyl, substituted alkyl, amino, substituted amino, alkoxy, substituted alkoxy, heterocycloalkyl, substituted heterocycloalkyl, heterocycloalkyloxy, substituted heterocycloalkyloxy, heterocycloalkylthio, substituted heterocycloalkylthio, heteroaryl, substituted heteroaryl, heteroaryloxy, substituted heteroaryloxy, heteroarylthio, and substituted heteroarylthio;

or a tautomer, solvate, or a pharmaceutically acceptable salt thereof.

In a related embodiment, pharmaceutical compositions are provided that include an effective amount of one or more compounds of Formula I and a pharmaceutically acceptable excipient.

In one embodiment, provided is a method for inhibiting GSNOR which method comprises contacting cells (including neurons/microglia/invading macrophages) with an effective amount of one or more compounds of Formula I above.

In another embodiment, provided is a method for treating a disease or disorder mediated at least in part by GSNOR, where the method involves administering to a subject an effective amount of one or more compounds of Formula I or a pharmaceutical composition comprising a pharmaceutically acceptable excipient and an effective amount of one or more compounds of Formula I.

These and other embodiments are described in further detail herein.

DETAILED DESCRIPTION

Figure 1:
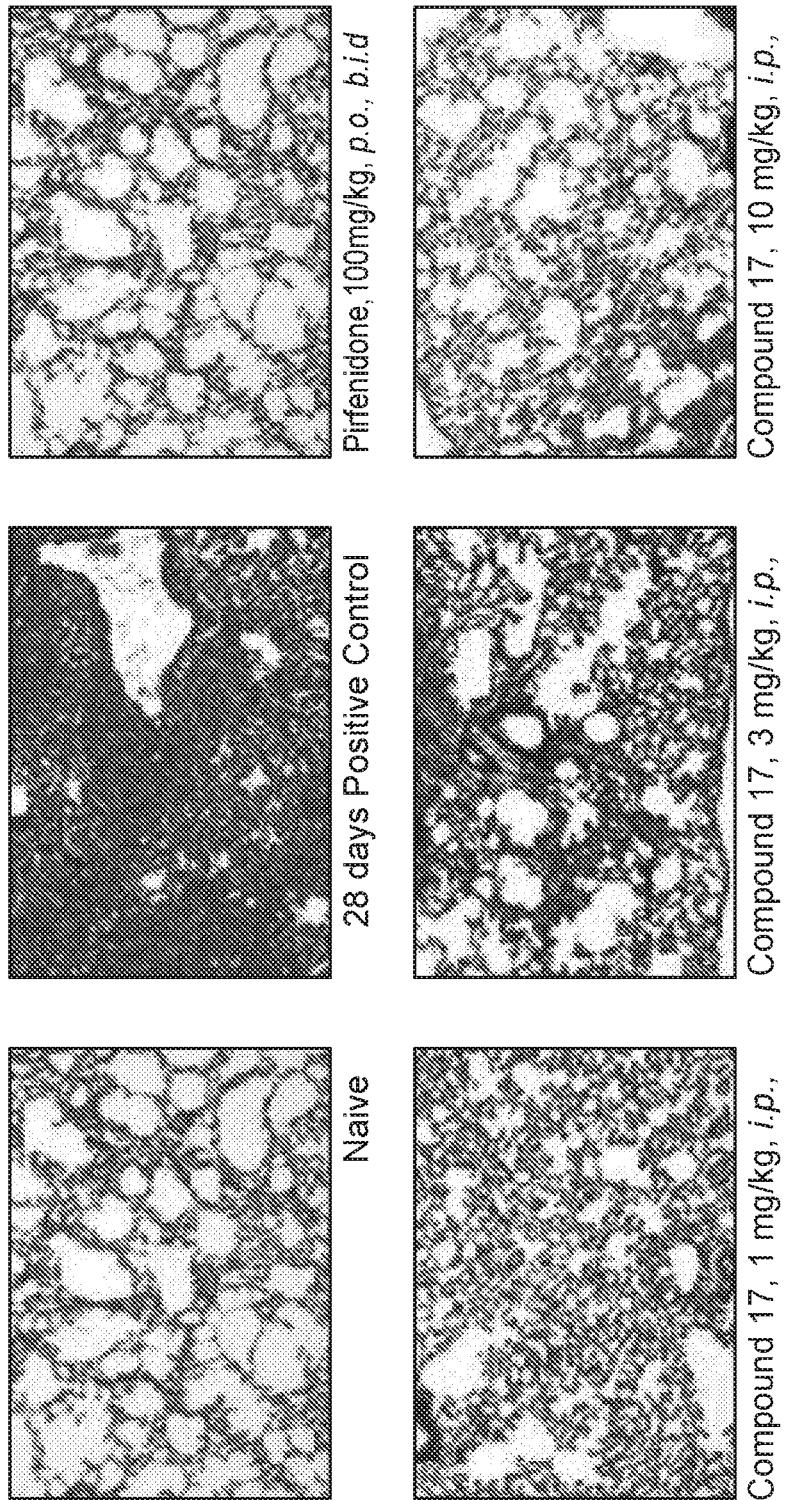
FIG. 1 illustrates the Masson Trichrome Staining in Bleomycin-induced Mouse Idiopathic Pulmonary Fibrosis (IPF) model.

Throughout this application, the text refers to various embodiments of the present compounds, compositions, and methods. The various embodiments described are meant to provide a variety of illustrative examples and should not be construed as descriptions of alternative species. Rather, it should be noted that the descriptions of various embodiments provided herein may be of overlapping scope. The embodiments discussed herein are merely illustrative and are not meant to limit the scope of this disclosure.

1. Definitions

As used herein, the following definitions shall apply unless otherwise indicated. Further, if any term or symbol used herein is not defined as set forth below, it shall have its ordinary meaning in the art.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of this disclosure. In some embodiments, isotopes that can be incorporated into compounds of the disclosure include isotopes of hydrogen, carbon, nitrogen, oxygen, phosphorous, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl and $^{125}$I. Various isotopically labeled compounds of the present disclosure may be, for example, those into which radioactive isotopes such as $^3$H, $^{13}$C and $^{14}$C are incorporated. Procedures for inserting such labels into the compounds of this disclosure will be readily apparent to those skilled in the art based on the disclosure herein. "Deuterated analog" as used herein refers to the resulting analog wherein at least one hydrogen of a compound is replaced with a deuterium. "Deuterated analogs" of compounds described herein refer to compounds in which one or more hydrogens is/are replaced by deuterium, such as a hydrogen on a carbon atom.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl (CH$_3$—), ethyl (CH$_3$CH$_2$—), n-propyl (CH$_3$CH$_2$CH$_2$—), isopropyl ((CH$_3$)$_2$CH—), n-butyl (CH$_3$CH$_2$CH$_2$CH$_2$—), isobutyl ((CH$_3$)$_2$CHCH$_2$—), sec-butyl ((CH$_3$)(CH$_3$CH$_2$)CH—), t-butyl ((CH$_3$)$_3$C—), n-pentyl (CH$_3$CH$_2$CH$_2$CH$_2$CH$_2$—), and neopentyl ((CH$_3$)$_3$CCH$_2$—). C$_x$ alkyl refers to an alkyl group having x number of carbon atoms.

"Substituted alkyl" refers to an alkyl group having from 1 to 5, preferably 1 to 3, or more preferably 1 to 2 substituents selected from the group consisting of alkoxy, substituted alkoxy, acyl, acylamino, amino, substituted amino, aryl, substituted aryl, aryloxy, substituted aryloxy, carboxyl, carboxyl ester, cyano, cycloalkyl, substituted cycloalkyl, cycloalkyloxy, substituted cycloalkyloxy, halo, hydroxy, heteroaryl, substituted heteroaryl, heteroaryloxy, substituted heteroaryloxy, heterocyclic, substituted heterocyclic, heterocyclyloxy, substituted heterocyclyloxy, and nitro, wherein said substituents are defined herein.

In some embodiments the substituted alkyl groups include halogenated alkyl groups and particularly halogenated methyl groups such as trifluoromethyl, difluromethyl, fluoromethyl and the like. In this instance, the term is referred to as "haloalkyl." Haloalkyl refers to an unbranched or branched alkyl group as defined above, wherein one or more hydrogen atoms (for example, 1 to 5 hydrogen atoms or 1 to 3 hydrogen atoms) are replaced by a halogen.

In some embodiments, the substituted alkyl group is alkyl substituted with —C(O)—NH$_2$.

"Alkenyl" refers to an alkyl group containing at least one carbon-carbon double bond and having from 2 to 20 carbon atoms (i.e., C$_{2-20}$ alkenyl), 2 to 8 carbon atoms (i.e., C$_{2-8}$ alkenyl), 2 to 6 carbon atoms (i.e., C$_{2-6}$ alkenyl), or 2 to 4 carbon atoms (i.e., C$_{2-4}$ alkenyl). Examples of alkenyl groups include ethenyl, propenyl, butadienyl (including 1,2-butadienyl and 1,3-butadienyl).

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Substituted alkoxy" refers to the group —O-(substituted alkyl) wherein substituted alkyl is defined herein. Preferred substituted alkyl groups in —O-(substituted alkyl) include halogenated alkyl groups and particularly halogenated methyl groups such as trifluoromethyl, difluromethyl, fluoromethyl and the like. In one embodiment, substituted alkoxy is -oxy-alkylene-carboxyl or an oxy-alkylene carboxyl ester. Such substituted alkoxy groups are represented by the formula —O-alkylene-COOH and —O-alkylene-carboxyl ester.

"Acyl" refers to the groups alkyl-C(O)—, substituted alkyl-C(O)—, cycloalkyl-C(O)—, substituted cycloalkyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkoxy, substituted alkoxy, cycloalkyl, substituted cycloalkyl, aryl, substituted aryl, heteroaryl, substituted heteroaryl, heterocyclic and substituted heterocyclic are as defined herein. Acyl includes the "acetyl" group CH$_3$C(O)—. In some embodiments, acyl includes

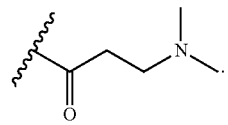 [SMILES: *C(=O)CCN(C)C]

"Acyloxy" refers to the group —O-acyl wherein acyl is defined herein.

"Acylamino" refers to the group -acyl-amino, wherein acyl is defined herein and amino is defined herein.

"Amino" refers to the group —NH$_2$.

"Substituted amino" refers to the group —NR$^{31}$R$^{32}$ where R$^{31}$ and R$^{32}$ are independently selected from the group consisting of hydrogen, alkyl, substituted alkyl, aryl, substituted aryl, cycloalkyl, substituted cycloalkyl, heteroaryl, substituted heteroaryl, heterocyclic, substituted heterocyclic, and wherein R$^{31}$ and R$^{32}$ are optionally joined, together with the nitrogen bound thereto to form a heterocyclic or substituted heterocyclic group, provided that R$^{31}$ and R$^{32}$ are both not hydrogen, and wherein alkyl, substituted alkyl, cycloalkyl, substituted cycloalkyl, aryl, substituted aryl, heteroaryl, substituted heteroaryl, heterocyclic, and substituted heterocyclic are as defined herein. When R$^{31}$ is hydrogen and R$^{32}$ is alkyl, the substituted amino group is sometimes referred to herein as alkylamino. When R$^{31}$ and R$^{32}$ are alkyl, the substituted amino group is sometimes referred to herein as dialkylamino. When referring to a monosubstituted amino, it is meant that either R$^{31}$ or R$^{32}$ is hydrogen but not both. When referring to a disubstituted amino, it is meant that neither R$^{31}$ nor R$^{32}$ are hydrogen.

"Aryl" or "Ar" refers to a monovalent aromatic carbocyclic group of from 6 to 14 carbon atoms having a single ring (e.g., phenyl (Ph)) or multiple condensed rings (e.g., naphthyl or anthryl) which condensed rings may or may not be aromatic (e.g., 2-benzoxazolinone, 2H-1,4-benzoxazin-3 (4H)-one-7-yl, and the like) provided that the point of attachment is at an aromatic carbon atom. Preferred aryl groups include phenyl and naphthyl.

"Substituted aryl" refers to aryl groups which are substituted with 1 to 5, preferably 1 to 3, or more preferably 1 to 2 substituents selected from the group consisting of alkyl, substituted alkyl, alkoxy, substituted alkoxy, acyl, acylamino, amino, substituted amino, aryl, substituted aryl, aryloxy, substituted aryloxy, carboxyl, carboxyl ester, cyano, cycloalkyl, substituted cycloalkyl, cycloalkyloxy, substituted cycloalkyloxy, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, and nitro, wherein said substituents are defined herein.

In some embodiments, the substituted aryl group is aryl substituted with —C(O)—NH$_2$.

"Aryloxy" refers to the group —O-aryl wherein aryl is defined herein.

"Substituted aryloxy" refers to the group —O-(substituted aryl) wherein substituted aryl is defined herein.

"Carbonyl" refers to the divalent group —C(O)— which is equivalent to —C(=O)—.

"Carboxy" or "carboxyl" refers to —COOH or a salt thereof.

"Carboxyl ester" or "carboxy ester" refers to the groups —C(O)O-alkyl, —C(O)O— substituted alkyl, —C(O)O-aryl, —C(O)O-substituted aryl, —C(O)O-cycloalkyl, —C(O)O-substituted cycloalkyl, —C(O)O-heteroaryloxy, —C(O)O-substituted heteroaryl, —C(O)O-heterocyclic, and —C(O)O-substituted heterocyclic wherein alkyl, substituted alkyl, cycloalkyl, substituted cycloalkyl, aryl, substituted aryl, heteroaryl, substituted heteroaryl, heterocyclic, and substituted heterocyclic are as defined herein.

"Cyano" refers to the group —C≡N.

"Cycloalkyl" refers to a saturated or unsaturated but nonaromatic cyclic alkyl groups of from 3 to 10 carbon atoms having single or multiple cyclic rings including fused, bridged, and spiro ring systems. $C_x$ cycloalkyl refers to a cycloalkyl group having x number of ring carbon atoms. Examples of suitable cycloalkyl groups include, for instance, adamantyl, cyclopropyl, cyclobutyl, cyclopentyl, and cyclooctyl. One or more rings can be aryl, heteroaryl, or heterocyclic provided that the point of attachment is through the non-aromatic, non-heterocyclic ring saturated carbocyclic ring.

"Substituted cycloalkyl" refers to a cycloalkyl group having from 1 to 5 or preferably 1 to 3 substituents selected from the group consisting of oxo, alkyl, substituted alkyl, alkoxy, substituted alkoxy, acyl, acylamino, acyloxy, amino, substituted amino, aryl, substituted aryl, aryloxy, substituted aryloxy, carboxyl, carboxyl ester, cyano, cycloalkyl, substituted cycloalkyl, cycloalkyloxy, substituted cycloalkyloxy, halo, hydroxy, heteroaryl, substituted heteroaryl, heteroaryloxy, substituted heteroaryloxy, heterocyclic, substituted heterocyclic, heterocyclyloxy, substituted heterocyclyloxy, and nitro, wherein said substituents are defined herein.

"Cycloalkyloxy" refers to —O-cycloalkyl wherein cycloalkyl is defined herein.

"Substituted cycloalkyloxy" refers to —O-(substituted cycloalkyl) wherein substituted cycloalkyl is defined herein.

"Halo" or "halogen" refers to fluoro, chloro, bromo and iodo and preferably is fluoro or chloro.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Preferred heteroaryls include 5 or 6 membered heteroaryls such as pyridinyl, pyrrolyl, indolyl, thiophenyl, and furanyl. In some embodiments, preferred heteroaryls include 5- or 6-membered non-oxygen containing heteroaryls. In some embodiments, preferred heteroaryls include 5- or 6-membered heteroaryls that exclude oxazoles. In some embodiments, a nitrogen-containing heteroaryl group is attached through a nitrogen on the heteroaryl group.

"Substituted heteroaryl" refers to heteroaryl groups that are substituted with from 1 to 5, preferably 1 to 3, or more preferably 1 to 2 substituents selected from the group consisting of the same group of substituents defined for substituted aryl. In some embodiments, the substituted heteroaryl group is a heteroaryl having a substituent, =NH, such as compound 53.

"Heteroaryloxy" refers to —O-heteroaryl and "substituted heteroaryloxy" refers to —O-substituted heteroaryl.

"Heterocycle" or "heterocyclic" or "heterocycloalkyl" or "heterocyclyl" refers to a saturated or partially saturated, but not aromatic, group having from 1 to 10 ring carbon atoms and from 1 to 4 ring heteroatoms selected from the group consisting of nitrogen, sulfur, or oxygen. Heterocycle encompasses single ring or multiple condensed rings, including fused bridged and spiro ring systems. In fused ring systems, one or more the rings can be cycloalkyl, aryl or heteroaryl provided that the point of attachment is through the non-aromatic ring. In one embodiment, the nitrogen and/or sulfur atom(s) of the heterocyclic group are optionally oxidized to provide for the N-oxide, sulfinyl, sulfonyl moieties.

"Substituted heterocyclic" or "substituted heterocycloalkyl" or "substituted heterocyclyl" refers to heterocyclyl groups that are substituted with from 1 to 5 or preferably 1 to 3 of the same substituents as defined for substituted cycloalkyl.

Examples of heterocycle and heteroaryl include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl, 1,1-dioxothiomorpholinyl, piperidinyl, pyrrolidine, and tetrahydrofuranyl.

"Heterocyclyloxy" or "heterocycloalkyloxy" refer to the group —O-(heterocyclyl) wherein heterocyclyl is defined herein.

"Substituted heterocyclyloxy" or "substituted heterocycloalkyloxy" refer to the group —O-(substituted heterocyclyloxy) wherein substituted heterocyclyloxy is defined herein.

"Heterocyclylthio" or "heterocycloalkylthio" refer to the group —S-(heterocyclyl) wherein heterocyclyl is defined herein.

"Substituted heterocyclylthio" or "substituted heterocycloalkylthio" refer to the group —S-(substituted heterocyclyl) wherein heterocyclyl is defined herein.

"Heteroarylthio" refers to the group —S-(heteroaryl) wherein heteroaryl is defined herein.

"Substituted heteroarylthio" refers to the group —S-(substituted heteroaryl) wherein substituted heteroaryl is defined herein.

"Nitro" refers to the group —NO$_2$.

"Oxo" refers to the atom (=O) or (—O$^-$).

"Spiro ring systems" refers to bicyclic ring systems that have a single ring carbon atom common to both rings.

Provided are also pharmaceutically acceptable salts, hydrates, solvates, tautomeric forms, and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "pharmaceutically acceptable salt" of a given compound refers to salts that retain the biological effectiveness and properties of the given compound, and which are not biologically or otherwise undesirable. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Likewise, pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines (i.e., $NH_2$(alkyl)), dialkyl amines (i.e., HN(alkyl)$_2$), trialkyl amines (i.e., N(alkyl)$_3$), substituted alkyl amines (i.e., $NH_2$(substituted alkyl)), di(substituted alkyl) amines (i.e., HN(substituted alkyl)$_2$), tri(substituted alkyl) amines (i.e., N(substituted alkyl)$_3$), alkenyl amines (i.e., $NH_2$(alkenyl)), dialkenyl amines (i.e., HN(alkenyl)$_2$), trialkenyl amines (i.e., N(alkenyl)$_3$), substituted alkenyl amines (i.e., $NH_2$(substituted alkenyl)), di(substituted alkenyl) amines (i.e., HN(substituted alkenyl)$_2$), tri(substituted alkenyl) amines (i.e., N(substituted alkenyl)$_3$, mono-, di- or tri-cycloalkyl amines (i.e., $NH_2$(cycloalkyl), HN(cycloalkyl)$_2$, N(cycloalkyl)$_3$), mono-, di- or tri-arylamines (i.e., $NH_2$(aryl), HN(aryl)$_2$, N(aryl)$_3$), or mixed amines, etc. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine, and the like.

Stereoisomers of compounds (also known as optical isomers) include all chiral, dl, stereoisomeric, and racemic forms of a structure, unless the specific stereochemistry is expressly indicated. Thus, compounds used in this disclosure include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of this disclosure.

The compounds of this disclosure may exist as solvates, especially hydrates. A "solvate" is formed by the interaction of a solvent and a compound. Solvates of salts of the compounds described herein are also provided. Hydrates may form during manufacture of the compounds or compositions comprising the compounds, or hydrates may form over time due to the hygroscopic nature of the compounds. Compounds of this disclosure may exist as organic solvates as well, including DMF, ether, and alcohol solvates among others. The identification and preparation of any particular solvate is within the skill of the ordinary artisan of synthetic organic or medicinal chemistry.

"Tautomer" refers to alternate forms of a compound that differ in the position of a proton, such as enol-keto and imine-enamine tautomers, or the tautomeric forms of heteroaryl groups containing a ring atom attached to both a ring —NH-moiety and a ring =N-moiety such as pyrazoles, imidazoles, benzimidazoles, triazoles, and tetrazoles.

"Treating" or "treatment" of a disease or disorder in a subject refers to 1) preventing the disease or disorder from occurring in a subject that is predisposed or does not yet display symptoms of the disease or disorder; 2) inhibiting the disease or disorder or arresting its development; or 3) ameliorating or causing regression of the disease or disorder.

"Subject" refers to a mammal. The mammal can be a human or non-human animal mammalian organism.

Unless indicated otherwise, the nomenclature of substituents that are not explicitly defined herein are arrived at by naming the terminal portion of the functionality followed by the adjacent functionality toward the point of attachment. For example, the substituent "alkoxycarbonylalkyl" refers to the group (alkoxy)-C(O)-(alkyl)-.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that, for example, substituted aryl groups are limited to -substituted aryl-(substituted aryl)-substituted aryl.

It is understood that the above definitions are not intended to include impermissible substitution patterns (e.g., methyl substituted with 5 fluoro groups). Such impermissible substitution patterns are well known to the skilled artisan.

2. Compounds of the Disclosure

This disclosure is directed to compounds, compositions, and methods of using said compounds or compositions to inhibit GSNOR. Also provided are methods useful in order treating diseases or disorders which are affected at least in part by GSNOR.

In some embodiments, provided is a compound of Formula I:

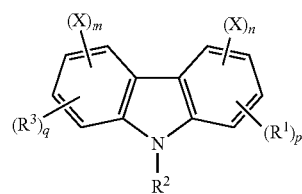

wherein:

m, n, p, q, X, $R^1$, $R^2$ and $R^3$ are as defined above;

or a tautomer or a pharmaceutically acceptable salt thereof.

Some embodiments herein provide for a compound of Formula I(a):

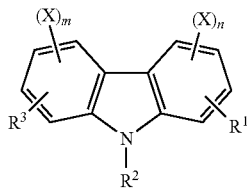

or a pharmaceutically acceptable salt, solvate, tautomer, stereoisomer, mixture of stereoisomers, prodrug, or deuterated analog thereof, wherein:

m and n independently are 0 or 1;

each X is independently halo or $C_{1-3}$ haloalkyl;

$R^2$ is selected from the group consisting of hydrogen, alkyl, substituted alkyl, acyl, acylamino, aryl, substituted aryl, heteroaryl, and substituted heteroaryl;

$R^1$ is selected from the group consisting of carboxyl, carboxyl ester, -arylene-carboxyl, -alkylene-carboxyl, -alkylene-carboxyl ester, -alkenylene-carboxyl, —O-alkylene-carboxyl, and heteroaryl; and $R^3$ is selected from the group consisting of halo, alkyl, substituted alkyl, amino, substituted amino, alkoxy, substituted alkoxy, heterocycloalkyl, substituted heterocycloalkyl, heterocycloalkyloxy, substituted heterocycloalkyloxy, heterocycloalkylthio, substituted heterocycloalkylthio, heteroaryl, substituted heteroaryl, heteroaryloxy, substituted heteroaryloxy, heteroarylthio, and substituted heteroarylthio.

Some embodiments herein provide for a compound of Formula I(a):

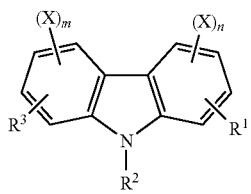

or a pharmaceutically acceptable salt, solvate, tautomer, stereoisomer, mixture of stereoisomers, prodrug, or deuterated analog thereof, wherein:

m and n independently are 0 or 1;

each X is independently halo or $C_{1-3}$ haloalkyl;

$R^2$ is selected from the group consisting of hydrogen, alkyl, acyl, acylamino, aryl, and heteroaryl, wherein each alkyl, aryl, and heteroaryl of $R^2$ is optionally substituted with 1 to 3 $R^{10}$;

$R^1$ is selected from the group consisting of carboxyl, carboxyl ester, -arylene-carboxyl, -alkylene-carboxyl, -alkylene-carboxyl ester, -alkenylene-carboxyl, —O-alkylene-carboxyl, and heteroaryl; and $R^3$ is selected from the group consisting of halo, alkyl, amino, alkoxy, heterocycloalkyl, heterocycloalkyloxy, heterocycloalkylthio, heteroaryl, heteroaryloxy, and heteroarylthio, wherein each alkyl, amino, alkoxy, heterocycloalkyl, heterocycloalkyloxy, heterocycloalkylthio, heteroaryl, heteroaryloxy, and heteroarylthio of $R^3$ is optionally substituted with 1 to 3 $R^{10}$;

each $R^{10}$ is independently halo, cyano, nitro, oxo, =NH, —$OR^{20}$, —$SR^{20}$, —$NR^{20}R^{21}$, $C_{1-12}$ alkyl, $C_{2-12}$ alkenyl, $C_{2-12}$ alkynyl, $C_{3-10}$ cycloalkyl, heterocyclyl, aryl, heteroaryl, —$C(O)R^{20}$, —$C(O)OR^{20}$, —$OC(O)OR^{20}$, —$OC(O)R^{20}$, —$C(O)NR^{20}R^{21}$, —$OC(O)NR^{20}R^{21}$, —$NR^{20}C(O)NR^{21}R^{22}$, —$S(O)_{1-2}R^{20}$, —$S(O)_{1-2}NR^{20}$, —$NR^{20}S(O)_{1-2}R^{21}$, —$NR^{20}S(O)_{1-2}NR^{21}R^{22}$, —$NR^{20}C(O)R^{21}$ or —$NR^{20}C(O)OR^{21}$, wherein each alkyl, alkenyl, alkynyl, cycloalkyl, heterocyclyl, aryl and heteroaryl of $R^{10}$ is independently optionally substituted with 1 to 3 $R^{11}$;

each $R^{11}$ is independently halo, cyano, nitro, oxo, —$OR^{25}$, —$SR^{25}$, —$NR^{25}R^{26}$, $C_{1-12}$ alkyl, $C_{2-12}$ alkenyl, $C_{2-12}$ alkynyl, $C_{3-10}$ cycloalkyl, heterocyclyl, aryl, heteroaryl, —$C(O)R^{25}$, —$C(O)OR^{25}$, —$OC(O)OR^{25}$, —$OC(O)R^{25}$, —$C(O)NR^{25}R^{26}$, —$OC(O)NR^{25}R^{26}$, —$NR^{25}C(O)NR^{25}R^{26}$, —$S(O)_{1-2}R^{25}$, —$S(O)_{1-2}NR^{25}$, —$NR^{25}S(O)_{1-2}R^{26}$, —$NR^{25}S(O)_{1-2}NR^{25}R^{26}$, —$NR^{25}C(O)R^{26}$ or —$NR^{25}C(O)OR^{26}$, wherein each alkyl, alkenyl, alkynyl, cycloalkyl, heterocyclyl, aryl and heteroaryl of $R^{11}$ is independently optionally substituted with one to three halo or $C_{1-12}$ alkyl independently optionally substituted by one to three oxo, halo, hydroxyl or amino;

each of $R^{20}$, $R^{21}$ and $R^{22}$ is independently hydrogen, $C_{1-12}$ alkyl, $C_{2-12}$ alkenyl, $C_{2-12}$ alkynyl, $C_{3-10}$ cycloalkyl, heterocyclyl, aryl, heteroaryl, —$C(O)R^{40}$, —$C(O)OR^{40}$, —$C(O)NR^{40}R^{41}$, —$S(O)_{1-2}R^{40}$ or —$S(O)_{1-2}NR^{40}$, wherein each alkyl, alkenyl, alkynyl, cycloalkyl, heterocyclyl, aryl and heteroaryl of $R^{20}$, $R^{21}$ and $R^{22}$ is independently optionally substituted with one to three $R^{11}$; or two of $R^{20}$, $R^{21}$ and $R^{22}$ are taken together with the atoms to which they are attached to form a heterocyclyl independently optionally substituted by one to three halo, oxo, or $C_{1-12}$ alkyl independently optionally substituted by one to three oxo, halo, hydroxyl or amino;

each $R^{25}$ and $R^{26}$ is independently hydrogen or $C_{1-12}$ alkyl independently optionally substituted with one to three oxo, halo, hydroxyl or amino; or $R^{25}$ and $R^{26}$ are taken together with the atoms to which they are attached to form a heterocyclyl independently optionally substituted by one to three halo or $C_{1-12}$ alkyl independently optionally substituted by one to three oxo, halo, hydroxyl or amino; and each $R^{40}$ and $R^{41}$ is independently hydrogen or $C_{1-12}$ alkyl independently optionally substituted with one to three oxo, halo, hydroxyl or amino; or $R^{40}$ and $R^{41}$ are taken together with the atoms to which they are attached to form a heterocyclyl independently optionally substituted by one to three halo or $C_{1-12}$ alkyl independently optionally substituted by one to three oxo, halo, hydroxyl or amino.

Some embodiments herein provide for a compound of Formula I(b):

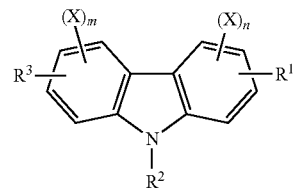

wherein:

m and n independently are 0 or 1;

each X is independently F, Cl, or $CF_3$;

R¹ is selected from the group consisting of alkyl, substituted alkyl, amino, substituted amino, alkoxy, substituted alkoxy, heterocycloalkyl, substituted heterocycloalkyl, heterocycloalkyloxy, substituted heterocycloalkyloxy, heterocycloalkylthio, substituted heterocycloalkylthio, heteroaryl, substituted heteroaryl, heteroaryloxy, substituted heteroaryloxy, heteroarylthio, and substituted heteroarylthio;

R² is selected from the group consisting of hydrogen, alkyl, substituted alkyl, acyl, acylamino, aryl, substituted aryl, heteroaryl, and substituted heteroaryl; and R³ is selected from the group consisting of carboxyl, carboxyl ester, -arylene-carboxyl, -arylene-carboxyl ester, -oxyalkylene-carboxyl, -oxyalkylene-carboxyl ester, -alkylene-carboxyl, -alkylene-carboxyl ester, -alkenylene-carboxyl, and -alkenylene-carboxyl ester;

or a tautomer, solvate, or a pharmaceutically acceptable salt thereof.

Some embodiments herein provide for a compound of Formula I(c):

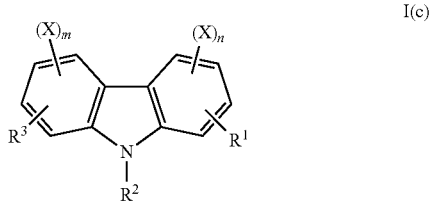

or a pharmaceutically acceptable salt, solvate, tautomer, stereoisomer, mixture of stereoisomers, prodrug, or deuterated analog thereof, wherein:

m and n independently are 0 or 1;

each X is independently halo or $C_{1-3}$ haloalkyl;

R² is selected from the group consisting of hydrogen, alkyl, acyl, acylamino, aryl, and heteroaryl, wherein each alkyl, aryl, and heteroaryl of R² is optionally substituted with 1 to 3 $R^{10}$;

R¹ is selected from the group consisting of carboxyl, carboxyl ester, -arylene-carboxyl, -alkylene-carboxyl, -alkylene-carboxyl ester, -alkenylene-carboxyl, —O-alkylene-carboxyl, and heteroaryl; and R³ is selected from the group consisting of halo, alkyl, amino, alkoxy, heterocycloalkyl, heterocycloalkyloxy, heterocycloalkylthio, heteroaryl, heteroaryloxy, and heteroarylthio, wherein each alkyl, amino, alkoxy, heterocycloalkyl, heterocycloalkyloxy, heterocycloalkylthio, heteroaryl, heteroaryloxy, and heteroarylthio of R³ is optionally substituted with 1 to 3 $R^{10}$;

each $R^{10}$ is independently halo, cyano, nitro, oxo, —OR²⁰, —SR²⁰, —NR²⁰R²¹, $C_{1-12}$ alkyl, $C_{2-12}$ alkenyl, $C_{2-12}$ alkynyl, $C_{3-10}$ cycloalkyl, heterocyclyl, aryl, heteroaryl, —C(O)R²⁰, —C(O)OR²⁰, —OC(O)OR²⁰, —OC(O)R²⁰, —C(O)NR²⁰R²¹, —OC(O)NR²⁰R²¹, —NR²⁰C(O)NR²¹R²², —S(O)$_{1-2}$R²⁰, —S(O)$_{1-2}$NR²⁰, —NR²⁰S(O)$_{1-2}$R²¹, —NR²⁰S(O)$_{1-2}$NR²¹R²², —NR²⁰C(O)R²¹ or —NR²⁰C(O)OR²¹, wherein each alkyl, alkenyl, alkynyl, cycloalkyl, heterocyclyl, aryl and heteroaryl of $R^{10}$ is independently optionally substituted with 1 to 3 $R^{11}$;

each $R^{11}$ is independently halo, cyano, nitro, oxo, —OR²⁵, —SR²⁵, —NR²⁵R²⁶, $C_{1-12}$ alkyl, $C_{2-12}$ alkenyl, $C_{2-12}$ alkynyl, $C_{3-10}$ cycloalkyl, heterocyclyl, aryl, heteroaryl, —C(O)R²⁵, —C(O)OR²⁵, —OC(O)OR²⁵, —OC(O)R²⁵, —C(O)NR²⁵R²⁶, —OC(O)NR²⁵R²⁶, —NR²⁵C(O)NR²⁵R²⁶, —S(O)$_{1-2}$R²⁵, —S(O)$_{1-2}$NR²⁵, —NR²⁵S(O)$_{1-2}$R²⁶, —NR²⁵S(O)$_{1-2}$NR²⁵R²⁶, —NR²⁵C(O)R²⁶ or —NR²⁵C(O)OR²⁶, wherein each alkyl, alkenyl, alkynyl, cycloalkyl, heterocyclyl, aryl and heteroaryl of $R^{11}$ is independently optionally substituted with one to three halo or $C_{1-12}$ alkyl independently optionally substituted by one to three oxo, halo, hydroxyl or amino;

each of R²⁰, R²¹ and R²² is independently hydrogen, $C_{1-12}$ alkyl, $C_{2-12}$ alkenyl, $C_{2-12}$ alkynyl, $C_{3-10}$ cycloalkyl, heterocyclyl, aryl, heteroaryl, —C(O)R⁴⁰, —C(O)OR⁴⁰, —C(O)NR⁴⁰R⁴¹, —S(O)$_{1-2}$R⁴⁰ or —S(O)$_{1-2}$NR⁴⁰, wherein each alkyl, alkenyl, alkynyl, cycloalkyl, heterocyclyl, aryl and heteroaryl of R²⁰, R²¹ and R²² is independently optionally substituted with one to three $R^{11}$; or two of R²⁰, R²¹ and R²² are taken together with the atoms to which they are attached to form a heterocyclyl independently optionally substituted by one to three halo, oxo, or $C_{1-12}$ alkyl independently optionally substituted by one to three oxo, halo, hydroxyl or amino;

each R²⁵ and R²⁶ is independently hydrogen or $C_{1-12}$ alkyl independently optionally substituted with one to three oxo, halo, hydroxyl or amino; or R²⁵ and R²⁶ are taken together with the atoms to which they are attached to form a heterocyclyl independently optionally substituted by one to three halo or $C_{1-12}$ alkyl independently optionally substituted by one to three oxo, halo, hydroxyl or amino; and each R⁴⁰ and R⁴¹ is independently hydrogen or $C_{1-12}$ alkyl independently optionally substituted with one to three oxo, halo, hydroxyl or amino; or R⁴⁰ and R⁴¹ are taken together with the atoms to which they are attached to form a heterocyclyl independently optionally substituted by one to three halo or $C_{1-12}$ alkyl independently optionally substituted by one to three oxo, halo, hydroxyl or amino.

In some embodiments, provided herein is a compound of Formula II:

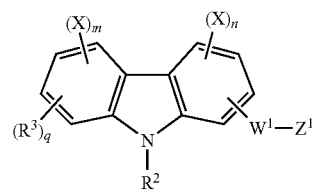

wherein:

m, n, q, X, R² and R³ are as defined above;

W¹ is a bond or a $C_1$-$C_4$ alkyl;

Z¹ is selected from the group consisting of a carboxyl or a carboxyl ester group; or a tautomer or a pharmaceutically acceptable salt thereof.

In some embodiments, provided herein is a compound of Formula III:

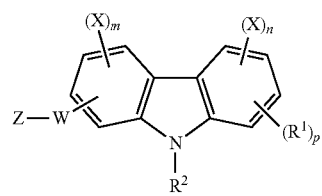

m, n, p, X, R¹ and R² are as defined above;

W is selected from the group consisting of a bond, alkyl, substituted alkyl, alkoxy, substituted alkoxy, aryl, substituted aryl, heteroaryl, substituted heteroaryl, heteroaryloxy, and substituted heteroaryloxy;

Z is selected from the group consisting of hydrogen, amino, substituted amino, and $CF_3$;

or a tautomer or a pharmaceutically acceptable salt thereof.

In some embodiments, provided herein is a compound of Formula III(a):

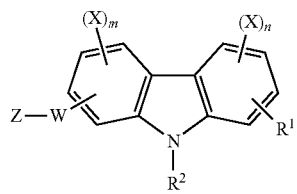

m, n, p, X, $R^1$ and $R^2$ are as defined above;

W is selected from the group consisting of alkylene, substituted alkylene, —O-alkylene, substituted —O-alkylene, arylene, substituted arylene, heteroarylene, substituted heteroarylene, —O-heteroarylene, and substituted —O-heteroarylene;

Z is selected from the group consisting of hydrogen, amino, substituted amino, and $CF_3$;

or a tautomer or a pharmaceutically acceptable salt thereof.

In some embodiments, provided herein is a compound of Formula IV:

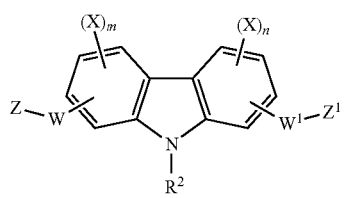

wherein:

m, n, W, $W^1$, X, Z, $Z^1$ and $R^2$ are as defined above; or a tautomer and/or a pharmaceutically acceptable salt thereof.

In some embodiments, provided herein is a compound of Formula V:

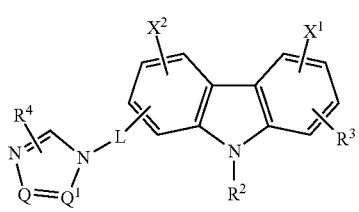

wherein:

$R^2$ and $R^3$ are as defined above;

$R^4$ is H, $C_1$-$C_4$ alkyl, or $CF_3$;

$X^1$ and $X^2$ are the same and selected from H, F, and $CF_3$;

L is a bond or

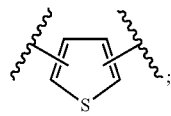

Q is CH or N; and
$Q^1$ is CH or N;
provided that Q and $Q^1$ are not both N;
or a tautomer or a pharmaceutically acceptable salt thereof.

In some embodiments, Q is CH and $Q^1$ is CH. In some embodiments, L is a bond.

It is understood that reference herein to a compound of Formula I also includes compounds of Formula II, III, IV and V.

In one aspect, this disclosure provides for one or more compounds of a core structure of carbazole (benzo[b]indole) which have a numbering scheme as shown below:

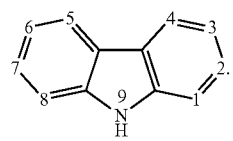

In some embodiments, the compound is of Formula I wherein $R^3$ is

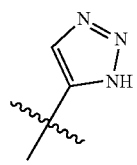 [SMILES: *c1cnn[nH]1]

and n is 0.

In some embodiments, the compound is of Formula I wherein $R^3$ is

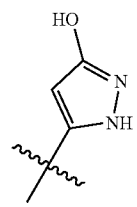 [SMILES: *c1cc(O)n[nH]1]

and n is 0.

In some embodiments, the compound is of Formula I wherein $R^3$ is

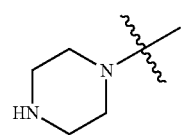

and q is 1.

In some embodiments, the compound is of Formula I wherein R³ is

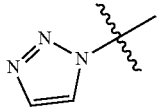

and q is 1.

In some embodiments, the compound is of Formula III wherein R³ is

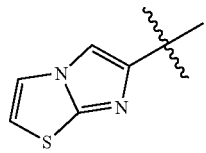 [SMILES: *c1cn2ccsc2n1]

and q is 1.

In some embodiments, the compound is of Formula III wherein R³ is OMe and q is 1 and n is 1.

In some embodiments, the compound is of Formula III wherein R³ is

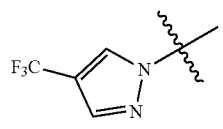 [SMILES: *n1cc(C(F)(F)F)cn1]

and q is 1.

In some embodiments, the compound is of Formula III wherein R³ is

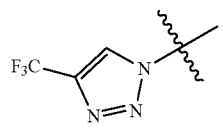 [SMILES: *n1cc(C(F)(F)F)nn1]

and q is 1.

In some embodiments, the compound is of Formula III wherein R³ is

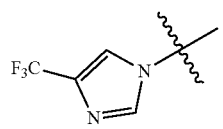 [SMILES: *n1cnc(C(F)(F)F)c1]

and q is 1.

In some embodiments, the compound is of Formula III wherein R³ is

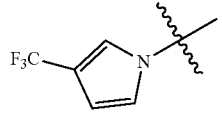

and q is 1.

In some embodiments, the compound is of Formula I wherein R³ is

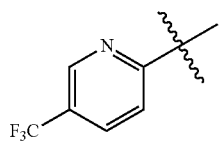

and q is 1.

In some embodiments, the compound is of Formula I wherein R³ is

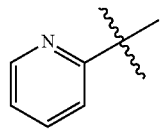 [SMILES: *c1ccccn1]

and q is 1.

In some embodiments, the compound is of Formula I wherein R³ is

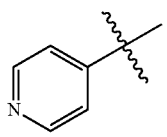 [SMILES: *c1ccncc1]

and q is 1.

In some embodiments, the compound is of Formula I wherein R³ is

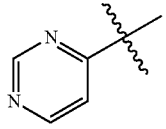 [SMILES: *c1ccncn1]

and q is 1.

In some embodiments, the compound is of Formula I wherein R³ is

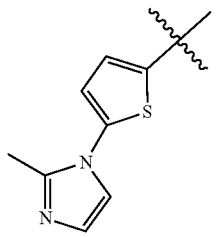 [SMILES: *c1ccc(-n2ccnc2C)s1]

and q is 1.

In some embodiments, the compound is of Formula I wherein R³ is

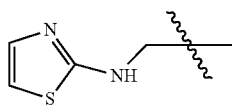 [SMILES: *CNc1nccs1]

and q is 1.

In some embodiments, the compound is of Formula I wherein R³ is

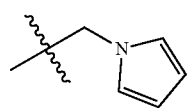 [SMILES: *Cn1cccc1]

and q is 1.

In some embodiments, the compound is of Formula I wherein R³ is

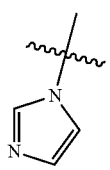

and q is 1.

In some embodiments, the compound is of Formula I wherein R³ is

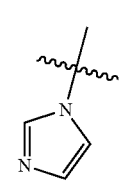

and R¹ is CO₂H q is 1.

In some embodiments, the compound is of Formula I wherein R³ is

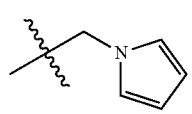 [SMILES: *Cn1cccc1]

and R¹ is CO₂H q is 1.

In some embodiments, the compound is of Formula I wherein R³ is

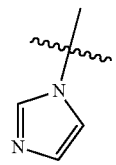 [SMILES: *n1ccnc1]

and R¹ is CO₂H and R² contains an aminocarbonyl group and q is 1 and m is 0 and n is 0.

In some embodiments, the compound is of Formula I wherein R³ is

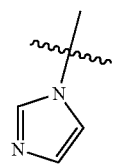

and R¹ is CO₂H and R² is an substituted aryl group and q is 1 and m is 0 and n is 0.

In some embodiments, the compound is of Formula I wherein R³ is

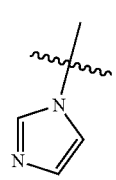

and R¹ is —(CH₂)₂CO₂H and R² contains an aminocarbonyl group and q is 1 and m is 0 and n is 0.

In some embodiments, the compound is of Formula I wherein R³ is

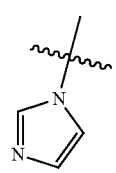

and R¹ is —(CH₂)₂CO₂H and R² contains an aminocarbonyl group and q is 1 and m is 1 and n is 0.

In some embodiments, the compound is of Formula I wherein R³ is

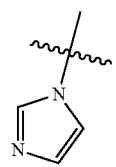 [SMILES: *n1ccnc1]

and R¹ is —(CH₂)₂CO₂H and R² contains an aminocarbonyl group and q is 1 and m is 0 and n is 1.

In some embodiments, the compound is of Formula I wherein $R^3$ is

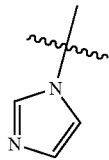

and $R^1$ is —$(CH_2)_2CO_2H$ and $R^2$ contains an aminocarbonyl group and q is 1.

In some embodiments, the compound is of Formula III wherein $R^3$ is

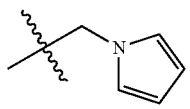 [SMILES: *Cn1cccc1]

and n is 0.

In some embodiments, $R^3$ is selected from the group consisting of:

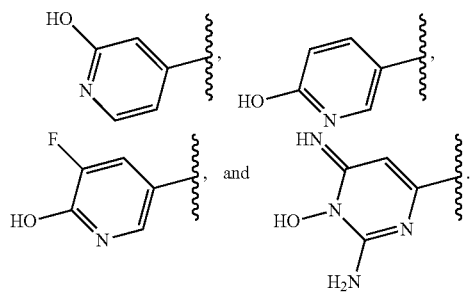

In some embodiments, the compound is of a Formula disclosed herein wherein $R^1$ is a substituted $C_1$-$C_5$ alkyl-carboxyl. In some embodiments, the compound is of a Formula disclosed herein wherein $R^3$ is a substituted $C_1$-$C_3$ alkyl-carboxyl. In some embodiments, the compound is of a Formula disclosed herein wherein $R^3$ is

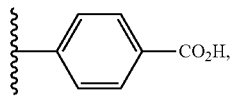

or an ester thereof.

In some embodiments, $R^3$ is

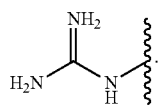

In some embodiments, $R^1$ is carboxyl, $C_1$-$C_6$ alkylene-carboxyl, $C_1$-$C_6$ alkenylene-carboxyl, —O—$C_1$-$C_6$ alkylene-carboxyl, or heteroaryl In some embodiments, $R^1$ is carboxyl.

In some embodiments, $R^1$ is $C_1$-$C_6$ alkylene-carboxyl. In some embodiments, $R^1$ is a substituted $C_1$-$C_6$ alkylene-carboxyl. In some embodiments, $R^1$ is $C_1$-$C_6$ alkylene-carboxyl substituted with 1 to 5 halo groups. In some embodiments, $R^1$ is $C_1$-$C_6$ alkylene-carboxyl substituted with 1 to 5 fluoro groups. In some embodiments, $R^1$ is

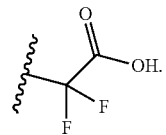 [SMILES: *C(F)(F)C(=O)O]

In some embodiments, $R^1$ is $C_1$-$C_6$ alkenylene-carboxyl.

In some embodiments, $R^1$ is —O—$C_1$-$C_6$ alkylene-carboxyl. In some embodiments, $R^1$ is

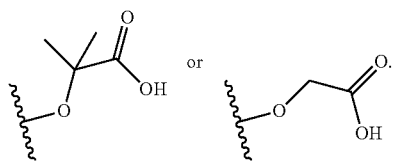

In some embodiments, $R^1$ is a heteroaryl. In some embodiments, $R^1$ is a 5-6 membered heteroaryl ring. In some embodiments, $R^1$ is a 5-6 membered nitrogen-containing heteroaryl ring. In some embodiments, $R^1$ is a tetrazole ring.

In some embodiments, $R^2$ is hydrogen.

In some embodiments, $R^2$ is $C_{1-6}$ alkyl. In some embodiments, $R^2$ is $C_{1-6}$ substituted alkyl. In some embodiments, $R^2$ is $C_{1-6}$ alkyl substituted with —C(O)—$NH_2$. In some embodiments, $R^2$ is alkyl substituted with cyano. In some embodiments, $R^2$ is $C_{1-4}$ alkyl substituted with cyano. In some embodiments, $R^2$ is —$(CH_2)_4$—CN.

In some embodiments, $R^2$ is an aryl ring. In some embodiments, $R^2$ is a substituted aryl ring. In some embodiments, $R^2$ is an aryl ring substituted with 1 to 3 groups independently selected from halo, $C_{1-3}$ alkyl, $C_{1-3}$ alkoxy, —CO—$NH_2$, cyano, and nitro.

In some embodiments, $R^2$ is substituted alkyl, substituted aryl, or acyl. In some embodiments, $R^2$ is substituted alkyl. In some embodiments, $R^2$ is

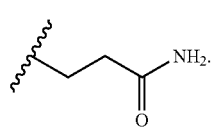

In some embodiments, $R^2$ is substituted aryl. In some embodiments, $R^2$ is

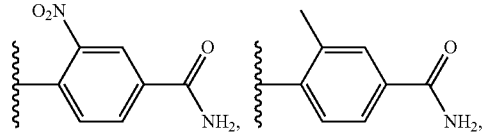

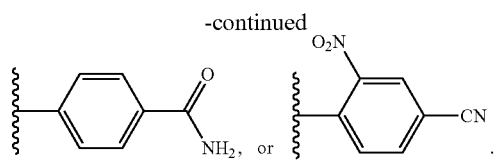

In some embodiments, $R^2$ is acyl.

In some embodiments, X is halo. In some embodiments, X is $C_{1-3}$ haloalkyl. In some embodiments, X is $CF_3$.

In some embodiments, each $R^{10}$ is independently halo, cyano, nitro, —$OR^{20}$, —$SR^{20}$, —$NR^{20}R^{21}$, $C_{1-12}$ alkyl, $C_{2-12}$ alkenyl, $C_{2-12}$ alkynyl, $C_{3-10}$ cycloalkyl, heterocyclyl, aryl, heteroaryl, —$C(O)R^{20}$, —$C(O)OR^{20}$, —$OC(O)OR^{20}$, —$OC(O)R^{20}$, —$C(O)NR^{20}R^{21}$, —$OC(O)NR^{20}R^{21}$, —$NR^{20}C(O)NR^{21}R^{22}$, —$S(O)_{1-2}R^{20}$, —$S(O)_{1-2}NR^{20}$, —$NR^{20}S(O)_{1-2}R^{21}$, —$NR^{20}S(O)_{1-2}NR^{21}R^{22}$, —$NR^{20}C(O)R^{21}$ or —$NR^{20}C(O)OR^{21}$, wherein each alkyl, alkenyl, alkynyl, cycloalkyl, heterocyclyl, aryl and heteroaryl of $R^{10}$ is independently optionally substituted with 1 to 3 $R^{11}$.

In some embodiments, each $R^{11}$ is independently halo, cyano, nitro, —$OR^{25}$, —$SR^{25}$, —$NR^{25}R^{26}$, $C_{1-12}$ alkyl, $C_{2-12}$ alkenyl, $C_{2-12}$ alkynyl, $C_{3-10}$ cycloalkyl, heterocyclyl, aryl, heteroaryl, —$C(O)R^{25}$, —$C(O)OR^{25}$, —$OC(O)OR^{25}$, —$OC(O)R^{25}$, —$C(O)NR^{25}R^{26}$, —$OC(O)NR^{25}R^{26}$, —$NR^{25}C(O)NR^{25}R^{26}$, —$S(O)_{1-2}R^{25}$, —$S(O)_{1-2}NR^{25}$, —$NR^{25}S(O)_{1-2}R^{26}$, —$NR^{25}S(O)_{1-2}NR^{25}R^{26}$, —$NR^{25}C(O)R^{26}$ or —$NR^{25}C(O)OR^{26}$, wherein each alkyl, alkenyl, alkynyl, cycloalkyl, heterocyclyl, aryl and heteroaryl of $R^{11}$ is independently optionally substituted with one to three halo or $C_{1-12}$ alkyl independently optionally substituted by one to three oxo, halo, hydroxyl or amino.

Some embodiments provided herein are directed to a compound of Table 1, wherein the compound is selected from the group consisting of:

TABLE 1

| Compound | Structure | HRMS |
|---|---|---|
| 1 | 2-carboxyl-7-methoxycarbazole | |
| 2 | 2-carboxyl-7-methoxy-9-(2-aminocarbonyleth-1-yl) carbazole | |
| 3 | 2-carboxyl-7-methoxy-9-(4-aminocarbonyl-phenyl) carbazole | |
| 4 | 2-carboxyl-7-[5-(2-methylimidazol-1-yl)thiophen-2-yl] carbazole | |

TABLE 1-continued

| Compound | Structure | HRMS |
|---|---|---|
| 5 | 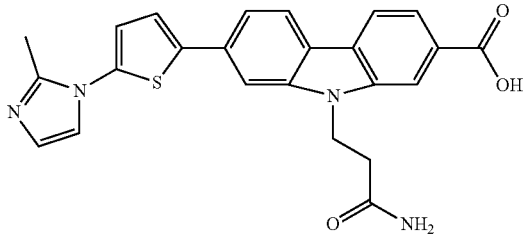<br>2-carboxyl-7-[5-(2-methylimidazol-1-yl)<br>thiophen-2-yl] 9-(aminocarbonyleth-1-yl)<br>carbazole | |
| 6 | 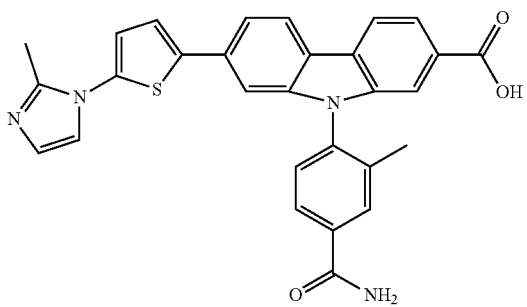<br>2-carboxyl-7-[5-(2-methylimidazol-1-yl)<br>thiophen-2-yl]-9-(aminocarbonyl-2-<br>methlyphenyl) carbazole | |
| 7 | 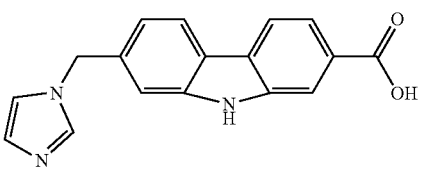<br>2-carboxyl-7-(imidazol-1-yl)methyl carbazole | |
| 8 | 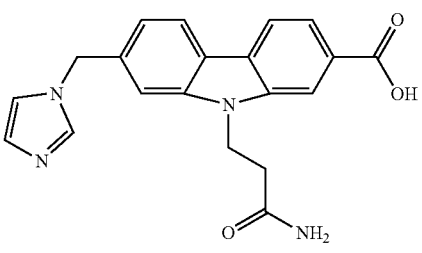<br>2-carboxyl-7-(imidazol-1-yl)methyl-<br>9-(2-aminocarbonyleth-1-yl)<br>carbazole | |
| 9 | 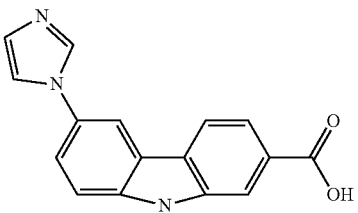<br>2-carboxyl-5-imidazol-1-yl carbazole | |

TABLE 1-continued
| Compound | Structure | HRMS |
| --- | --- | --- |
| 10 | 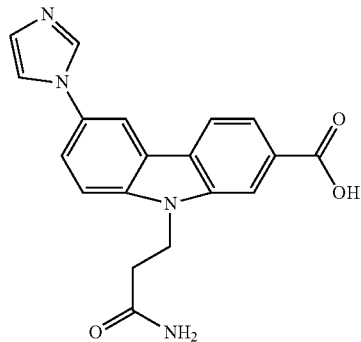 2-carboxyl-6-imidazol-1-yl-9-((2-aminocarbonyleth-1-yl) carbazole | |
| 11 | 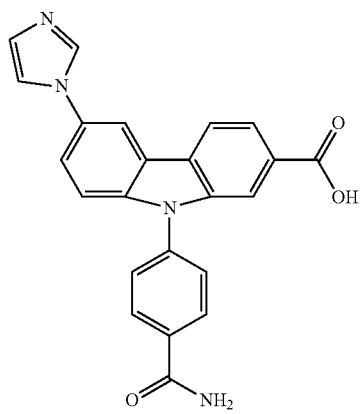 2-carboxyl-6-imidazol-1-yl-9-(4-aminocarbonylphenyl) carbazole | |
| 12 | 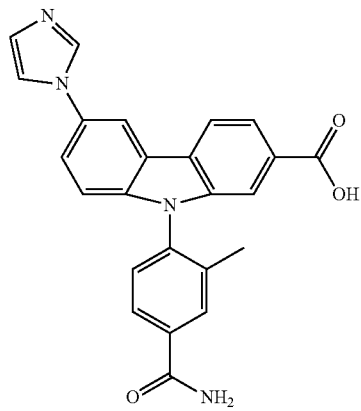 2-carboxyl-6-imidazol-1-yl-9-(4-aminocarbonyl-2-methylphenyl) carbazole | |

TABLE 1-continued
| Compound | Structure | HRMS |
|---|---|---|
| 13 | 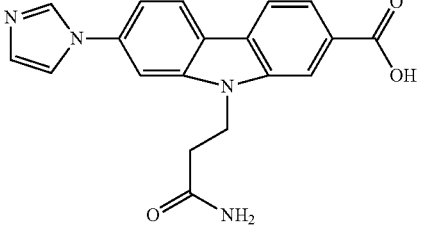<br>2-carboxyl-7-imidazol-1-yl-9-(2-aminocarbonyleth-1-yl) carbazole | |
| 14 | 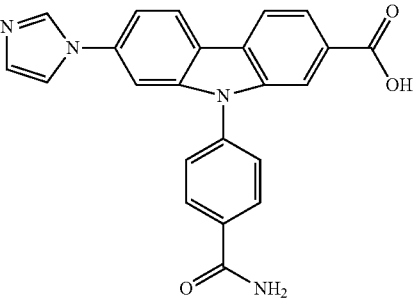<br>2-carboxyl-7-imidazol-1-yl-9-(4-aminocarbonyl-2-phenyl) carbazole | |
| 15 | 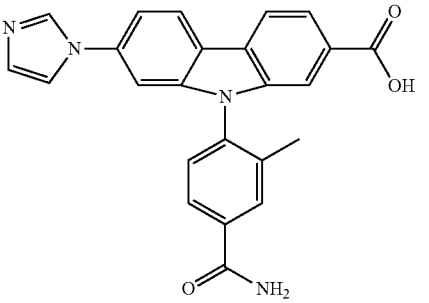<br>2-carboxyl-7-imidazol-1-yl-9-(4-aminocarbonyl-2-methylphenyl) carbazole | |
| 16 | 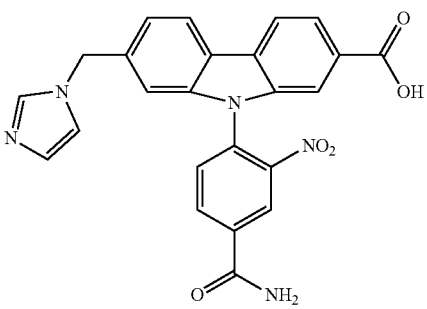<br>2-carboxyl-7-(imidazol-1-ylmethyl)-9-(4-aminocarbonyl-2-nitrophenyl) carbazole | |

TABLE 1-continued

| Compound | Structure | HRMS |
| --- | --- | --- |
| 17 | 9-(3-amino-3-oxo-propyl)-6-(1H-imidazol-1-yl)-2-(2-carboxyethyl)-9H-carbazole | 377.1616 [M + H]+ |
| 18 | 3-(imidazol-1H-yl)-7-(2-carboxyethyl)-9H-(4-cyanophenyl) carbazole | 407 [M + H] |
| 19 | 3-(imidazol-1H-yl)-7-(2-carboxyethyl)-9H-(2-methyl-4-cyanophenyl) carbazole | 421 [M + H] |
| 20 | 3-(imidazol-1H-yl)-7-(2-carboxyethyl)-9H-(4-carbamoylphenyl) carbazole | 425 [M + H] |

TABLE 1-continued

| Compound | Structure | HRMS |
|---|---|---|
| 21 | 3-(imidazol-1H-yl)-7-(2-carboxyethyl)-9H-(2-methyl-4-carbamoylphenyl) carbazole | 439 [M + H] |
| 22 | 3-(imidazol-1H-yl)-7-(2-carboxyethyl)-9H-(4-chlorophenyl) carbazole | 416 [M + H] |
| 23 | 3-(imidazol-1H-yl)-7-(2-carboxyethyl)-9H-(4-hydroxyphenyl) carbazole | 398 [M + H] |
| 24 | 3-(imidazol-1H-yl)-7-(2-carboxyethyl)-9H-(4-methoxyphenyl) carbazole | 412 [M + H] |

TABLE 1-continued

| Compound | Structure | HRMS |
|---|---|---|
| 25 | 3-(imidazol-1H-yl)-7-(2-carboxyethyl)-9H-(2-methyl-4-methoxyphenyl) carbazole | 426 [M + H] |
| 26 | 3-(imidazol-1H-yl)-7-(2-carboxyethyl)-9H-(2-cyanoethyl) carbazole | 359 [M + H] |
| 27 | 3-(imidazol-1H-yl)-7-(2-carboxyethyl)-9H-(3-cyanopropyl) carbazole | |
| 28 | 2-[5-(3-methylimidazol-1H-yl)thiophen-2-yl] 9H-(2-carbamoyleth-1-yl) carbazole 7-carboxylic acid | |

TABLE 1-continued

| Compound | Structure | HRMS |
|---|---|---|
| 29 | 2-(imidazol-1H-ylmethyl)-9H-(4-carbomoyl-2-nitrophenyl) carbazole 7-carboxylic acid | |
| 30 | 3-(imidazol-1H-yl)-7-(2-carboxyethyl)-9H-carbazole | |
| 31 | 3-(9-(4-cyanobutyl)-6-(1H-imidazol-1-yl)-9H-carbazol-2-yl)propanoic acid | 387 [M + H] |
| 32 | 9-(4-cyanobutyl)-6-(1H-imidazol-1-yl)-9H-carbazole-2-carboxylic acid | 359 [M + 1]$^+$<br>357 [M − 1]$^−$<br>715 [2M − 1]$^−$ |
| 33 | 7-bromo-9-(4-cyanobutyl)-9H-carbazole-2-carboxylic acid | 395 [M + 23]$^+$<br>371 [M − H]$^−$ |

TABLE 1-continued

| Compound | Structure | HRMS |
|---|---|---|
| 34 | 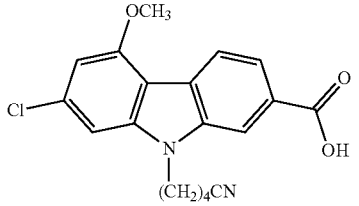 7-chloro-9-(4-cyanobutyl)-5-methoxy-9H-carbazole-2-carboxylic acid | 357.20 [M + H]⁺ |
| 35 | 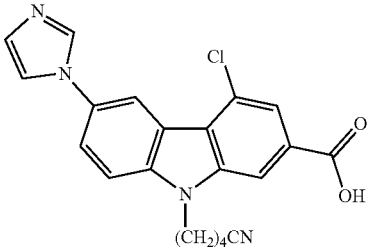 4-chloro-9-(4-cyanobutyl)-6-(1H-imidazol-1-yl)-9H-carbazole-2-carboxylic acid | 393 [M + H]⁺<br>391 [M − H]⁻ |
| 36 | 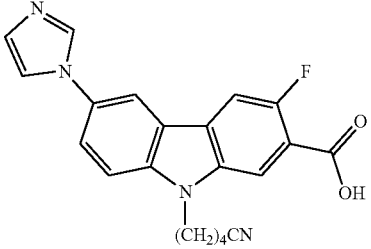 9-(4-cyanobutyl)-3-fluoro-6-(1H-imidazol-1-yl)-9H-carbazole-2-carboxylic acid | 377 [M + M]⁺<br>375 [M − H]⁻ |
| 37 | 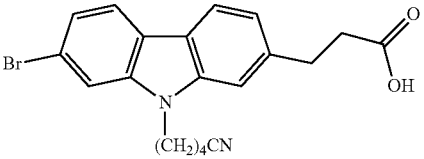 3-(7-bromo-9-(4-cyanobutyl)-9H-carbazol-2-yl)carboxylic acid | 397 [M − H]⁻ |
| 38 | 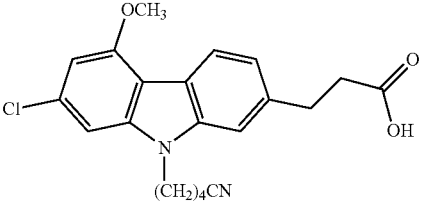 3-(7-bromo-9-(4-cyanobutyl)-5-methoxy-9H-carbazol-2-yl)propanoic acid | 383.20 [M − H]⁻ |

TABLE 1-continued

| Compound | Structure | HRMS |
|---|---|---|
| 39 | 9-(4-cyanobutyl)-1-fluoro-6-(1H-imidazol-1-yl)-9H-carbazole-2-carboxylic acid | 377 [M + H]+<br>376 [M − H]− |
| 40 | (E)-3-(9-(4-cyanobutyl)-6-(1H-imidazol-1-yl)-9H-carbazol-2-yl)acrylic acid | 385.25 [M + H]+ |
| 41 | (E)-3-(7-bromo-9-(4-cyanobutyl)-9H-carbazol-2-yl)acrylic acid | 397 [M + H]+<br>419 [M + Na]+ |
| 42 | (E)-3-(7-chloro-9-(4-cyanobutyl)-5-methoxy-9H-carbazol-2-yl)acrylic acid | 381.20 [M − H]− |
| 43 | 5-(6-(1H-imidazol-1-yl)-2-(1H-tetrazol-5-yl)-9H-carbazol-9-yl)pentanenitrile | 383.30 [M + H]+ |

TABLE 1-continued

| Compound | Structure | HRMS |
|---|---|---|
| 44 | 5-(2-chloro-4-methoxy-7-(1H-tetrazol-5-yl)-9H-carbazol-9-yl)pentanenitrile | 381.25 [M + H]+ |
| 45 | 5-(2-bromo-7-(1H-tetrazol-5-yl)-9H-carbazol-9-yl)pentanenitrile | 395 [M + 1]+<br>393 [M − 1]− |
| 46 | 2-((9-(4-cyanobutyl)-6-(1H-imidazol-1-yl)-9H-carbazol-2-yl)oxy)acetic acid | 389.25 [M + H]+ |
| 47 | 2-((7-bromo-9-(4-cyanobutyl)-9H-carbazol-2-yl)oxy)acetic acid | 401 [M + 1]+<br>423 [M + 23]+<br>399 [M − 1]− |
| 48 | 2-((7-chloro-9-(4-cyanobutyl)-5-methoxy-9H-carbazol-2-yl)oxy)acetic acid | 385.20 [M − H]− |

TABLE 1-continued

| Compound | Structure | HRMS |
|---|---|---|
| 49 | 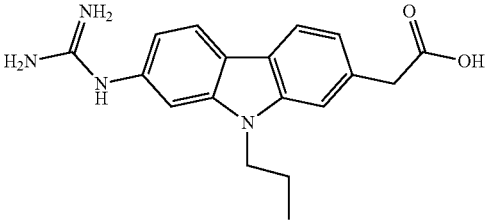 2-(7-((amino(λ⁴-azaneylidene)methyl)amino)-9-propyl-9H-carbazol-2-yl)acetic acid | |
| 50 | 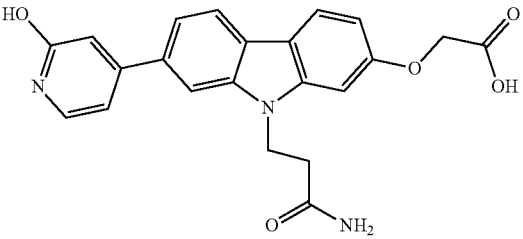 2-((9-(3-amino-3-oxopropyl)-7-(2-hydroxypyridin-4-yl)-9H-carbazol-2-yl)oxy)acetic acid | |
| 51 | 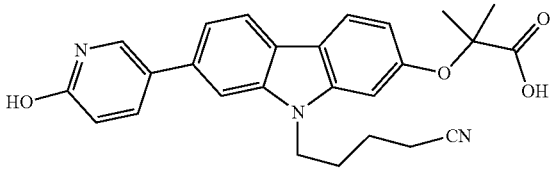 2-((9-(4-cyanobutyl)-7-(6-hydroxypyridin-3-yl)-9H-carbazol-2-yl)oxy)-2-methylpropanoic acid | |
| 52 | 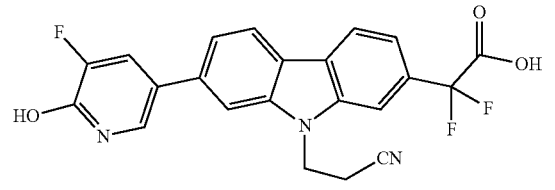 2-(9-(2-cyanoethyl)-7-(5-fluoro-6-hydroxypyridin-3-yl)-9H-carbazol-2-yl)-2,2-difluoroacetic acid | |
| 53 | 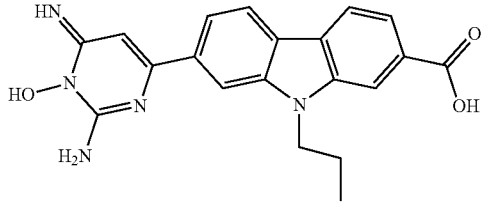 7-(2-amino-1-hydroxy-6-imino-1,6-dihydropyrimidin-4-yl)-9-propyl-9H-carbazole-2-carboxylic acid | |

TABLE 1-continued

| Compound | Structure | HRMS |
|---|---|---|
| 54 | sodium 3-(9-(3-amino-3-oxopropyl)-6-(1H-imidazol-1-yl)-9H-carbazol-2-yl)propanoate | 377 [M − Na + H]⁺ | or a tautomer, solvate, or pharmaceutically acceptable salt thereof.

Some embodiments provided herein are directed to a compound of formula:

| Compound | Structure | HRMS |
|---|---|---|
| A1 | 9-(3-amino-3-oxopropyl)-7-[(1H-imidazol-1-yl)methyl]-9H-carbazole-2-carboxylic acid | |
| B1 | 9-(3-amino-3-oxopropyl)-6-(1H-imidazol-1-yl)-9H-carbazole-2-carboxylic acid | |
| C1 | 9-(4-aminocarbonyl-2-nitrophenyl)-6-[(1H-imidazol-1-yl)methyl]-9H-carbazole-2-carboxylic acid | |
| D1 | 9-(3-amino-3-oxo-propyl)-6-(1H-imidazol-1-yl)-2-(2-carboxyethyl)-9H-carbazole | |

| Compound | Structure | HRMS |
|---|---|---|
| E1 | 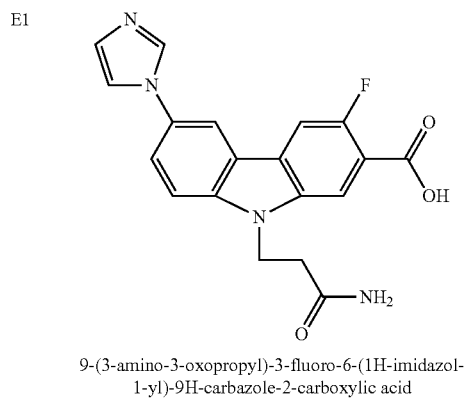 9-(3-amino-3-oxopropyl)-3-fluoro-6-(1H-imidazol-1-yl)-9H-carbazole-2-carboxylic acid | |
| F1 | 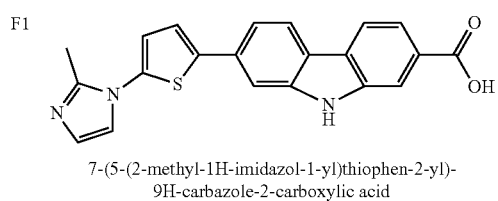 7-(5-(2-methyl-1H-imidazol-1-yl)thiophen-2-yl)-9H-carbazole-2-carboxylic acid | |
| G1 | 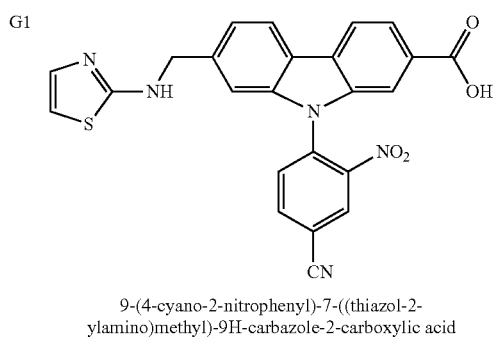 9-(4-cyano-2-nitrophenyl)-7-((thiazol-2-ylamino)methyl)-9H-carbazole-2-carboxylic acid | |
| H1 | 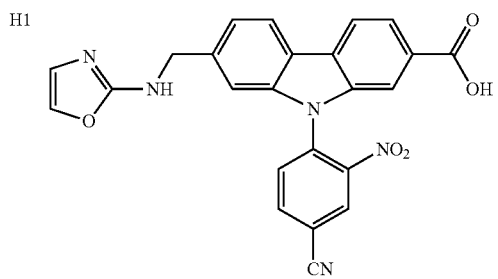 9-(4-cyano-2-nitrophenyl)-7-((oxazol-2-ylamino)methyl)-9H-carbazole-2-carboxylic acid | |
| I1 | 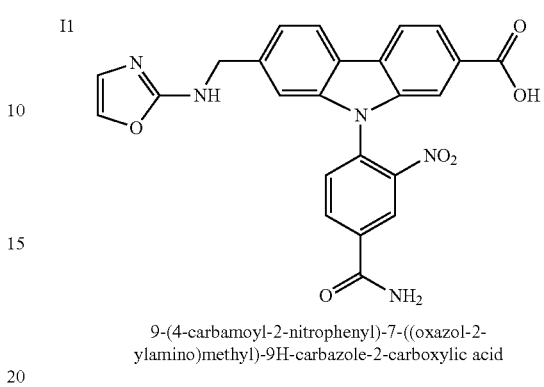 9-(4-carbamoyl-2-nitrophenyl)-7-((oxazol-2-ylamino)methyl)-9H-carbazole-2-carboxylic acid | |
| J1 | 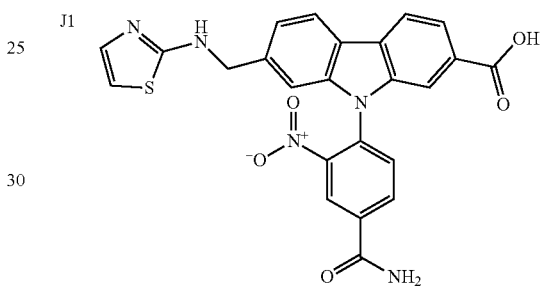 9-(4-carbamoyl-2-nitrophenyl)-7-((thiazol-2-ylamino)methyl)-9H-carbazole-2-carboxylic acid | |
| K1 | 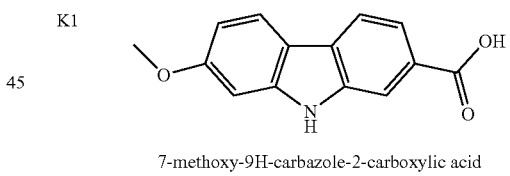 7-methoxy-9H-carbazole-2-carboxylic acid | |
| L1 | 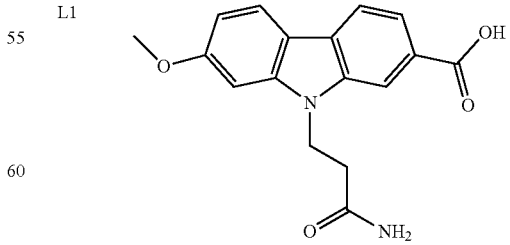 9-(3-amino-3-oxo-propyl)-7-methoxy-9H-carbazole-2-carboxylic acid | |

| Compound | Structure | HRMS |
|---|---|---|
| M1 | 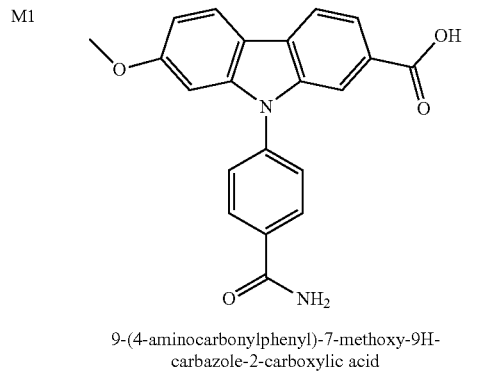 9-(4-aminocarbonylphenyl)-7-methoxy-9H-carbazole-2-carboxylic acid | |
| N1 | 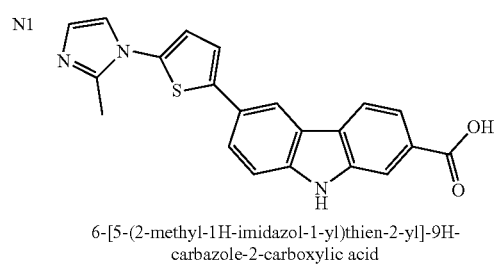 6-[5-(2-methyl-1H-imidazol-1-yl)thien-2-yl]-9H-carbazole-2-carboxylic acid | |
| O1 | 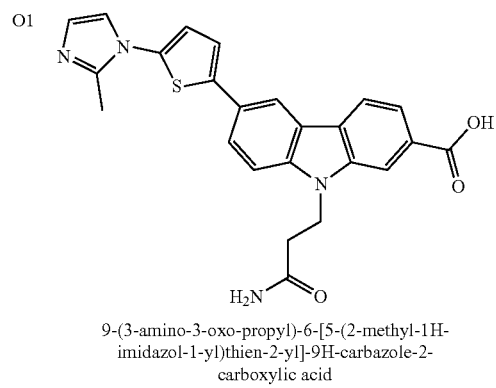 9-(3-amino-3-oxo-propyl)-6-[5-(2-methyl-1H-imidazol-1-yl)thien-2-yl]-9H-carbazole-2-carboxylic acid | |
| P1 | 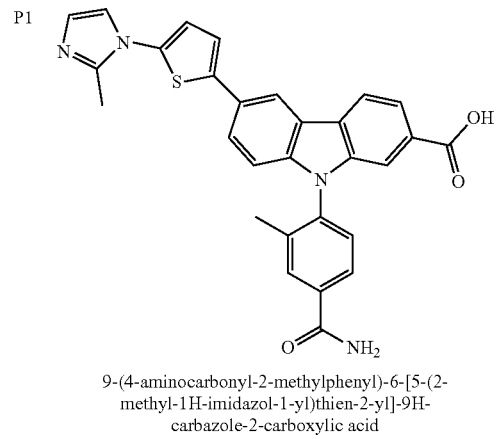 9-(4-aminocarbonyl-2-methylphenyl)-6-[5-(2-methyl-1H-imidazol-1-yl)thien-2-yl]-9H-carbazole-2-carboxylic acid | |
| Q1 | 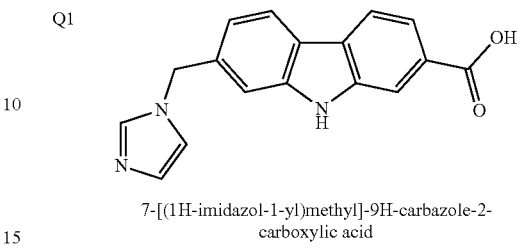 7-[(1H-imidazol-1-yl)methyl]-9H-carbazole-2-carboxylic acid | |
| R1 | 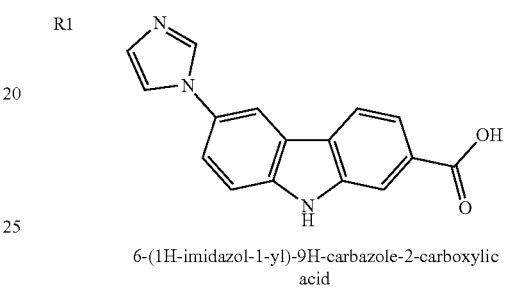 6-(1H-imidazol-1-yl)-9H-carbazole-2-carboxylic acid | |
| S1 | 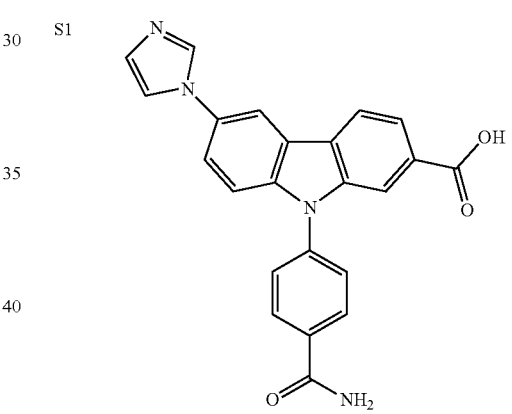 9-(4-aminocarbonylphenyl)-6-(1H-imidazol-1-yl)-9H-carbazole-2-carboxylic acid | |
| T1 | 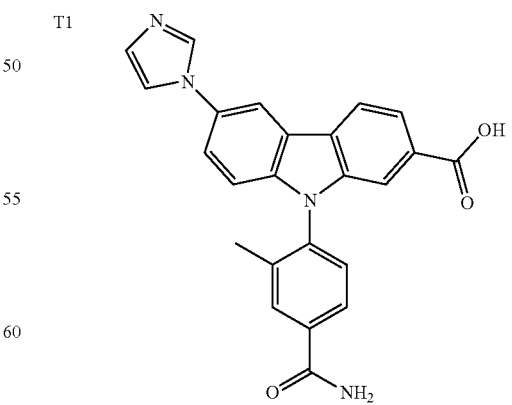 9-(4-aminocarbonyl-2-methylphenyl)-6-(1H-imidazol-1-yl)-9H-carbazole-2-carboxylic acid | |

| Compound | Structure | HRMS |
|---|---|---|
| U1 | 9-(3-amino-3-oxo-propyl)-7-(1H-imidazol-1-yl)-9H-carbazole-2-carboxylic acid | |
| V1 | 9-(4-aminocarbonylphenyl)-7-(1H-imidazol-1-yl)-9H-carbazole-2-carboxylic acid | |
| W1 | 9-(4-aminocarbonyl-2-methylphenyl)-7-(1H-imidazol-1-yl)-9H-carbazole-2-carboxylic acid | |
| A2 | 9-(3-amino-3-oxopropyl)-3-[(1H-imidazol-1-yl)methyl]-9H-carbazole-7-carboxylic acid | |
| B2 | 9-(3-amino-3-oxopropyl)-3-(1H-imidazol-1-yl)-9H-carbazole-7-carboxylic acid | |
| C2 | 9-(4-aminocarbonyl-2-nitrophenyl)-3-[(1H-imidazol-1-yl)methyl]-9H-carbazole-2-carboxylic acid | |
| D2 | 9-(3-amino-3-oxo-propyl)-3-(1H-imidazol-1-yl)-7-(2-carboxyethyl)-9H-carbazole | 377.1616 [M + H]⁺ | or a tautomer, solvate, or pharmaceutically acceptable salt thereof.

Some embodiments provided herein are directed to a compound of formula:

| Compound | Structure | HRMS |
|---|---|---|
| E2 | 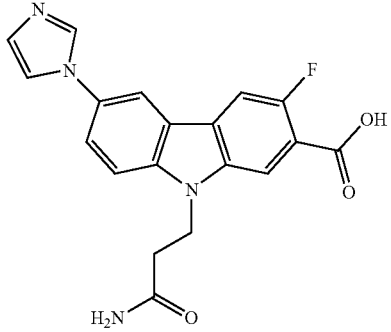 9-(3-amino-3-oxopropyl)-6-fluoro-3-(1H-imidazol-1-yl)-9H-carbazole-7-carboxylic acid | |
| F2 | 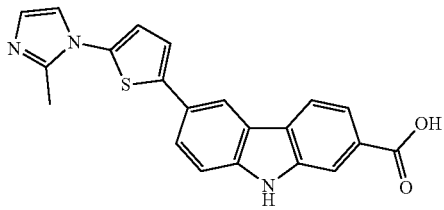 3-(5-(2-methyl-1H-imidazol-1-yl)thiophen-2-yl)-9H-carbazole-7-carboxylic acid or 3-(5-(2-methyl-1H-imidazol-1-yl)thien-2-yl)-9H-carbazole-7-carboxylic acid | |
| G2 | 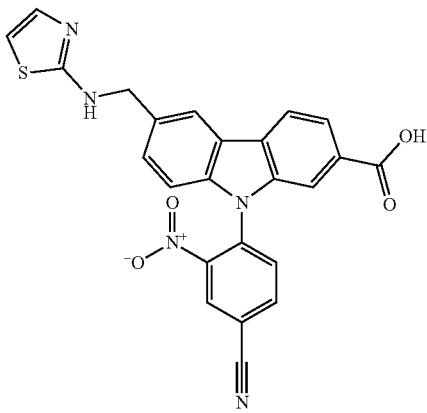 9-(4-cyano-2-nitrophenyl)-3-((thiazol-2-ylamino)methyl)-9H-carbazole-7-carboxylic acid | |
| H2 | 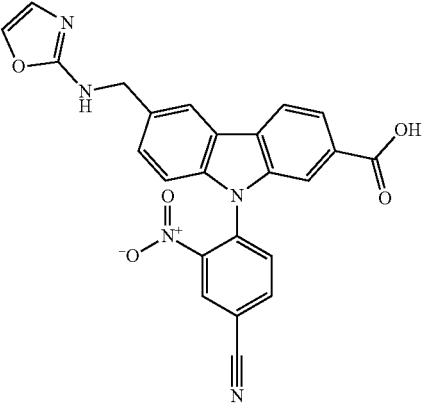 9-(4-cyano-2-nitrophenyl)-3-((oxazol-2-ylamino)methyl)-9H-carbazole-7-carboxylic acid | |
| I2 | 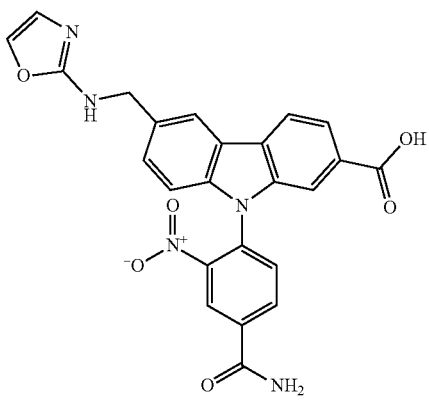 9-(4-carbamoyl-2-nitrophenyl)-3-((oxazol-2-ylamino)methyl)-9H-carbazole-7-carboxylic acid | |
| J2 | 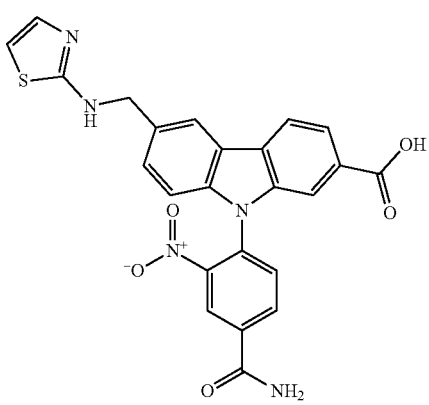 9-(4-carbamoyl-2-nitrophenyl)-3-((thiazol-2-ylamino)methyl)-9H-carbazole-7-carboxylic acid | |

| Compound | Structure | HRMS |
|---|---|---|
| K2 | 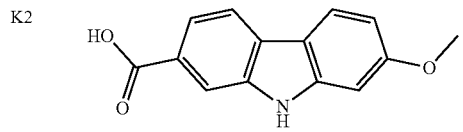 2-methoxy-9H-carbazole 7-carboxylic acid | |
| L2 | 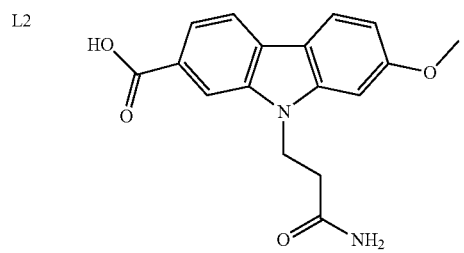 9-(3-amino-3-oxo-propyl)-2-methoxy-9H-carbazole 7-carboxylic acid | |
| M2 | 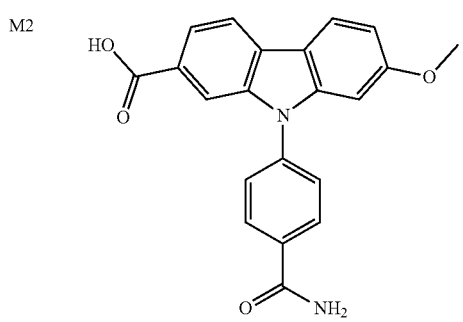 9-(4-aminocarbonylphenyl)-2-methoxy-9H-carbazole 7-carboxylic acid | |
| N2 | 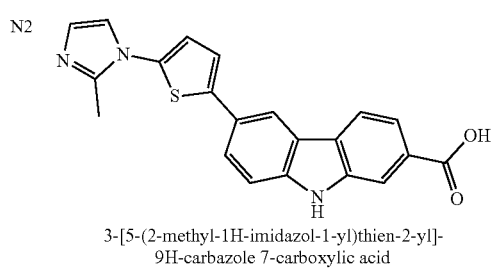 3-[5-(2-methyl-1H-imidazol-1-yl)thien-2-yl]-9H-carbazole 7-carboxylic acid | |
| O2 | 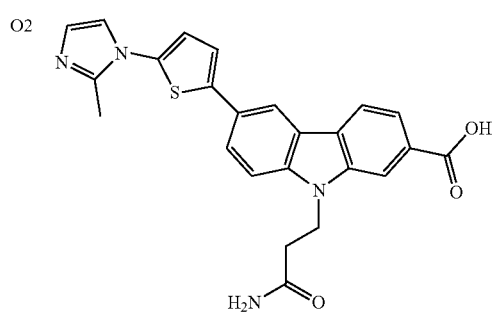 9-(3-amino-3-oxo-propyl)-3-[5-(2-methyl-1H-imidazol-1-yl)thien-2-yl]-9H-carbazole 7-carboxylic acid | |
| P2 | 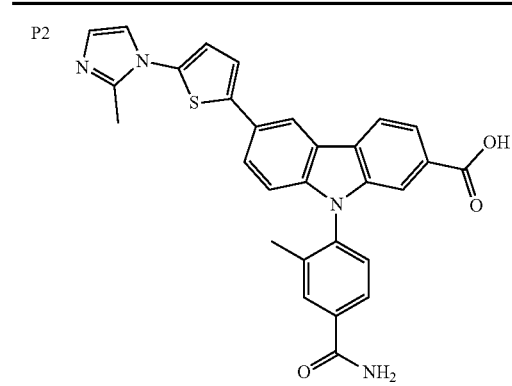 9-(4-aminocarbonyl-2-methylphenyl)-3-[5-(2-methyl-1H-imidazol-1-yl)thien-2-yl]-9H-carbazole 7-caboxylic acid | |
| Q2 | 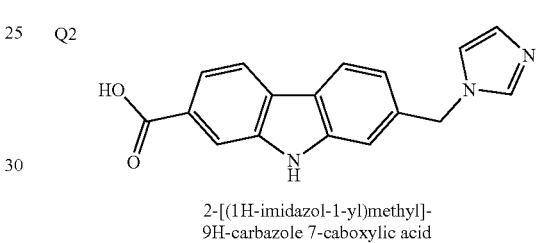 2-[(1H-imidazol-1-yl)methyl]-9H-carbazole 7-caboxylic acid | |
| R2 | 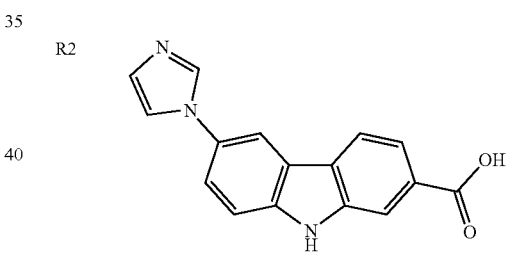 3-(1H-imidazol-1-yl)-9H-carbazole 7-carboxylic acid | |
| S2 | 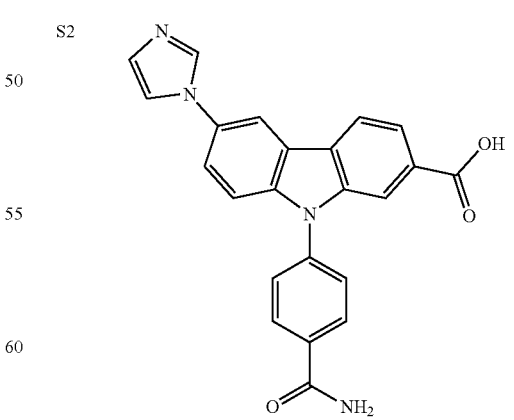 9-(4-aminocarbonylphenyl)-3-(1H-imidazol-1-yl)-9H-carbazole 7-carboxylic acid | |

| Compound | Structure | HRMS |
|---|---|---|
| T2 | 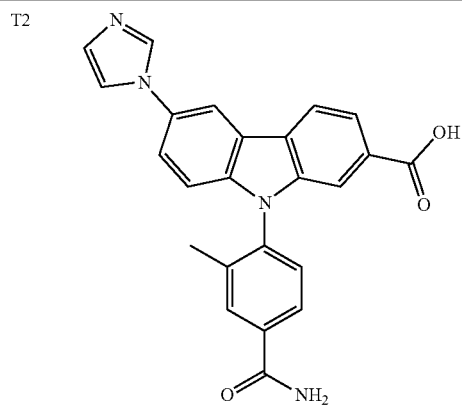 9-(4-aminocarbonyl-2-methylphenyl)-3-(1H-imidazol-1-yl)-9H-carbazole 7-caboxylic acid | |
| U2 | 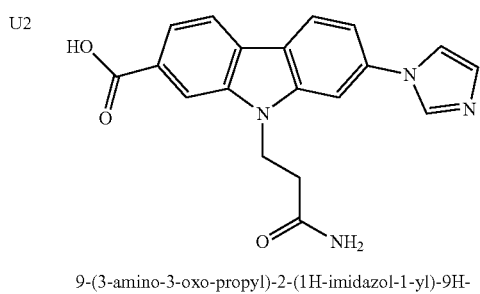 9-(3-amino-3-oxo-propyl)-2-(1H-imidazol-1-yl)-9H-carbazole-7-carboxylic acid | |
| V2 | 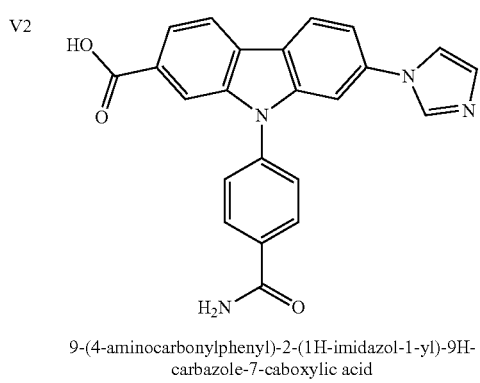 9-(4-aminocarbonylphenyl)-2-(1H-imidazol-1-yl)-9H-carbazole-7-caboxylic acid | |
| W2 | 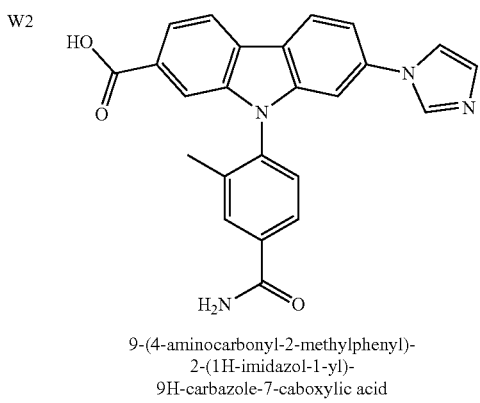 9-(4-aminocarbonyl-2-methylphenyl)-2-(1H-imidazol-1-yl)-9H-carbazole-7-caboxylic acid | | or a tautomer, solvate, or pharmaceutically acceptable salt thereof.

In some embodiments, the present disclosure is directed to compounds disclosed herein and selected from the group consisting of:

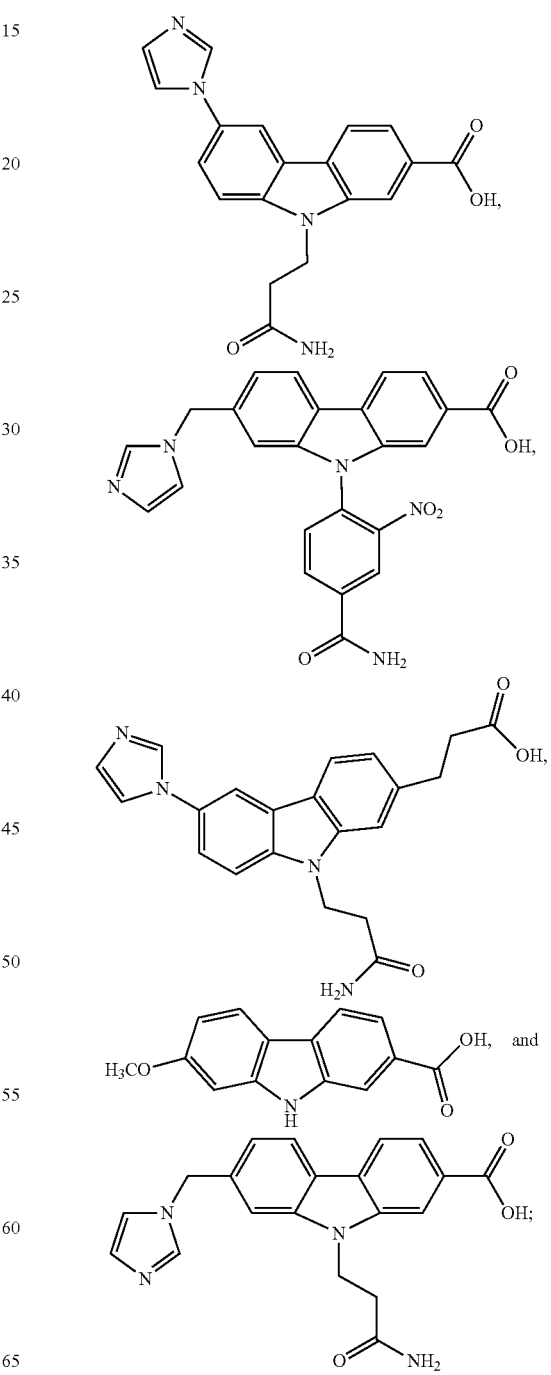

or their tautomers, solvates and/or pharmaceutically acceptable salts thereof.
In some embodiments the compound is:
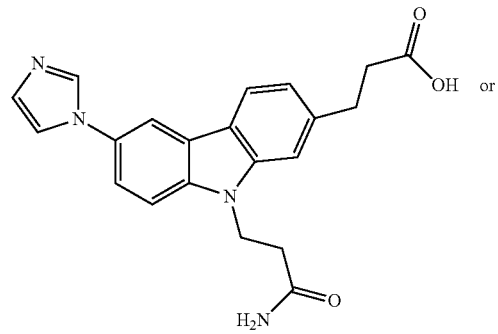 or
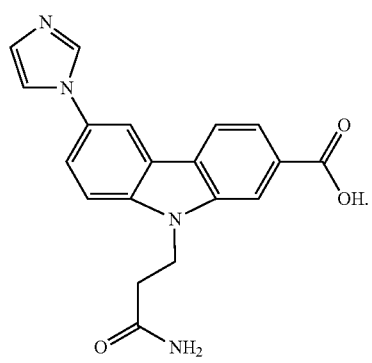
Additional compounds, X, Y, Z, AA, AB, AC, AD, and AE that are included in the scope of this disclosure:
Compounds X, Y and Z
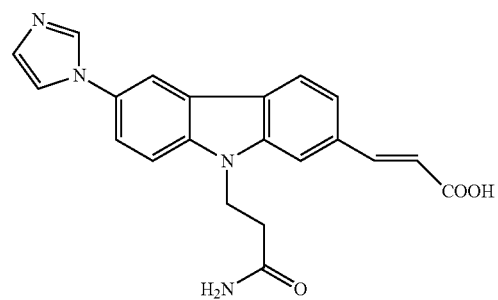
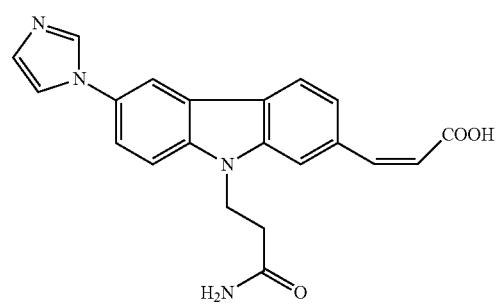
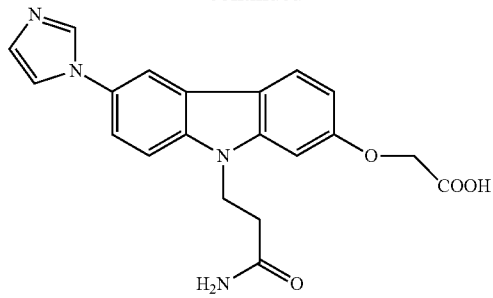
Compounds AA-AE
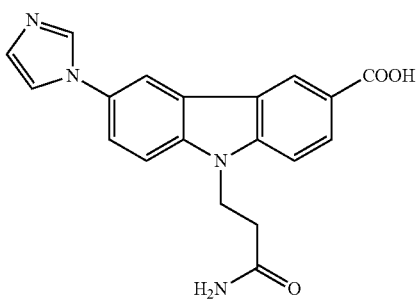
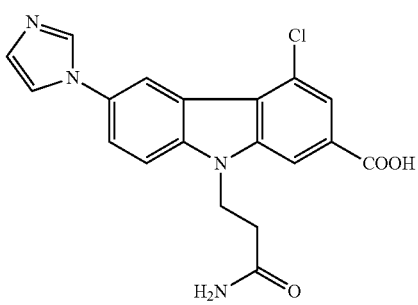
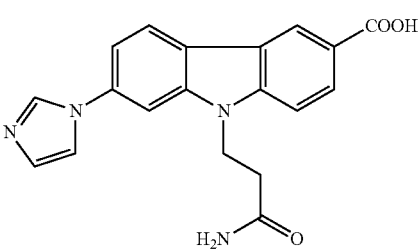
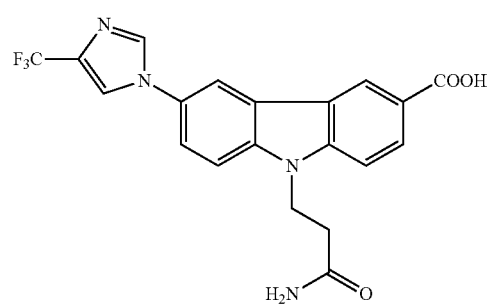

-continued

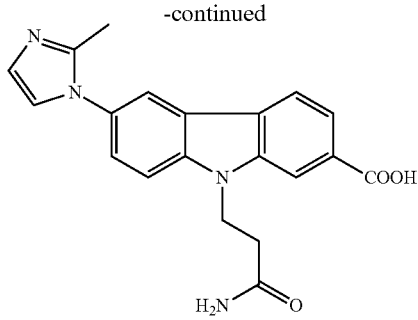

Some embodiments herein provide for a compound selected from the group consisting of:
6-[5-(2-methyl-1H-imidazol-1-yl)thien-2-yl]-9H-carbazole-2-carboxylic acid;
9-(3-amino-3-oxopropyl)-7-[(1H-imidazol-1-yl)methyl]-9H-carbazole-2-carboxylic acid;
9-(3-amino-3-oxopropyl)-6-(1H-imidazol-1-yl)-9H-carbazole-2-carboxylic acid;
9-(4-aminocarbonyl-2-nitrophenyl)-6-[(1H-imidazol-1-yl)methyl]-9H-carbazole-2-carboxylic acid;
9-(3-amino-3-oxo-propyl)-6-(1H-imidazol-1-yl)-2-(2-carboxyethyl)-9H-carbazole;
7-methoxy-9H-carbazole-2-carboxylic acid;
9-(3-amino-3-oxo-propyl)-7-methoxy-9H-carbazole-2-carboxylic acid;
9-(4-aminocarbonylphenyl)-7-methoxy-9H-carbazole-2-carboxylic acid;
9-(3-amino-3-oxo-propyl)-6-[5-(2-methyl-1H-imidazol-1-yl)thien-2-yl]-9H-carbazole-2-carboxylic acid;
9-(4-aminocarbonyl-2-methylphenyl)-6-[5-(2-methyl-1H-imidazol-1-yl)thien-2-yl]-9H-carbazole-2-carboxylic acid;
7-[(1H-imidazol-1-yl)methyl]-9H-carbazole-2-carboxylic acid;
6-(1H-imidazol-1-yl)-9H-carbazole-2-carboxylic acid;
9-(4-aminocarbonylphenyl)-6-(1H-imidazol-1-yl)-9H-carbazole-2-carboxylic acid;
9-(4-aminocarbonyl-2-methylphenyl)-6-(1H-imidazol-1-yl)-9H-carbazole-2-carboxylic acid;
9-(3-amino-3-oxo-propyl)-7-(1H-imidazol-1-yl)-9H-carbazole-2-carboxylic acid;
9-(4-aminocarbonylphenyl)-7-(1H-imidazol-1-yl)-9H-carbazole-2-carboxylic acid;
9-(4-aminocarbonyl-2-methylphenyl)-7-(1H-imidazol-1-yl)-9H-carbazole-2-carboxylic acid;
9-(3-amino-3-oxopropyl)-3-fluoro-6-(1H-imidazol-1-yl)-9H-carbazole-2-carboxylic acid;
7-(5-(2-methyl-1H-imidazol-1-yl)thiophen-2-yl)-9H-carbazole-2-carboxylic acid;
9-(4-cyano-2-nitrophenyl)-7-((thiazol-2-ylamino)methyl)-9H-carbazole-2-carboxylic acid;
9-(4-cyano-2-nitrophenyl)-7-((oxazol-2-ylamino)methyl)-9H-carbazole-2-carboxylic acid;
9-(4-carbamoyl-2-nitrophenyl)-7-((oxazol-2-ylamino)methyl)-9H-carbazole-2-carboxylic acid; and
9-(4-carbamoyl-2-nitrophenyl)-7-((thiazol-2-ylamino)methyl)-9H-carbazole-2-carboxylic acid; or a tautomer, solvate, and/or a pharmaceutically acceptable salt thereof.

In some embodiments, this disclosure is also directed to a pharmaceutical composition comprising one or more compounds disclosed herein and a pharmaceutically acceptable excipient.

In one embodiment, the compounds of the present disclosure, or a pharmaceutical composition comprising said compound or compounds, can be administered in combination with an NO donor. An NO donor donates nitric oxide itself or a related redox active agent and more generally provides activity that is identified with nitric oxide. Examples of S-nitroso compounds, including S-nitrosothiols useful herein, include, S-nitrosoglutathione, S-nitroso-N-acetylpenicillamine, S-nitroso-gamma-thio-L-leucine, S-nitroso-delta-thio-L-leucine, S-nitroso-cysteine and their ethyl esters, S-nitroso-gamma-methyl-L-homocysteine, S-nitroso-L-homocysteine, S-nitrosoalbumin, and S-nitroso cysteinyl glycine. Examples of other NO donors useful herein are carriers including perfluorocarbons that have been saturated with NO or a hydrophobic NO donor, nitroglycerin, isosorbide, sodium nitroprusside, ethyl nitrite, molsidomine, furoxamines, and N-hydroxy(N-nitrosamine). Thus, in one embodiment, the present disclosure provides for a combination of one or more compounds of Formula I or their tautomers, solvates, and/or pharmaceutically acceptable salts thereof with GSNOR inhibitor of R-(+) amlodipine, a known NO releaser.

3. Compositions and Methods

The compounds represented by Formula I or their tautomers and/or pharmaceutically acceptable salts thereof can effectively act as GSNOR inhibitors and treat conditions affected at least in part by increased nitrosylation due to GSNOR inhibition. In one aspect of the present disclosure, there is provided pharmaceutical compositions comprising one or more compounds of Formula I and a pharmaceutically acceptable excipient. In another aspect of this disclosure, there is provided a method for inhibiting GSNOR and/or a method for treating a disease treatable by GSNOR inhibition with an effective amount of one or more compounds of Formula I as provided herein.

In some embodiments, this disclosure provides methods for treating various diseases or disorders that can be treated by inhibiting GSNOR. These include diseases mediated at least in part by pro-inflammatory cytokines, including, but not limited to: IL-4, -5, -6, -10, -12, 13, -17, and -23; and pro-inflammatory chemokines, including, but not limited to: CCL-2 and CCL-11 as well as pro-inflammatory infiltrating cells, including, but not limited to: neutrophils, eosinophils, basophils, lymphocytes, and monocytes (collectively: pro-inflammatory mediators). In one embodiment, the compounds and compositions of this invention are generally applicable toward the treatment of disorders including inhibition of tissue and/or organ inflammation due to pro-inflammatory mediators.

Certain embodiments of this disclosure are directed toward using aromatic nitrogen-containing compounds, such as those described herein, to treat conditions in a subject which include those mediated at least in part by over-expression of pro-inflammatory mediators. Accordingly, in one embodiment, this disclosure is directed toward methods of alleviating or ameliorating a condition or disorder, mediated at least in part by GSNOR, including conditions arising from over-expression of pro-inflammatory mediators.

In one embodiment, provided is a method for treating a disease or disorder mediated at least in part by expression or over-expression of GSNOR and which may be treated by inhibition of GSNOR, where the method involves administering to a subject an effective amount of one or more compounds of Formula I or a pharmaceutical composition comprising a pharmaceutically acceptable excipient and an effective amount of one or more compounds of Formula I.

The compounds of the present disclosure are useful in inhibiting GSNOR and/or treating disorders relating to over-expression of IL-6. In some embodiments, compounds of the present disclosure are useful in inhibiting GSNOR and/or treating disorders relating to over-expression of IL-17. In some embodiments, compounds of the present disclosure are useful in inhibiting GSNOR and/or treating disorders relating to over-expression of IL-23. In some embodiments, compounds of the present disclosure are useful in inhibiting GSNOR and/or treating disorders relating to over-expression of IL6, IL-17, or IL-23.

In one of its method aspects, this disclosure is directed to a method for inhibiting GSNOR which method comprises contacting GSNOR containing cells (including neurons/microglia/invading macrophages) with an effective amount of one or more compounds of Formula I as described herein.

In an aspect, there is provided a method for inhibiting GSNOR wherein the method comprises contacting cells either in vivo or in vitro with an effective amount of one or more compounds of Formula I.

In another aspect, there is provided a method for prophylactic therapy or treatment of a subject having a disorder treatable by GSNOR inhibition wherein said method comprising administering an effective amount of one or more compounds of Formula I to the subject in need thereof.

In another aspect, a method for increasing protein nitrosylation is provided wherein the method comprises contacting cells with an effective amount of one or more compounds of Formula I disclosed herein under conditions wherein GSNOR inhibition results in increased protein nitrosylation. In one aspect, the method for increasing protein nitrosylation is performed in vitro or in vivo.

In some embodiments, this disclosure is directed to a method for treating pro-inflammatory mediators related condition selected from the group consisting of respiratory, cardiovascular, oncologic, aging, metabolic, renal, hepatic, cutaneous, autoimmune, oxidant based, inflammatory, fibrotic, and inflammatory bowel diseases, wherein which method comprises administering to a subject an effective amount of one or more compounds of Formula I to a subject in need thereof.

Some embodiments provide for a method for treating an IL-6, IL-17, or IL-23 related condition in a subject in need thereof, wherein the method comprises administering to a subject an effective amount of a compound described herein, and the condition is selected from the group consisting of respiratory, cardiovascular, oncologic, aging, metabolic, renal, hepatic, cutaneous, autoimmune, oxidant based, inflammatory, fibrotic, and inflammatory bowel diseases. In some embodiments, this disclosure is directed to a method for treating an IL-6 related condition selected from the group consisting of respiratory, cardiovascular, oncologic, aging, metabolic, renal, hepatic, cutaneous, autoimmune, oxidant based, inflammatory, fibrotic, and inflammatory bowel diseases, wherein which method comprises administering to a subject an effective amount of one or more compounds of Formula I to a subject in need thereof. Some embodiments provide for a method for treating an IL-17 related condition in a subject in need thereof, wherein the method comprises administering to a subject an effective amount of a compound described herein, and the condition is selected from the group consisting of respiratory, cardiovascular, oncologic, aging, metabolic, renal, hepatic, cutaneous, autoimmune, oxidant based, inflammatory, fibrotic, and inflammatory bowel diseases. Some embodiments provide for a method for treating an IL-23 related condition in a subject in need thereof, wherein the method comprises administering to a subject an effective amount of a compound described herein, and the condition is selected from the group consisting of respiratory, cardiovascular, oncologic, aging, metabolic, renal, hepatic, cutaneous, autoimmune, oxidant based, inflammatory, fibrotic, and inflammatory bowel diseases.

In some embodiments, this disclosure is directed to a method for treating a condition treatable by GSNOR inhibition, which condition is due to radiation toxicity. Radiation toxicity induces over-expression of IL-6, IL-17, and IL-23. Accordingly, inhibition of GSNOR results in inhibition of IL-6, IL-17, and IL-23 over-expression. Such methods can be administered in a therapeutic or a prophylactic setting for subjects undergoing radiation therapy or for soldiers or other first responders at risk of or already exposed to toxic levels of radiation. The method comprises administering of one or more compounds of Formula I to a subject in need thereof in order to reduce the level of IL-6 induced by the radiation. In some embodiments, provided herein are methods comprising administering of a compound as described herein to a subject in need thereof in order to reduce the level of IL-6, IL-17, or IL-23 induced by the radiation. In some embodiments, the method comprises administering one or more compounds of Formula I to a subject in need thereof in order to reduce the level of pro-inflammatory mediators induced by the radiation. In one embodiment, the condition is radiation proctitis, radiation colitis, radiation fibrosis, radiation dermatitis, or pulmonary radiation injury.

In another aspect, this disclosure is also directed to a method wherein one or more compounds of Formula I may be administered with other GSNOR inhibitor agents, such as anti-GSNOR antibodies or antibody fragments, GSNOR antisense, iRNA, or other small molecule GSNOR inhibitors, or in combination with other agents as described in detail herein.

Diseases and/or disorders affected at least in part by GSNOR inhibition of IL-6 production include those selected from the group consisting of asthma, exercise induced asthma, COPD, idiopathic pulmonary fibrosis, lung injury due to cystic fibrosis, type I and II diabetes, atherosclerosis, ischemic heart disease, myocardial infarction, myocarditis, endocarditis, coronary artery disease, heart failure, ischemia reperfusion injury, septic shock, toxic shock syndrome, pulmonary arterial hypertension, coronary artery re-stenosis, cardiomyopathy, congestive heart failure, arrhythmia, peripheral arterial disease, sickle cell anemia, embolic disease, cerebrovascular accidents, rheumatoid arthritis, osteoarthritis, atherosclerosis, multiple sclerosis, inflammatory bowel disease, Crohn's disease, ulcerative colitis, chronic kidney disease, autoimmune diseases, glomerulonephritis, psoriasis, cutaneous lupus erythematosus, systemic lupus erythematosus, systemic sclerosis, dermatitis, acne, atopic dermatitis, radiation dermatitis, radiation proctitis, ischemic stroke, traumatic brain injury, seizure, Alzheimer's disease, Parkinson's disease, Myasthenia gravis, chronic pain, aging and diseases of aging, alcoholic liver disease, liver cirrhosis, liver fibrosis, Fatty Liver Disease (Non-Alcoholic Fatty Liver Disease—NAFLD), hepatitis, and primary sclerosing cholangitis (PSC), and/or complications thereof.

In some embodiments, provided is a method for treating a disease or disorder affected at least in part by GSNOR inhibition of IL-6, IL-17, or IL-23 production comprising administering a therapeutically effective amount of a compound as described herein. In some embodiments, such a disease or disorder affected at least in part by GSNOR inhibition of IL-6, IL-17, or IL-23 production is asthma, exercise induced asthma, COPD, idiopathic pulmonary fibrosis, lung injury due to cystic fibrosis, type I and II diabetes, atherosclerosis, ischemic heart disease, myocardial infarction, myocarditis, endocarditis, coronary artery disease, heart failure, ischemia reperfusion injury, septic shock, toxic shock syndrome, pulmonary arterial hypertension, coronary artery re-stenosis, cardiomyopathy, congestive heart failure, arrhythmia, peripheral arterial disease, sickle cell anemia, embolic disease, cerebrovascular accidents, rheumatoid arthritis, osteoarthritis, atherosclerosis, multiple sclerosis, inflammatory bowel disease, Crohn's disease, ulcerative colitis, chronic kidney disease, autoimmune diseases, glomerulonephritis, psoriasis, cutaneous lupus erythematosus, systemic lupus erythematosus, systemic sclerosis, dermatitis, acne, atopic dermatitis, radiation dermatitis, radiation proctitis, ischemic stroke, traumatic brain injury, seizure Alzheimer's disease, Parkinson's disease, Myasthenia gravis, chronic pain, aging and diseases of aging, alcoholic liver disease, liver cirrhosis, liver fibrosis, Fatty Liver Disease (Non-Alcoholic Fatty Liver Disease—NAFLD), non-alchoholic steatohepatitis (NASH), hepatitis, or primary sclerosing cholangitis (PSC), or complications thereof.

In some embodiments, provided is a method for treating NASH in a subject in need thereof, comprising administering a therapeutically effective amount of a compound as described herein. In some embodiments, mitigation of the symptoms and conditions of NASH are achieved by administration of one or more compounds described herein.

In some embodiments, a compound as described herein is administered with another therapeutic agent used to reduce one or more of the symptoms of NASH including, but not limited to, an agent used to control blood glucose levels, an agent used to control lipid levels, e.g., an agent used to lower control cholesterol, an antioxidant, an appetite suppressing agent, an anti-obesity agent an antibiotic or an anti-inflammatory agent. Non-limiting examples of such agents include an agent used to control blood glucose levels, such as, sulfonylureas, such as, chlorpropamide (brand name Diabinese), glipizide (brand names Glucotrol and Glucotrol XL), glyburide (brand name Micronase, Glynase, and Diabeta), and glimepiride (Amaryl); meglitinides, such as, repaglinide (brand name Prandin) and nateglinide (brand name Starlix); biguanides, such as, metformin (brand name Glucophage®) and acarbose (Precose); thiazolidinediones, such as, rosiglitazone (brand name Avandia®), troglitazone (brand name Rezulin®), and pioglitazone (brand name Actos®); alpha-glucosidase inhibitors, such as, acarbose (brand name Precose®) and meglitol (brand name Glyset); and insulin, such as, pramlintide (brand name Symlin), exenatide (brand name Byetta), humalog (brand name Lispro), novolog (brand name Aspart), humulin, novolin, ultralente, and lantus (brand name Glargine); an agent used to control lipid levels, such as, vytorin, LXR agonists, Clofibrate and Gemfibrozil, a plasma HDL-raising agent, a cholesterol lowering agent, such as, ursodeoxycholic acid (a synthetic bile salt Actigall®, URSO®, or Ursodiol®), a cholesterol biosynthesis inhibitor, for example an HMG-CoA reductase inhibitor (such as a statin, such as, Atorvastatin (Lipitor) Fluvastatin (Lescol) Lovastatin (Altocor, Mevacor) Pravastatin (Pravachol) Rosuvastatin (Crestor) Simvastatin (Zocor) and rosuvastatin calcium), an HMG-CoA synthase inhibitor, a squalene epoxidase inhibitor, or a squalene synthetase inhibitor (also known as squalene synthase inhibitor), an acyl-coenzyme A: cholesterol acyltransferase (ACAT) inhibitor, such as, melinamide; probucol, niacin (nicotinic acid, Vitamin-B-3), nicotinic acid and the salts thereof and niacinamide; a cholesterol absorption inhibitor such as beta-sitosterol, and exetimibe (Zatia), a bile acid sequestrant, such as, cholestyramine (Questran), colestipol (Colestid), and Colesevelam (WelChol), or a dialkylaminoalkyl derivatives of a cross-linked dextran; and LDL (low density lipoprotein) receptor inducer, fibrates such as clofibrate, fenofibrate, and gemfibrizol, vitamin $B_6$ (also known as pyridoxine) and physiologically acceptable salts thereof, such as the HCl salt; vitamin $B_{12}$ (also known as cyanocobalamin), and angiotensin II antagonist converting enzyme inhibitor; and a platelet aggregation inhibitor, such as fibrinogen receptor antagonists (i.e., glycoprotein IIb/IIIa fibrinogen receptor antagonists); an antibiotic, such as, Polymixin B; and an antioxidant, such as, selenium, betaine, vitamin C, vitamin E and beta carotene: a beta-blocker; an agent used to reduce weight or suppress appetite, such as, sibutramine (Meridia), orlistat, (Xenical), anorectics (Anorexigenics), dexedrine, digoxin, cannabinoid (CB 1) receptor antagonists, rimonabant, amphetamines, lipase inhibitors, bupropion, topiramate, zonisamide, fenfluramine, phentermine (Adipex-P, Fastin, lonamin, Oby-trim, Pro-Fast, Zantryl), phendimetrazine (Bontril, Plegine, Prelu-2, X-Trozine, Adipost), diethylpropion (Tenuate, Tenuate dospan), fluoxetine/phentermine, phendimetrazine/phentermine, and orlistat/sibutramine. In some embodiments, the another therapeutic agent is Obeticholic acid. In some embodiments, the another therapeutic agent is Elafibranor.

In one embodiment, the therapeutically effective amount is a specific amount which causes a specific physiological effect which results in the amelioration of the disorder being treated or protects against a risk associated with the disorder. For example, for asthma, a therapeutically effective amount is a bronchodilating effective amount; for cystic fibrosis, a therapeutically effective amount is an airway obstruction ameliorating effective amount; for ARDS, a therapeutically effective amount is a hypoxemia ameliorating effective amount; for heart disease, a therapeutically effective amount is an angina relieving or angiogenesis inducing effective amount; for hypertension, a therapeutically effective amount is a blood pressure reducing effective amount; for ischemic coronary disorders, a therapeutic amount is a blood flow increasing effective amount; for atherosclerosis, a therapeutically effective amount is an endothelial dysfunction reversing effective amount; for an autoimmune disease, a therapeutic amount is an autoimmune reducing effective amount; for diseases characterized by angiogenesis, a therapeutically effective amount is an angiogenesis inhibiting effective amount; for disorders where there is risk of thrombosis occurring, a therapeutically effective amount is a thrombosis preventing effective amount; for disorders where there is risk of restenosis occurring, a therapeutically effective amount is a restenosis inhibiting effective amount; for chronic inflammatory diseases, a therapeutically effective amount is an inflammation reducing effective amount; for disorders where there is risk of apoptosis occurring, a therapeutically effective amount is an apoptosis preventing effective amount; for impotence, a therapeutically effective is an erection attaining or sustaining effective amount; for obesity, a therapeutically effective amount is a satiety causing effective amount; for stroke, a therapeutically effective amount is a blood flow increasing or a TIA protecting effective amount; for reperfusion injury, a therapeutically effective amount is a function increasing effective amount; and for preconditioning of heart and brain, a therapeutically effective amount is a cell protective effective amount, e.g., as measured by triponin or CPK.

The compounds of this disclosure are also useful in the diagnosis and treatment of a variety of human diseases selected from the group consisting of type I and II diabetes, oncologic diseases and disorders, atherosclerosis, hypertension, ischemic heart disease, myocardial infarction, myocarditis, endocarditis, congenital heart disease, rheumatic heart disease, heart valvular disease, coronary artery disease, heart failure, cardiogenic shock, ischemia reperfusion injury, septic shock, toxic shock syndrome, pulmonary arterial hypertension, coronary artery re-stenosis, cardiomyopathy, congestive heart failure, arrhythmia, peripheral arterial disease, sickle cell anemia, embolic disease, and cerebrovascular accidents. For example, the compounds of this disclosure are particularly useful in treating disorders arising from oxidative stress and complications thereof.

In another aspect, this disclosure is directed to a method wherein one or more compounds of Formula I which are used as a means to improve ß-adrenergic signaling. In particular, inhibitors of GSNOR alone or in combination with ß-agonists could be used to treat or protect against heart failure, or other vascular disorders such as hypertension and asthma. GSNOR inhibitors can also be used to modulate G protein coupled receptors (GPCRs) by potentiating Gs G-protein, leading to smooth muscle relaxation (e.g., airway and blood vessels), and by attenuating Gq G-protein, and thereby preventing smooth muscle contraction (e.g., in airway and blood vessels). GSNOR inhibitors have been shown to activate soluble guanylate cyclase to increase the signaling molecule, cyclic GMP.

In some embodiments, provided herein are methods of treating a fibrotic disease in a subject in need thereof, comprising administering to the subject a therapeutically effective amount of a compound described herein. In some embodiments, the fibrotic disease is pulmonary fibrosis, cystic fibrosis, idiopathic pulmonary fibrosis, radiation-induced lung injury following treatment for cancer, liver cirrhosis, biliary atresia, NASH, atrial fibrosis, endomyocardial fibrosis, old myocardial infarction fibrosis, brain glial scar, arterial stiffness, arthrofibrosis (knee, shoulder, other joints), Crohn's Disease, Dupuytren's contracture, keloid, mediastinal fibrosis, myelofibrosis, Peyronie's disease, nephrogenic systemic fibrosis, progressive massive lung fibrosis, coal workers' pneumoconiosis, retroperitoneal fibrosis, scleroderma/systemic sclerosis, or shoulder adhesive capsulitis.

In some embodiments, provided herein are methods of treating an autoimmune disease in a subject in need thereof, comprising administering to the subject a therapeutically effective amount of a compound described herein. In some embodiments, the autoimmune disease is acute disseminated encephalomyelitis, acute motor axonal neuropathy, Addison's disease, adiposis dolorosa, Adult-onset Still's disease, alopecia areata, ankylosing spondylitis, Anti-Glomerular Basement Membrane nephritis, anti-neutrophil cytoplasmic antibody-associated vasculitis, Anti-N-Methyl-D-Aspartate Receptor Encephalitis, antiphospholipid syndrome, anti synthetase syndrome, aplastic anemiam, Autoimmune Angioedema, autoimmune enteropathy, autoimmune hemolytic anemia, autoimmune hepatitis, autoimmune inner ear disease, autoimmune lymphoproliferative syndrome, autoimmune neutropenia, autoimmune oophoritis, autoimmune orchitis, autoimmune pancreatitis, autoimmune polyendocrine syndrome, autoimmune polyendocrine syndrome type 2, autoimmune polyendocrine syndrome type 3, autoimmune progesterone dermatitis, autoimmune retinopathy, autoimmune thrombocytopenic purpura, autoimmune thyroiditis, autoimmune urticaria, autoimmune uveitis, Balo concentric sclerosis Behçet's disease, Bickerstaff's encephalitis, bullous pemphigoid, Celiac disease, chronic fatigue syndrome, chronic inflammatory demyelinating polyneuropathy, Churg-Strauss syndrome, cicatricial pemphigoid, cogan syndrome, cold agglutinin disease, complex regional pain syndrome, CREST syndrome, Crohn's disease, dermatitis herpetiformis, dermatomyositis, diabetes mellitus type 1, discoid lupus erythematosus, endometriosis, enthesitis, enthesitis-related arthritis, eosinophilic esophagitis, eosinophilic fasciitis, epidermolysis bullosa acquisita, erythema nodosum, essential mixed cryoglobulinemia, Evans syndrome, Felty syndrome, fibromyalgia, gastritis, Gestational pemphigoid, Giant cell arteritis, goodpasture syndrome Graves' disease, Graves ophthalmopathy, Guillain-Barré syndrome, Hashimoto's Encephalopathy, Hashimoto Thyroiditis, Henoch-Schonlein purpura, Hidradenitis suppurativa, Idiopathic inflammatory demyelinating diseases, IgG4-related systemic disease, inclusion body myositis, Inflamatory Bowel Disease (IBD), intermediate uveitis, interstitial cystitis, Juvenile Arthritis, Kawasaki's disease, Lambert-Eaton myasthenic syndrome, leukocytoclastic vasculitis, lichen planus, lichen sclerosus, ligneous conjunctivitis, linear IgA disease, lupus nephritis, lupus vasculitis, Lyme disease (Chronic), Ménière's disease, microscopic colitis, microscopic polyangiitis, Mixed connective tissue disease, Mooren's ulcer, Morphea, Mucha-Habermann disease, multiple sclerosis, myasthenia gravis, myocarditis, myositis, neuromyelitis optica, neuromyotonia, opsoclonus myoclonus syndrome, optic neuritis, Ord's thyroiditis, palindromic rheumatism, paraneoplastic cerebellar degeneration, Parry Romberg syndrome, Parsonage-Turner syndrome, Pediatric Autoimmune Neuropsychiatric Disorder Associated with *Streptococcus, Pemphigus vulgaris, Perniciosus anemia, Pityriasis lichenoides* et *varioliformis acuta*, POEMS syndrome, *polyarteritis nodosa*, polymyalgia rheumatica, polymyositis, postmyocardial infarction syndrome, postpericardiotomy syndrome, primary biliary cirrhosis, primary immunodeficiency, primary sclerosing cholangitis, progressive inflammatory neuropathy, psoriasis, psoriatic arthritis, pure red cell aplasia, pyoderma gangrenosum, Raynaud phenomenon, reactive arthritis, relapsing polychondritis, restless leg syndrome, retroperitoneal fibrosis, rheumatic fever, rheumatoid arthritis, rheumatoid vasculitis, Sarcoidosis, Schnitzler syndrome, scleroderma, Sjogren's syndrome, Stiff person syndrome, Subacute bacterial endocarditis, Susac's syndrome, Sydenham chorea, Sympathetic ophthalmia, Systemic Lupus Erythematosus, Systemic scleroderma, thrombocytopenia, Tolosa-Hunt syndrome, transverse myelitis, ulcerative colitis, undifferentiated connective tissue disease, urticaria, urticarial vasculitis, vasculitis, or vitiligo.

In some embodiments, provided herein are methods of treating an inflammatory disease in a subject in need thereof, comprising administering to the subject a therapeutically effective amount of a compound described herein. In some embodiments, the inflammatory disease is Alzheimer's, ankylosing spondylitis, arthritis (including but not limited to osteoarthritis, rheumatoid arthritis ("RA"), and psoriatic arthritis), psoriasis, asthma, atherosclerosis, Crohn's disease, colitis, atopic dermatitis, diverticulitis, fibromyalgia, hepatitis, NASH, irritable bowel syndrome (IBS), systemic lupus erythematous (SLE), nephritis, Parkinson's disease, ulcerative colitis, endometriosis, preeclampsia, acne vulgaris, acne vulgaris, asthma, an autoimmune disease, Celiac disease, chronic prostatitis, diverticulitis, glomerulonephritis, hidradenitis suppurativa, hypersensitivities, inflammatory bowel disease, interstitial cystitis, lichen planus, Mast Cell Activation Syndrome, mastocytosis, otitis, pelvic inflammatory disease, reperfusion injury, rheumatic fever, rhinitis, sarcoidosis, transplant rejection, vasculitis, uterine fibroids, or eosinophilic esophagitis.

Certain compounds of this disclosure are shown to have improved safety and potency, such as the potency of inhibiting GSNOR at nanomolar concentrations. In general, compounds of this disclosure are shown to have potency, ameliorate, and/or possess efficacy in treating diseases or disorders which include, as a component, some form of oxidative stress.

The amount of active compound administered will vary depending upon the disease treated, the mammalian species, and the particular mode of administration, the age, weight and severity of the disease and other factors well known to the attending clinician. Suitable doses for the compounds of this disclosure can be, for example, between 0.1 mg to about 1000 mg, between 1 mg to about 500 mg, between 1 mg to about 300 mg, or between 1 mg to about 100 mg per day. Such doses can be administered once a day or more than once a day, for example 2, 3, 4, 5 or 6 times a day, but preferably 1 or 2 times per day. In some embodiments, the total dosage for a 70 kg adult is in the range of 0.001 to about 15 mg per kg weight of subject per administration or 0.01 to about 1.5 mg per kg weight of subject per administration, and such therapy can extend for a number of days, a number of weeks or months, and in some cases, years. It will be understood, however, that the specific dose level for any particular subject will depend on a variety of factors including the activity of the specific compound employed; the age, body weight, general health, sex, and diet of the individual being treated; the time and route of administration; the rate of excretion; other drugs that have previously been administered; and the severity of the particular disease undergoing therapy, as is well understood by those of skill in the area.

4. General Synthetic Methods

The compounds of this disclosure can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and P. G. M. Wuts, *Protecting Groups in Organic Synthesis*, Third Edition, Wiley, New York, 1999, and references cited therein.

If the compounds of this disclosure contain one or more chiral centers, such compounds can be prepared or isolated as pure stereoisomers, i.e., as individual enantiomers or d(l) stereomers, or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989), Organic Reactions, Volumes 1-40 (John Wiley, and Sons, 1991), March's Advanced Organic Chemistry, (John Wiley, and Sons, $5^{th}$ Edition, 2001), and Larock's Comprehensive Organic Transformations (VCH Publishers Inc., 1989).

Synthesis of Representative Compounds of the Disclosure

In one general embodiment, the method involves reacting an appropriate nitro-aryl compound as starting material with an appropriate aryl boronic acid coupling partner and palladium to give an 2-nitro-1,1'-biphenyl adduct (Suzuki reaction) which is then heated in the presence of excess triphenylphosphine in order to make the corresponding carbazole. It is appreciated that the nitro-aryl component may be coupled to other suitable aryl compounds by a variety of methods or reactions including Ullmann, Stille, Negishi, Heck, Sonogashira, Gomberg-Bachmann, and Kumada coupling.

Additionally, it is noted that the skilled artisan will appreciate these carbazole compounds are also made by other synthetic strategies which employ differing starting compounds possessing differing functional groups. For instance, carbazoles can be made by a Graebe-Ullmann reaction using N-phenyl-1,2-diaminobenzenes, by nitrene insertion reactions using 2-nitro-1,1'-biaryl compounds or by a Bucherer reaction using aryl hydrazines and phenol. In any event, the isolated carbazole compounds can then be functionalized further with additional reaction steps.

In another general embodiment, the method involves reacting an appropriately functionalized carbazole compound, as synthesized from above, with an electrophilic partner under electrophilic substitution reaction conditions. In another general embodiment, the method involves reacting an appropriately functionalized carbazole compound, as synthesized from above, with an nucleophilic partner under nucleophilic substitution reaction conditions. It is further appreciated that the electrophilic or nucleophilic partner selectively reacts with one functional group of the carbazole compound. Thus, the reactants should not be added under any reaction conditions in which that reactant might react with any other functional group.

For example, the compounds of disclosed herein can be generally prepared according to representative Scheme 1:

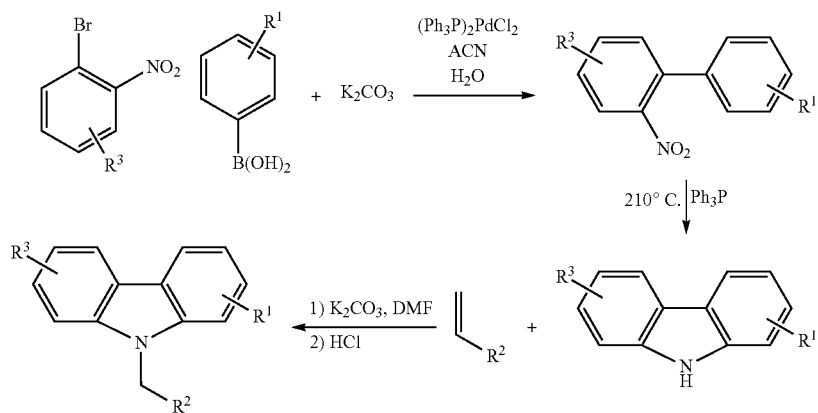
As appropriate, amino, keto, hydroxyl, and any other necessary protecting groups and their methods of deprotection are known in the art, such as those described in T. W. Greene and P. G. M. Wuts, *Protecting Groups in Organic Synthesis*, Third Edition, Wiley, New York, 1999.
In another example, the compound 10 in the Table 1 was prepared according to Scheme 2:
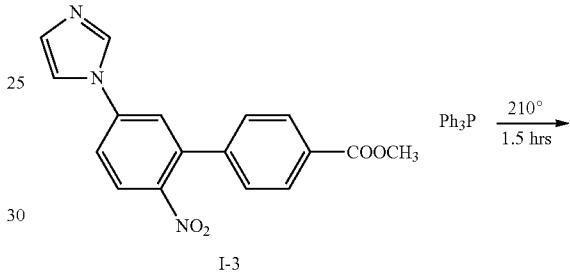
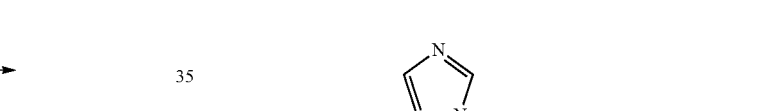
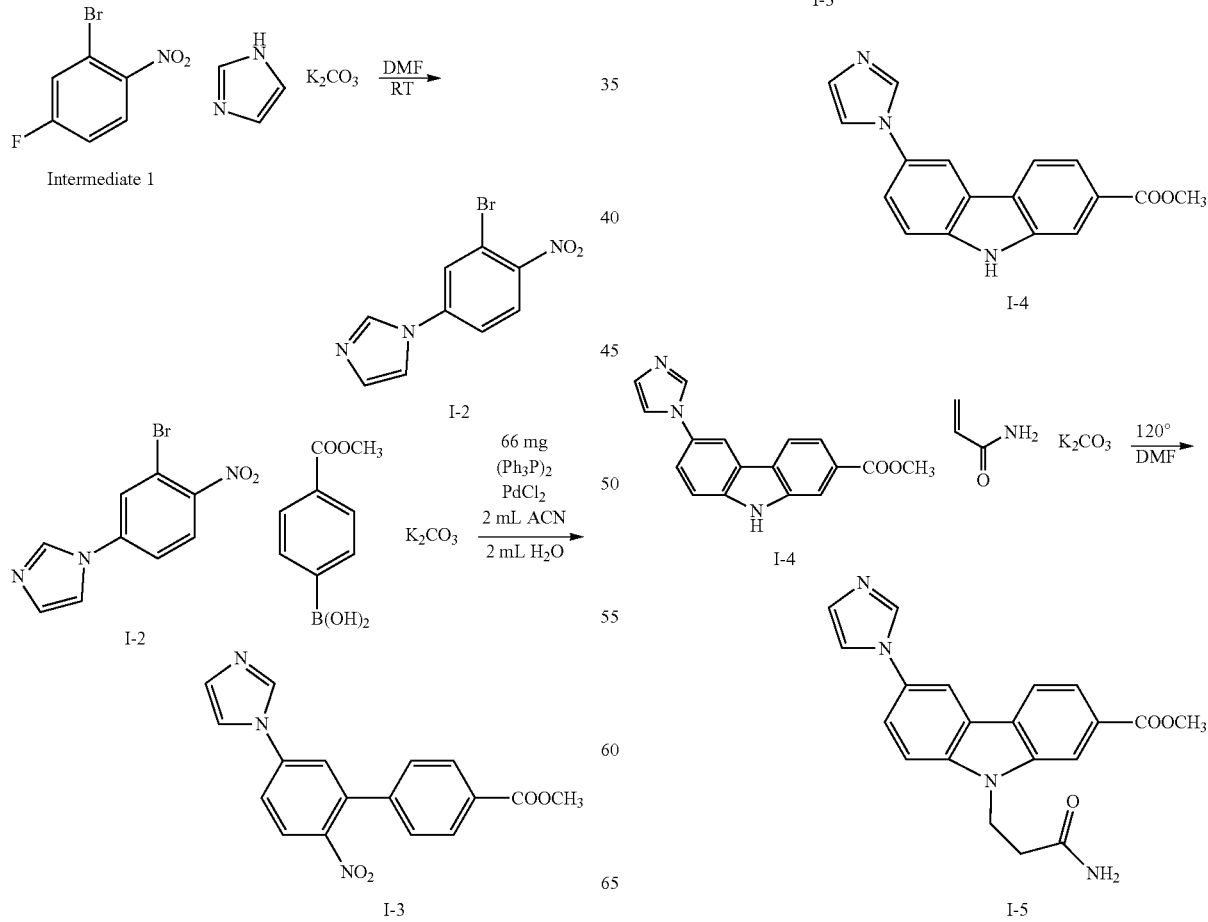

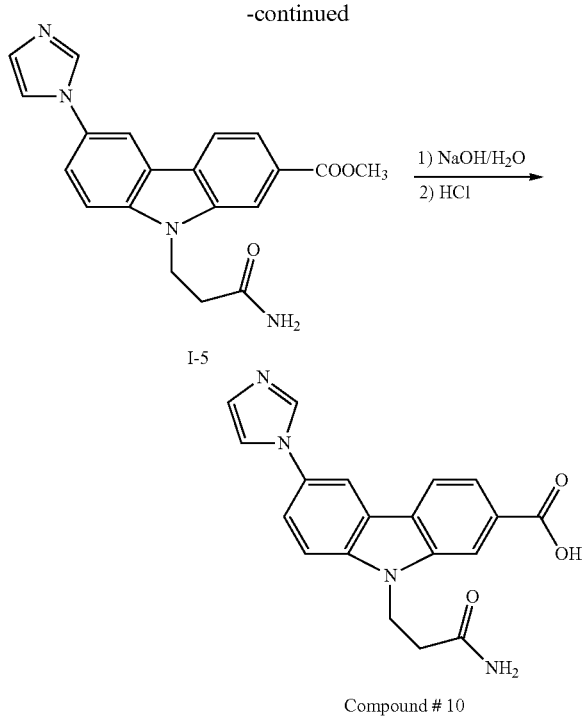

5. Administration and Pharmaceutical Composition

This disclosure provides novel compounds possessing GSNOR inhibitory activity that reduces pro-inflammatory mediator activity. Also provided herein are novel compounds possessing GSNOR inhibitory activity that reduces IL-6, IL-17, or IL-23 activity. Accordingly, these compounds are useful in treating conditions and/or disorders affected by (or at least in part by) GSNOR inhibition. Such conditions include asthma, exercise induced asthma, COPD, idiopathic pulmonary fibrosis, lung injury due to cystic fibrosis, type I and II diabetes, atherosclerosis, ischemic heart disease, myocardial infarction, myocarditis, endocarditis, coronary artery disease, heart failure, ischemia reperfusion injury, septic shock, toxic shock syndrome, pulmonary arterial hypertension, coronary artery re-stenosis, cardiomyopathy, congestive heart failure, arrhythmia, peripheral arterial disease, sickle cell anemia, embolic disease, cerebrovascular accidents, rheumatoid arthritis, osteoarthritis, atherosclerosis, multiple sclerosis, inflammatory bowel disease, Crohn's disease, ulcerative colitis, chronic kidney disease, autoimmune diseases, glomerulonephritis, psoriasis, cutaneous lupus erythematosus, systemic lupus erythematosus, systemic sclerosis, dermatitis, acne, atopic dermatitis, radiation dermatitis, radiation proctitis, ischemic stroke, traumatic brain injury, seizure, Alzheimer's disease, Parkinson's disease, Myasthenia gravis, chronic pain, aging and diseases of aging, alcoholic liver disease, liver cirrhosis, liver fibrosis, Fatty Liver Disease (Non-Alcoholic Fatty Liver Disease—NAFLD), hepatitis, and primary sclerosing cholangitis (PSC), and/or complications thereof.

In general, the compounds of this disclosure will be administered in a therapeutically effective amount by any of the accepted modes of administration for agents that serve similar utilities. The actual amount of the compound of this disclosure, i.e., the active ingredient, will depend upon numerous factors such as the severity of the disease to be treated, the age and relative health of the subject, the potency of the compound used, the route and form of administration, and other factors well known to the skilled artisan. The drug can be administered at least once a day, preferably once or twice a day.

An effective amount of such agents can readily be determined by routine experimentation, as can the most effective and convenient route of administration, and the most appropriate formulation. Various formulations and drug delivery systems are available in the art. See, e.g., Gennaro, A. R., ed. (1995) Remington's Pharmaceutical Sciences, 18$^{th}$ ed., Mack Publishing Co.

A therapeutically effective dose can be estimated initially using a variety of techniques well-known in the art. Initial doses used in animal studies may be based on effective concentrations established in cell culture assays. Dosage ranges appropriate for human subjects can be determined, for example, using data obtained from animal studies and cell culture assays.

An effective amount or a therapeutically effective amount or dose of an agent, e.g., a compound of this disclosure, refers to that amount of the agent or compound that results in amelioration of symptoms or a prolongation of survival in a subject. Toxicity and therapeutic efficacy of such molecules can be determined by standard pharmaceutical procedures in cell cultures or experimental animals, e.g., by determining the LD50 (the dose lethal to 50% of the population), and the Maximum tolerated Dose (MTD), and the ED50 (the dose therapeutically effective in 50% of the population). The dose ratio of toxic to therapeutic effects is the therapeutic index, which can be expressed as the ratio LD50 or MTD/ED50. Agents that exhibit a high therapeutic index are preferred.

The effective amount or therapeutically effective amount is the amount of the compound or pharmaceutical composition that will elicit the biological or medical response of a tissue, system, animal or human that is being sought by the researcher, veterinarian, medical doctor or other clinician. Dosages particularly fall within a range of circulating concentrations that includes the ED50 with little or no toxicity. Dosages may vary within this range depending upon the dosage form employed and/or the route of administration utilized. The exact formulation, route of administration, dosage, and dosage interval should be chosen according to methods known in the art, in view of the specifics of a subject's condition.

Dosage amount and interval may be adjusted individually to provide plasma levels of the active moiety that are sufficient to achieve the desired effects; i.e., the minimal effective concentration (MEC). The MEC will vary for each compound but can be estimated from, for example, in vitro data and animal experiments. Dosages necessary to achieve the MEC will depend on individual characteristics and route of administration. In cases of local administration or selective uptake, the effective local concentration of the drug may not be related to plasma concentration.

The amount of agent or composition administered may be dependent on a variety of factors, including the sex, age, and weight of the subject being treated, the severity of the affliction, the manner of administration, and the judgment of the prescribing physician.

This disclosure is not limited to any particular composition or pharmaceutical carrier, as such may vary. In general, compounds of this disclosure will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen that can be adjusted according to the degree of affliction. Compositions can take the form of tablets, pills, capsules, semisolids, powders, sustained release formulations, solutions, suspensions, elixirs, aerosols, or any other appropriate compositions. Another preferred manner for administering compounds of this disclosure is inhalation.

The choice of formulation depends on various factors such as the mode of drug administration and bioavailability of the drug substance. For delivery via inhalation the compound can be formulated as liquid solution, suspensions, aerosol propellants or dry powder and loaded into a suitable dispenser for administration. There are several types of pharmaceutical inhalation devices-nebulizer inhalers, metered dose inhalers (MDI) and dry powder inhalers (DPI). Nebulizer devices produce a stream of high velocity air that causes the therapeutic agents (which are formulated in a liquid form) to spray as a mist that is carried into the subject's respiratory tract. MDI's typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the subject's inspiratory air-stream during breathing by the device. In order to achieve a free flowing powder, the therapeutic agent is formulated with an excipient such as lactose. A measured amount of the therapeutic agent is stored in a capsule form and is dispensed with each actuation.

Pharmaceutical dosage forms of a compound of this disclosure may be manufactured by any of the methods well-known in the art, such as, for example, by conventional mixing, sieving, dissolving, melting, granulating, dragee-making, tableting, suspending, extruding, spray-drying, levigating, emulsifying, (nano/micro-) encapsulating, entrapping, or lyophilization processes. As noted above, the compositions of this disclosure can include one or more physiologically acceptable inactive ingredients that facilitate processing of active molecules into preparations for pharmaceutical use.

Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability. Such formulations are encompassed by the present disclosure.

The compositions are comprised of, in general, a compound of this disclosure in combination with at least one pharmaceutically acceptable excipient. Acceptable excipients are non-toxic, aid administration, and do not adversely affect the therapeutic benefit of the claimed compounds. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this disclosure the in aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990).

The compositions of this disclosure may, if desired, be presented in a pack or dispenser device containing one or more unit dosage forms containing the active ingredient. Such a pack or device may, for example, comprise metal or plastic foil, such as a blister pack, or glass, and rubber stoppers such as in vials. The pack or dispenser device may be accompanied by instructions for administration. Compositions comprising a compound of this disclosure can be formulated in a compatible pharmaceutical carrier may also be prepared, placed in an appropriate container, and labeled for treatment of an indicated condition.

The amount of the compound in a formulation can vary within the full range employed by those skilled in the art. Typically, the formulation will contain, on a weight percent (wt %) basis, from about 0.01-99.99 wt % of a compound of this disclosure based on the total formulation, with the balance being one or more suitable pharmaceutical excipients. Preferably, the compound is present at a level of about 1-80 wt %. Representative pharmaceutical formulations are described below.

FORMULATION EXAMPLES

The following are representative pharmaceutical formulations containing a compound of Formula I, II, III, IV, and/or V.

Formulation Example 1—Tablet Formulation

The following ingredients are mixed intimately and pressed into single scored tablets.

| Ingredient | Quantity per tablet, mg |
| --- | --- |
| compound of this disclosure | 400 |
| cornstarch | 50 |
| croscarmellose sodium | 25 |
| lactose | 120 |
| magnesium stearate | 5 |

Formulation Example 2—Capsule Formulation

The following ingredients are mixed intimately and loaded into a hard-shell gelatin capsule.

| Ingredient | Quantity per capsule, mg |
|---|---|
| compound of this disclosure | 200 |
| lactose, spray-dried | 148 |
| magnesium stearate | 2 |

Formulation Example 3—Suspension Formulation

The following ingredients are mixed to form a suspension for oral administration.

| Ingredient | Amount |
|---|---|
| compound of this disclosure | 1.0 g |
| fumaric acid | 0.5 g |
| sodium chloride | 2.0 g |
| methyl paraben | 0.15 g |
| propyl paraben | 0.05 g |
| granulated sugar | 25.0 g |
| sorbitol (70% solution) | 13.00 g |
| Veegum K (Vanderbilt Co.) | 1.0 g |
| flavoring | 0.035 mL |
| colorings | 0.5 mg |
| distilled water | q.s. to 100 mL |

Formulation Example 4—Injectable Formulation

The following ingredients are mixed to form an injectable formulation.

| Ingredient | Amount |
|---|---|
| compound of this disclosure | 0.2 mg-20 mg |
| sodium acetate buffer solution, 0.4M | 2.0 mL |
| HCl (1N) or NaOH (1N) | q.s. to suitable pH |
| water (distilled, sterile) | q.s. to 20 mL |

Formulation Example 5—Suppository Formulation

A suppository of total weight 2.5 g is prepared by mixing the compound of this disclosure with Witepsol® H-15 (triglycerides of saturated vegetable fatty acid; Riches-Nelson, Inc., New York), and has the following composition:

| Ingredient | Amount |
|---|---|
| Compound of this disclosure | 500 mg |
| Witepsol ® H-15 | balance |

The following synthetic and biological examples are offered to illustrate this disclosure and are not to be construed in any way as limiting the scope of this disclosure. Unless otherwise stated, all temperatures are in degrees Celsius.

EXAMPLES

This disclosure is further understood by reference to the following examples, which are intended to be purely exemplary of this disclosure. This disclosure is not limited in scope by the exemplified embodiments, which are intended as illustrations of single aspects of this disclosure only. Any methods that are functionally equivalent are within the scope of this disclosure. Various modifications of this disclosure in addition to those described herein will become apparent to those skilled in the art from the foregoing description and accompanying figures. Such modifications fall within the scope of the appended claims.

In the examples below, the following abbreviations have the following meanings. If an abbreviation is not defined, it has its generally accepted meaning.

aq.=aqueous
LC-MS=liquid chromatography-mass spectrometry
MS=mass spectrometry
THF=tetrahydrofuran
$NaHCO_3$=sodium bicarbonate
DIEA=diisopropylethylamine
MS=mass spectrometry
NaH=sodium hydride
o/n=overnight
HATU=1-[Bis(dimethylamino)methylene]-1H-1,2,3-trIzolo[4,5-b]pyridinium 3-oxid hexafluorophosphate
r.t.=room temperature
LAH=lithium aluminum hydride
DCM=dichloromethane
DMF=dimethylformamide
DMSO=dimethyl sulfoxide
equiv.=equivalent
EtOAc=ethyl acetate
EtOH=ethanol
g=gram
h=hours
HCl=hydrochloric acid
HPLC=high-performance liquid chromatography
HOAc=acetic acid
M=molar
MeOH=methanol
mg=milligrams
mL=milliliters
mmol=millimols
mp=melting point
m/z=mass to charge ratio
NaCl=sodium chloride
$Na_2CO_3$=sodium carbonate
NMR=nuclear magnetic resonance
NaOH=sodium hydroxide
$Na_2SO_4$=sodium sulfate
TLC=thin layer chromatography
UV=ultraviolet
wt %=weight percent
µM=micromolar

GENERAL EXPERIMENTAL DETAILS

Final compounds were confirmed by GC/MS analysis and determined to be ≥90%. $^1H$ and $^{13}C$ NMR spectra were recorded on a Bruker AM 400 spectrometer (operating at 400 and 101 MHz respectively) or a Bruker AVIII spectrometer (operating at 500 and 126 MHz respectively) in $CDCl_3$ (residual internal standard $CHCl_3$=δ 7.26), DMSO-$d_6$ (residual internal standard $CD_3SOCD_2H$=δ 2.50), or acetone-$d_6$ (residual internal standard $CD_3COD_2H$=δ 2.05). The chemical shifts (δ) reported are given in parts per million (ppm) and the coupling constants (J) are in Hertz (Hz). The spin multiplicities are reported as s=singlet, bs=broad singlet, bm=broad multiplet=doublet, t=triplet, q=quartet, p=pentuplet, dd=doublet of doublet, ddd=doublet of doublet of doublet, dt=doublet of triplet, td=triplet of doublet, tt=triplet of triplet, and m=multiplet.

GC/MS analysis was carried out with heat gradient elution. Medium pressure liquid chromatography (MPLC) was performed on a Teledyne Isco CombiFlash Rf purification system using gradient elution through standard RediSep Rf columns. Microwave irradiated reactions were carried out using a Biotage Initiator Classic synthesizer.

The following are experimental reactions used to synthesize intermediates and the final carbazole compounds.

General Synthesis for Nitro and Boronic Acid Aromatic Compounds:

The aromatic boronic acid or nitro compound is transformed via an electrophilic or nucleophilic aromatic substitution reaction. In the case of nucleophilic displacement, the aromatic compound starting material possesses an organic leaving group such as fluorine or bromine. The starting material and an appropriate nucleophile, such as imidazole, in DMF or other dipolar aprotic solvent are reacted with an inorganic base such as carbonate. The reaction is added to water and extracted three times with ethyl acetate. The combined organic layers are washed with 10% HCl, brine, dried with MgSO$_4$, and concentrated in vacuo.

In the case electrophilic substitution, the aromatic compound and electrophile are reacted with a Lewis acid, such as BF$_3$Et$_2$O, in an aprotic organic solvent, e.g. THF. The reaction is added to water and extracted three times with ethyl acetate. The combined organic layers are washed with bicarbonate, brine, dried with MgSO$_4$, and concentrated in vacuo. The compound is the subjected to flash purification by silica gel chromatography using ethyl acetate and hexane as the eluting solvents (65% yield).

General Synthesis for Carbazoles:

An aromatic nitro compound is reacted with an aryl boronic acid and a palladium (0) complex under standard Suzuki coupling conditions (e.g. with inorganic base and aprotic organic solvent) to give the 2-nitro-1,1'-biphenyl adduct. The reaction is added to water and extracted three times with ethyl acetate. The combined organic layers are washed with brine, dried with MgSO$_4$, and concentrated in vacuo. Flash chromatography: MeOH/DCM.

Next, this product is heated to 210° C. in excess triphenylphosphine in o-Dichlorobenzene. The dark reaction mixture is added to a silica gel column and purified by using a methanol-dichloromethane gradient as eluting solvent.

Finally, the carbazole nitrogen is optionally substituted; for example by alkylation or by an addition reaction at an electrophilic sp$^2$ center. In the case of alkylation, the carbazole product is reacted with acrylonitrile in DMF or other dipolar aprotic solvent with carbonate base. The reaction is added to water and extracted three times with ethyl acetate. The combined organic layers are washed with 10% HCl, brine, dried with MgSO$_4$, and concentrated in vacuo.

In the case of addition, the carbazole can be reacted with acetic anhydride or chloride for instance. The final carbazole compound is the subjected to flash purification by silica gel chromatography using methanol and dichloromethane as the eluting solvents. (50% yield)

EXEMPLARY SYNTHESIS PROCEDURE

Example 1: Synthesis of Compound 10, 9-(3-amino-3-oxopropyl)-6-(1H-imidazo-1-yl)-9H-carbazole-2-carboxylic acid

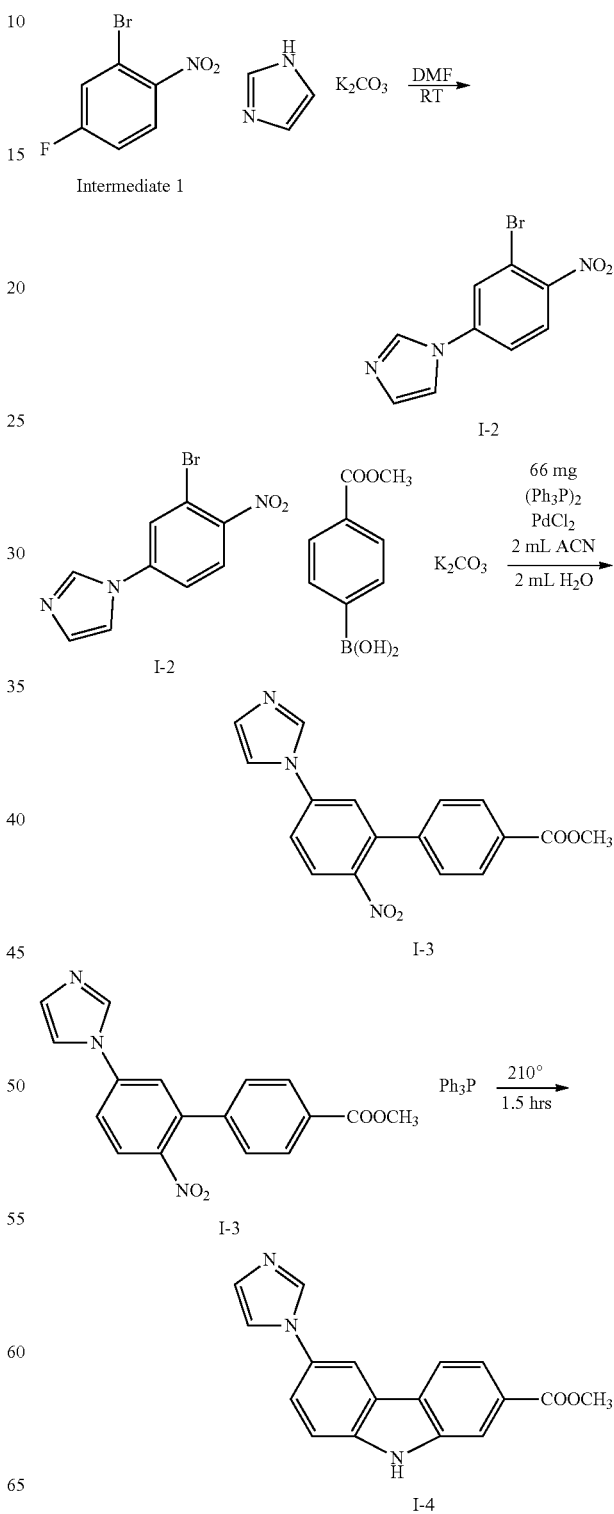

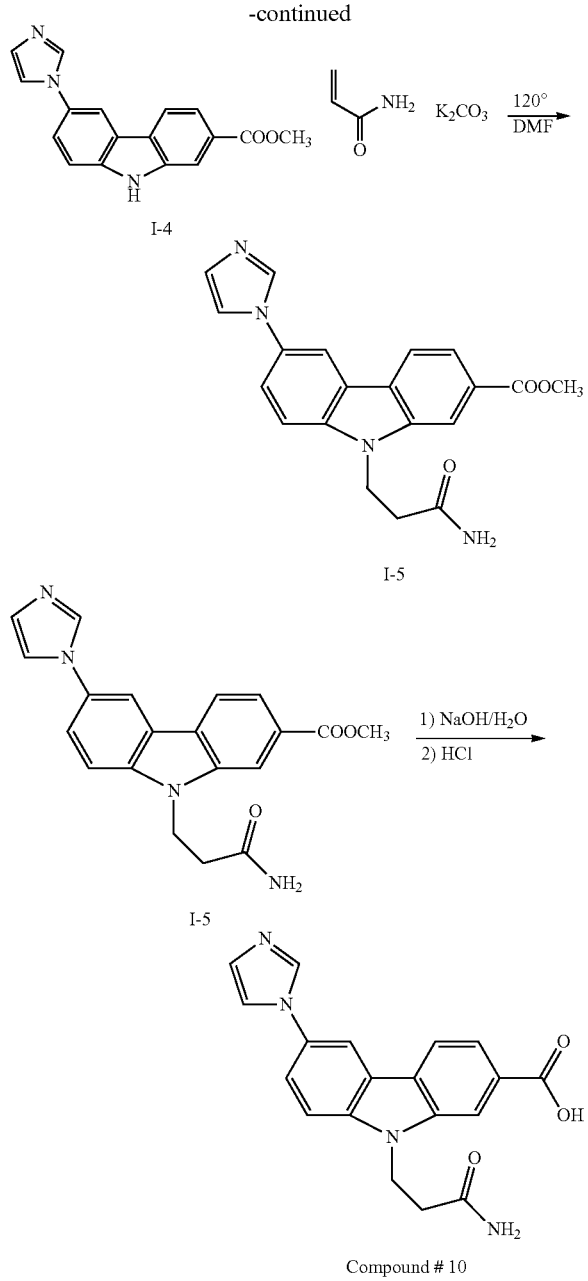

Compound # 10

Step 1:

To a solution of 2-bromo-4-fluoro-1-nitrobenzene (Intermediate 1, 1.00 g) in 25 mL dry DMF was added imidazole (325 mg) and potassium carbonate (750 mg), and the mixture was stirred at room temperature for 2 days. The reaction mixture was poured into ice-water, filtered, and washed well with water. TLC: One spot only, $R_f$ 0.50 (5% MeOH in DCM). The wet light yellow solid was dissolved in hot EtOAc, filtered, dried/MgSO$_4$, stripped to 986 mg light yellow solid. This material readily dissolved in DCM (~8 mL) and was put on a 25 g Silica (40-75u) cartridge, and chromatographed with 0-5% MeOH/DCM over 10 min; there was a small forerun, and 1-(3-bromo-4-nitrophenyl)-1H-imidazole, I-2, all came out from 6.5-8 min: 921 mg (75.6% yield) after pumping.

Step 2:

Intermediate I-2 (266 mg), (4-(methoxycarbonyl)phenyl) boronic acid (150 mg), and (Ph$_3$P)$_2$PdCl$_2$, (66 mg, catalyst) were mixed with 2 mL acetonitrile and 2 mL water in a microwave tube and degassed, and backfilled with argon. A 2-phase system resulted. This mixture was heated at 140 degrees (High) for 3600 sec, then another 1800 sec. The black and tarry looking reaction was filtered, partitioned with EtOAc and water, separated, and dried over magnesium sulfate. After chromatography, as above, 140 mg (44%) light yellow 85% pure methyl 5'-(1H-imidazol-1-yl)-2'-nitro-[1, 1'-biphenyl]-4-carboxylate, I-3, was obtained. GC/MS: 5.736 min, 15%, m/e: 270, 239 (base), dimethyl[1,1'-biphenyl]-4,4'-dicarboxylate (impurity) and 7.081 min (85%, m/e: 323, 292, 235), I-3.

Step 3:

I-3 (132 mg, 85% pure) was dissolved in 3 mL dimethylacetamide, triphenylphosphine (227 mg) was added, and the solution was heated to 210 degrees for 1.5 hours. TLC (5% MeOH/DCM) showed a new spot. The black reaction poured into water and was partitioned with EtOAc and water, separated, and dried over magnesium sulfate. It was filtered, stripped to dryness, dissolved in DCM and chromatographed as above. The new product had an $R_f$ of 0.24 in 5% MeOH/DCM, was UV-active and fluorescent with 365 nm light, and stained brown with iodine. 65 mg (64% yield), GC/MS: m/e: 291, methyl 6-(1H-imidazol-1-yl)-9H-carbazole-2-carboxylate, I-4, was obtained.

Step 4:

I-4 (65 mg), acrylamide (32 mg) and potassium carbonate (46 mg) was mixed in 2.5 mL dry DMF and heated to 120 degrees for several hours, until the I-4 could not be seen by TLC. The reaction mixture was poured into water and was partitioned with EtOAc and water, separated, and dried over magnesium sulfate. It was filtered and stripped to 48 mg (59%) light tan solid, $R_f$ 0.4 (running 5% MeOH/DCM twice). The solid was triturated with dichloromethane to obtain 33.6 mg very light tan crystals, methyl 9-(3-amino-3-oxopropyl)-6-(1H-imidazol-1-yl)-9H-carbazole-2-carboxylate, I-5. GC/MS: m/e: 362.

Step 5:

I-5 was heated in 1N NaOH/water until a clear solution was obtained. 1N HCl solution was added to obtain a white precipitate, 9-(3-amino-3-oxopropyl)-6-(1H-imidazol-1-yl)-9H-carbazole-2-carboxylic acid, Compound 10, that was filtered and dried under vacuum.

Example 2: Synthesis of Compound 17, 3-(imidazol-1(H)-yl)-7-(2-carboxylethyl)-9(H)-(2-aminocarbonylethyl) carbazole

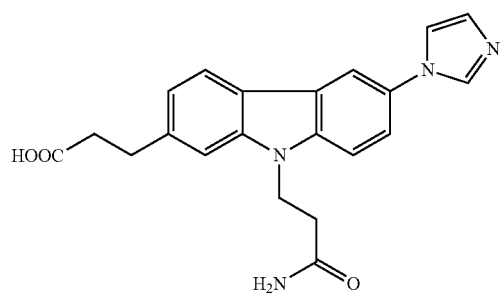 [SMILES: NC(=O)CCn1c2ccc(-n3ccnc3)cc2c2ccc(CCC(=O)O)cc21]

Methyl 3-(imidazole-1(H)-yl)-9(H)-carbazole-7-carboxylate (Intermediate A) was prepared following the procedure set forth in Example 1 with the exception that (4-(2-methoxy-carbonylethyl)phenyl)boronic acid was used in place of (4-(methoxycarbonyl)phenyl)boronic acid. To a solution of Intermediate A, (330 mg, 1 mmol, 1 eq.) in DMF (15 mL) were added $Cs_2CO_3$ (650 mg, 2 mmol, 2 eq.) and acrylamide (140 mg, 2 mmol, 2 eq.). The reaction mixture was heated up to 120° C. for 1 h. $Cs_2CO_3$ was filtrated off and DMF partially evaporated. The crude was solubilized in ethyl acetate and washed with brine (3 times). After evaporation, the resulting crude was purified by flash chromatography (DCM/MeOH: 100/0 to 90/10). A white solid was obtained (250 mg, 62%). The reaction was repeated on a 700 mg scale and 500 mg of the methyl ester of the title compound (Intermediate B) was obtained (60%). 1H NMR (400 MHz, DMSO☐d6) d ppm 1.18 (t, J=7.09 Hz, 3H) 2.58 (t, J=6.66 Hz, 2H) 2.74 (t, J=7.70 Hz, 2H) 3.06 (t, J=7.64 Hz, 2H) 4.08 (d, J=7.09 Hz, 2H) 4.61 (t, J=6.60 Hz, 2H) 6.89 (br. S., 1H) 7.08 ☐ 7.17 (m, 2H) 7.39 (br. S., 1H) 7.51 (s, 1H) 7.66 (d, J=1.83 Hz, 1H) 7.69 ☐ 7.79 (m, 2H) 8.09 (d, J=7.95 Hz, 1H) 8.22 (s, 1H) 8.36 (d, J=1.47 Hz, 2H).

This step illustrates how to convert the methyl ester to the corresponding carboxyl group. Specifically, to a solution of the Intermediate B (650 mg) in THF (40 mL) is added a solution of LiOH (650 mg) in water (40 mL). The reaction is stirred at room temperature for 3 h. Dichloromethane is added (50 mL) and the solution is carefully acidified with a 1N HCl aqueous solution until pH=1. The compound precipitates in the aqueous layer and is not soluble in the organic layer. The aqueous layer is separated and is filtrated through Buchner Funnel to afford a white solid which is carefully washed with water and dried in vacuum (400 mg, 65%). The rest of the product is soluble in the aqueous phase and hard to recover since it was not soluble in organic solvent.

Example 3: Synthesis of Compound 26, 3-(imidazol-1(H)-yl)-7-(2-carboxylethyl)-9(H)-(2-cyanoethyl) carbazole

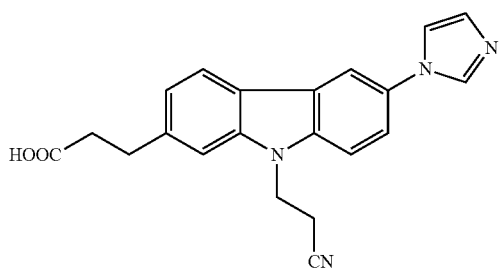 [SMILES: N#CCCn1c2ccc(-n3ccnc3)cc2c2ccc(CCC(=O)O)cc21]

Intermediate A from Example 2 is converted to the corresponding 9-(2-cyanoethyl) derivative using acrylonitrile in place of acrylamide. After reaction completion, deacylation of the methoxy ester following the procedures set forth above provides for the title compound.

Example 4: Synthesis of 3-(imidazol-1(H)-yl)-7-(2-carboxylethyl)-9(H)-(3-cyanopropy) carbazole

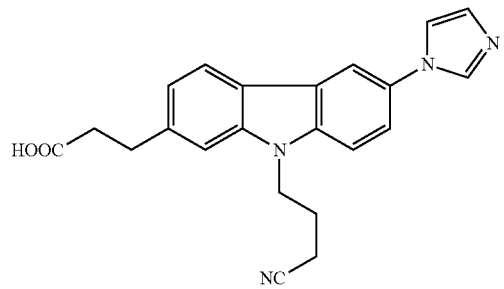 [SMILES: N#CCCCn1c2ccc(-n3ccnc3)cc2c2ccc(CCC(=O)O)cc21]

Intermediate A from Example 2 is converted to the corresponding 9-(3-cyanopropyl) derivative using 1-bromo-3-cyanopropane in place of acrylamide. After reaction completion, deacylation of the methoxy ester following the procedures set forth above provides for the title compound.

The following compounds are also prepared based on the methods described herein, using the appropriate starting materials. Other compounds as described herein may also be prepared based on the methods described herein using the appropriate starting materials.

TABLE 3

| Compound | Structure |
|---|---|
| K1 | 7-methoxy-9H-carbazole-2-carboxylic acid |
| L1 | 9-(3-amino-3-oxo-propyl)-7-methoxy-9H-carbazole-2-carboxylic acid |
| M1 | 9-(4-aminocarbonylphenyl)-7-methoxy-9H-carbazole-2-carboxylic acid |
| N1 | 6-[5-(2-methyl-1H-imidazol-1-yl)thien-2-yl]-9H-carbazole-2-carboxylic acid |
| O1 | 9-(3-amino-3-oxo-propyl)-6-[5-(2-methyl-1H-imidazol-1-yl)thien-2-yl]-9H-carbazole-2-carboxylic acid |
| P1 | 9-(4-aminocarbonyl-2-methylphenyl)-6-[5-(2-methyl-1H-imidazol-1-yl)thien-2-yl]-9H-carbazole-2-carboxylic acid |
| Q1 | 7-[(1H-imidazol-1-yl)methyl]-9H-carbazole-2-carboxylic acid |
| R1 | 6-(1H-imidazol-1-yl)-9H-carbazole-2-carboxylic acid |
| S1 | 9-(4-aminocarbonylphenyl)-6-(1H-imidazol-1-yl)-9H-carbazole-2-carboxylic acid |
| T1 | 9-(4-aminocarbonyl-2-methylphenyl)-6-(1H-imidazol-1-yl)-9H-carbazole-2-carboxylic acid |
| U1 | 9-(3-amino-3-oxo-propyl)-7-(1H-imidazol-1-yl)-9H-carbazole-2-carboxylic acid |
| V1 | 9-(4-aminocarbonylphenyl)-7-(1H-imidazol-1-yl)-9H-carbazole-2-carboxylic acid |
| W1 | 9-(4-aminocarbonyl-2-methylphenyl)-7-(1H-imidazol-1-yl)-9H-carbazole-2-carboxylic acid |

The following compounds were also prepared based on the methods described herein, using the appropriate starting materials. Table 2a and Table 2b also provides the % GSNOR inhibition at 20 µM of compounds described herein. The assay was performed as follows: The following reagents were mixed together and used to determine the % inhibition of GSNOR at 20 µM caused by each test compound: 0.240 mM GSNO, 0.240 mM NADH, GSNOR enzyme, 1.5 ug/ml, added to start the reaction. The buffer was 100 mM phosphate buffer (pH 7.4.) The rate of NADH consumption for each well was determined by ultraviolet spectroscopy. Plates were read on a Molecular Devices Spectra Max UV/Visible Spectrophotometer/plate reader and the change in 340 nm absorbance at 25° C. was recorded for each well at 10 sec intervals over the duration of the recording period (2~5 minutes). The rate was measured from the linear portion of the curve. Final test compound concentration was 20 µM. The mean % inhibition from 3 test compound wells and 5 control wells was measured as the percentage of the mean no compound+enzyme−the mean no enzyme, no compound control.

Table 2b also includes additional biological data of compounds described herein. The LPS/cytokine Assay was carried out in CD-1 male mice. The assay measured the level of various cytokines, including IL-6, IL-17, and IL-23, after induction by bacterial liposaccharide (LPS). Compounds were dosed by IP or IV routes of administration at varying times before and after LPS and the cytokine concentrations were measured at varying times, typically 6 hrs, after LPS by standard methods using ELISA kits.

TABLE 2a

| Compound | Structure | % Inhibit. at 20 µM |
|---|---|---|
| A1 (also referred to as 8) | 9-(3-amino-3-oxopropyl)-7-[(1H-imidazol-1-yl)methyl]-9H-carbazole-2-carboxylic acid | 80 |
| B1 (also referred to as 10) | 9-(3-amino-3-oxopropyl)-6-(1H-imidazol-1-yl)-9H-carbazole-2-carboxylic acid | 85 |
| 16 | 9-(4-aminocarbonyl-2-nitrophenyl)-7-[(1H-imidazol-1-yl)methyl]-9H-carbazole-2-carboxylic acid | 89.0 |
| 17 | 9-(3-amino-3-oxo-propyl)-6-(1H-imidazol-1-yl)-2-(2-carboxyethyl)-9H-carbazole | 92.8 |
| E1 | 9-(3-amino-3-oxopropyl)-3-fluoro-6-(1H-imidazol-1-yl)-9H-carbazole-2-carboxylic acid | 18 |
| F1 | 7-(5-(2-methyl-1H-imidazol-1-yl)thiophen-2-yl)-9H-carbazole-2-carboxylic acid | |
| G1 | 9-(4-cyano-2-nitrophenyl)-7-((thiazol-2-ylamino)methyl)-9H-carbazole-2-carboxylic acid | 15 |
| H1 | 9-(4-cyano-2-nitrophenyl)-7-((oxazol-2-ylamino)methyl)-9H-carbazole-2-carboxylic acid | 0* |
| I1 | 9-(4-carbamoyl-2-nitrophenyl)-7-((oxazol-2-ylamino)methyl)-9H-carbazole-2-carboxylic acid | 0* |
| J1 | 9-(4-carbamoyl-2-nitrophenyl)-7-((thiazol-2-ylamino)methyl)-9H-carbazole-2-carboxylic acid | 9 |

*These compounds are contemplated to have activity at higher concentration. To the extent that one or both of these compounds do not have activity, one or both of these compounds are excluded from some embodiments disclosed herein.

TABLE 2b

| Compound | IC$_{50}$ Micromolar* | % GSNOR Inhibition at 20 uM | LPS/IL6 Lowest tested active |
|---|---|---|---|
| 8 | ++ | 80.0 | |
| 10 | +++ | 75.0 | 30 mg/kg |
| 16 | ++ | 89.0 | |
| 26 | +++ | 92.4 | 0.3 mg/kg |
| 31 | +++ | 92.9 | 0.3 mg/kg |
| 17 | ++ | 92.8 | 0.03 mg/kg |
| 18 | + | 72.4 | |
| 19 | ++ | 81.3 | |
| 20 | ++ | 88.9 | 0.3 mg/kg |
| 21 | ++ | 93.6 | 0.3 mg/kg |
| 22 | | 81.4 | |
| 23 | | 93.4 | |
| 24 | | 90.0 | |
| 25 | | 92.0 | |

*Activity is provided as follows: +++ = IC$_{50}$ less than 1 µM; ++ = 1 µM < IC$_{50}$ < 5 µM, + = IC$_{50}$ is greater than 5 µM.

Example 5

BIOLOGICAL TESTING: Compounds 10 and 17 from Table 1 were tested in a mouse inflammation assay. Briefly, CD-1 mice were dosed with compound, 12 hrs before injecting mice I.P. with the potent cytokine inducer, bacterial lipopolysaccharide (LPS). The mice were euthanized 6 hrs after the LPS was injected and their serum prepared by standard methods. The concentration of IL-6 in the serum of each experimental animal was measured using an IL-6 ELISA kit from Enzo. The compounds tested were active.

Example 6: Effect of Compound 17 Treatment on Non-Alcoholic Steatohepatitis (NASH)

Aim:

To evaluate the effect of Compound 17 treatment on non-alcoholic steatohepatitis (NASH) in male C57BL/6 mice.

Protocol Summary:

Timed pregnant mice (n=44) were selected for the study. The delivered pups were subcutaneously injected on post-natal day 2 with 200 µg of Streptozotocin and were allowed to remain with the mother until they reached the weanling age. After weanling, the male pups were selected and fed with 60% kcal fat diet (Research Diet-D12492) for next 6 weeks. All the animals were observed once daily for clinical signs and twice daily for morbidity and mortality.

Study Procedure:

Mice were dosed with vehicle, Compound 17 (at 3 mg/kg or 10 mg/kg) and 10 mg/kg of reference compound (either Obeticholic acid (OCA) or Elafibranor (ELA, GFT505)) once daily before the start of dark cycle (6:00 PM) from day 0 to 21. Animal body weight measurements were made daily for the complete duration of the experiment. Animals were dosed for 21 days (from week 9 to 12) with the test and reference compounds. Blood glucose was estimated before the treatment start, day 11 and on the termination day. Histopathology analysis including the H&E staining, Masson's trichrome staining and the Oil-red-O (ORO) staining was performed for the liver tissues.

Glucose Results:

Relative to disease control, Compound 17 (10 mg/kg, i.p.) reduced plasma glucose by 17.4% ($p<0.01$), while neither OCA nor ELA reduced glucose.

Body Weight Results:

After 21 days of treatment with the test and reference compounds, Elafibranor exhibited statistically significant (*$p<0.05$) increase in body weight on day 7 (*$p<0.05$) and 12 (**$p<0.01$) post-treatment (Table 4). Compound 17 at 3 and 10 mg/kg doses put on the second least and least body weight increases and were both less than disease controls. Elafibrinor animals put on the most weight (+43% relative to naïve controls at day 21), followed by the Obeticholic acid (+28% relative to naïve controls at day 21), both more than disease controls and either dose of Compound 17 (3 mg/kg: +1.3%; 10 mg/kg: −43% relative to naïve controls at day 21).

TABLE 4

Effect of compounds on change in body weight (g)

| | Naïve control | | Disease control | | Compound 17 (3 mg/kg) | | Compound 17 (10 mg/kg) | | Obeticholic acid (10 mg/kg) | | Elafibranor (10 mg/kg) | |
|---|---|---|---|---|---|---|---|---|---|---|---|---|
| Day | Mean | SEM | Mean | SEM | Mean | SEM | Mean | SEM | Mean | SEM | Mean | SEM |
| 1 | 0.00 | 0.00 | 0.00 | 0.00 | 0.00 | 0.00 | 0.00 | 0.00 | 0.00 | 0.00 | 0.00 | 0.00 |
| 2 | −0.23 | 0.07 | 0.09 | 0.23 | 0.54 | 0.27 | 0.65 | 0.13 | 0.43 | 0.19 | 0.70 | 0.25 |
| 3 | 0.54 | 0.15 | 0.07 | 0.28 | 0.85 | 0.50 | 0.96 | 0.11 | 0.57 | 0.17 | 1.18 | 0.34 |
| 4 | 0.71 | 0.12 | −0.29 | 0.28 | 0.48 | 0.42 | 0.76 | 0.18 | 0.43 | 0.20 | 0.93 | 0.33 |
| 5 | 0.94 | 0.13 | 0.09 | 0.31 | 0.35 | 0.44 | 0.81 | 0.28 | 0.45 | 0.06 | 1.42 | 0.38 |
| 6 | 0.52 | 0.19 | 0.07 | 0.34 | 0.68 | 0.36 | 0.84 | 0.21 | 0.78 | 0.15 | 1.31 | 0.53 |
| 7 | 0.49 | 0.22 | −0.10 | 0.40 | 0.54 | 0.39 | 0.19 | 0.26 | 0.58 | 0.13 | 1.43 | 0.47 |
| 8 | 0.30 | 0.22 | −0.18 | 0.23 | 0.21 | 0.38 | 0.78 | 0.26 | 0.89 | 0.16 | 1.49 | 0.57 |
| 9 | 0.77 | 0.25 | 0.31 | 0.29 | 0.53 | 0.40 | 0.80 | 0.14 | 0.85 | 0.13 | 1.71 | 0.59 |
| 10 | 0.42 | 0.29 | 0.62 | 0.32 | 0.56 | 0.43 | 0.89 | 0.18 | 1.06 | 0.11 | 1.69 | 0.50 |
| 11 | 0.88 | 0.19 | 0.42 | 0.34 | 0.40 | 0.40 | 0.91 | 0.18 | 0.78 | 0.14 | 1.47 | 0.54 |
| 12 | −0.11 | 0.17 | −0.74 | 0.37 | −0.49 | 0.38 | −0.08 | 0.28 | 0.06 | 0.14 | −0.17 | 0.56 |
| 13 | 1.06 | 0.21 | −0.29 | 0.65 | 0.81 | 0.39 | 0.74 | 0.31 | 0.82 | 0.20 | 1.73 | 0.57 |
| 14 | 1.36 | 0.31 | 0.52 | 0.62 | 1.10 | 0.40 | 0.71 | 0.28 | 1.05 | 0.17 | 1.96 | 0.62 |
| 15 | 1.43 | 0.34 | 0.70 | 0.54 | 0.84 | 0.42 | 1.01 | 0.23 | 0.54 | 0.22 | 2.00 | 0.57 |
| 16 | 1.42 | 0.28 | 1.13 | 0.68 | 1.32 | 0.44 | 1.09 | 0.23 | 0.82 | 0.24 | 1.64 | 0.54 |
| 17 | 1.41 | 0.32 | 1.34 | 0.46 | 1.38 | 0.44 | 1.13 | 0.31 | 1.43 | 0.20 | 1.82 | 0.61 |
| 18 | 1.46 | 0.30 | 1.63 | 0.69 | 1.11 | 0.37 | 0.97 | 0.45 | 1.52 | 0.22 | 2.16 | 0.68 |
| 19 | 1.40 | 0.32 | 1.53 | 0.61 | 1.22 | 0.43 | 1.16 | 0.41 | 1.81 | 0.23 | 2.26 | 0.63 |
| 20 | 1.68 | 0.29 | 1.65 | 0.64 | 1.56 | 0.44 | 0.80 | 0.41 | 1.62 | 0.19 | 1.88 | 0.60 |
| 21 | 1.55 | 0.37 | 1.87 | 0.54 | 1.57 | 0.42 | 0.89 | 0.36 | 1.98 | 0.35 | 2.22 | 0.72 |

Liver Weight/Body Weight Results:

When compared with the disease control, Compound 17 at 3 and 10 mg/kg doses reduced the liver to body weight ratio from 0.066 to 0.054 (#p<0.05) and 0.055 respectively (−18.5% and −16.2%). Obeticholic acid reduced the ratio to 0.058 (−11%), and Elafibranor raised the ratio by +40% to 0.092 (###p<0.001).

Liver Collagen Deposits:

In comparison with the disease control group (where increased collagen deposits were observed), all the treatment groups exhibited decreased collagen deposits in the liver tissues. The quantification of Masson's trichrome staining area reveals that the percentage collagen proportion area (CPA) decreased by 29% and 20% with Compound 17 at doses of 3 mg/kg and 10 mg/kg, respectively. Obeticholic acid and Elafibranor decreased the collagen deposits in liver tissues by 50% and 54%, respectively.

NAS Score Results:

Compound 17 significantly decreased the NAS both at 3 (*p<0.05) and 10 mg/kg (*p<0.05). The NAS for the Obeticholic acid was 3.20 and Elafibranor was 2.67 (**p<0.05. However, it should be noted that the steatosis score measured by the Oil-Red-O (ORO) staining is considered as the more accurate measure of steatosis. The ORO score was much lower for the Compound 17 treated animals (−28% and −52% relative to disease control) than for either Obeticholic acid (−1%) or Elafibranor (−11%).

The above results demonstrate that Compound 17 (at 3 mg/kg and 10 mg/kg doses) markedly reduced steatosis and lobular inflammation in the liver similar to Elafibranor and more than Obeticholic acid as indicated by the NAS. Compound 17 also reduced weight gain, liver to body weight ratio, fasting glucose, and liver fat accumulation as measured by ORO staining. Compound 17 tended to reduce collagen staining as determined by Masson's Trichrome staining by more than Obeticholic acid and Elafibranor. These studies demonstrate that Compound 17 may be useful for treating NASH.

Example 7: Effect of Compound 17 Treatment on Idiopathic Pulmonary Fibrosis (IPF)

Aim:

The objective of this study was to determine the efficacy of Compound 17 in the Bleomycin-induced idiopathic pulmonary fibrosis model in male C57BL/6 mice.

Study Procedure:

Compound 17 was made-up fresh every 4 days. A required amount of the test compound was weighed in a glass vial and the purity factor was calculated. A stock solution of 1 mg/ml (10 mg/kg) was made in distilled water (pH 8) and the subsequent 3 and 1 mg/kg doses (concentrations) were obtained by serial dilution of the 1 mg/ml stock solution. A clear and transparent solution was observed. Animals were dosed with Compound 17 at 1 mg/kg, 3 mg/kg and 10 mg/kg, i.p (intraperitoneal), once daily from day 14 to 28.

Pirfenidone was weighed in a glass vial and suspended in 0.5% methyl cellulose to obtain a 10 mg/ml formulation. A clear homogenous suspension was observed. Animals were dosed with Pirfenidone at 100 mg/kg, p.o., b.i.d., from day 14 to 28.

Figure 2:
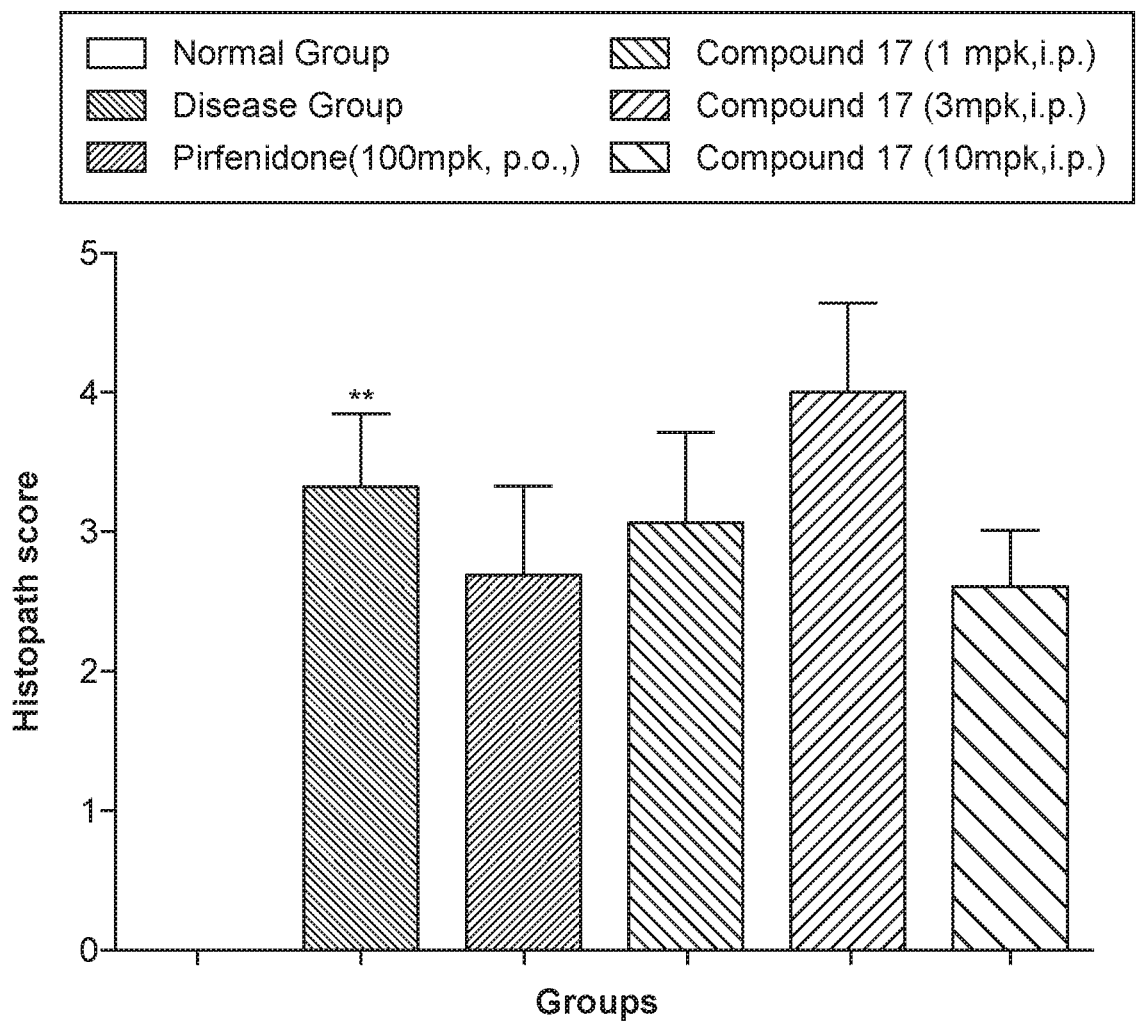
FIG. 2 illustrates the effect of Compound 17 on lung fibrosis graded by the Ashcroft System in a mouse model of Bleomycin-induced IPF. The data indicates mean±SEM fibrosis score. mpk=mg/kg; i.p.=intraperitoneal; p.o.=orally. **p<0.01 as compared to naïve control. One-way ANOVA followed by Dunnett's Multiple Comparison Test. n=7-12.
Figure 3:
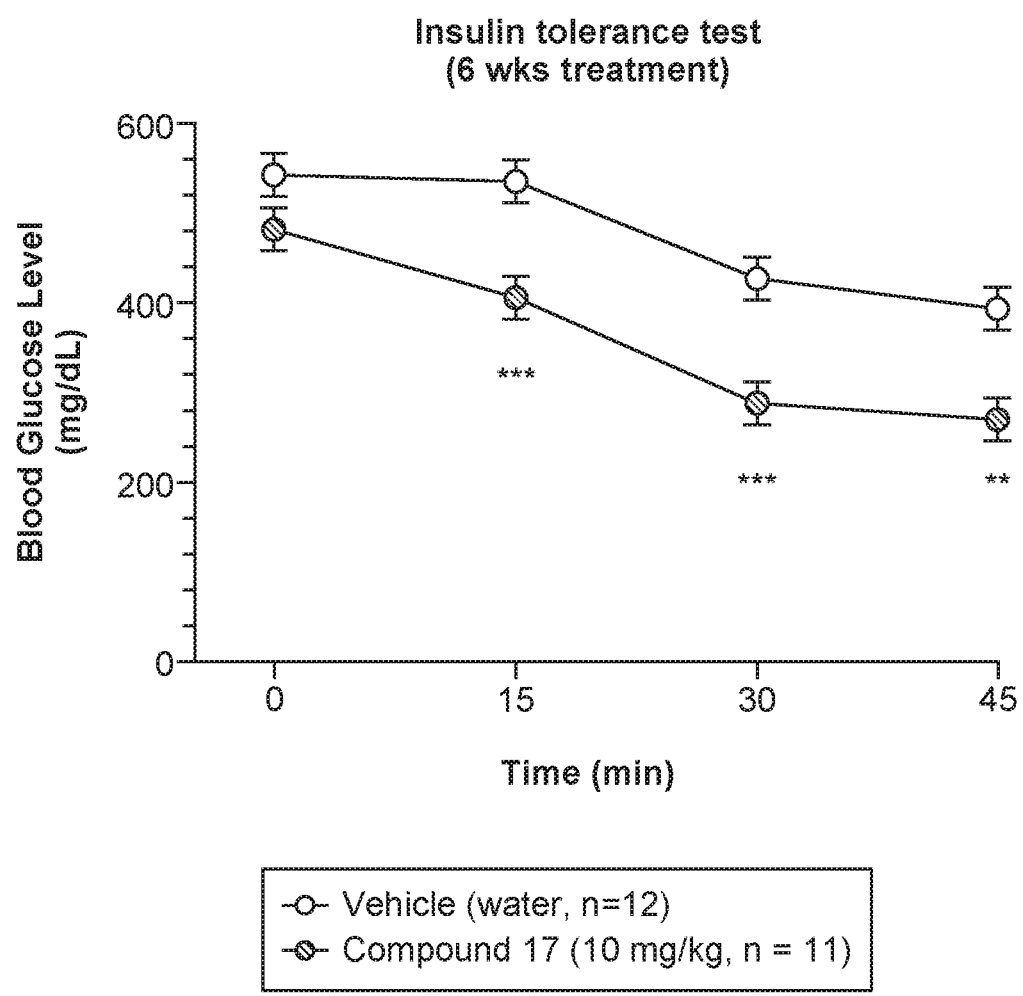
FIG. 3 illustrates the effect of Compound 17 on blood glucose level as an Intra-gastric Insulin Tolerance Test (IGITT) after 6 weeks of drug treatment in db/db diabetic mice after intraperitoneal injection of 0.75 IU human insulin per gram of mouse body weight.
Figure 4:
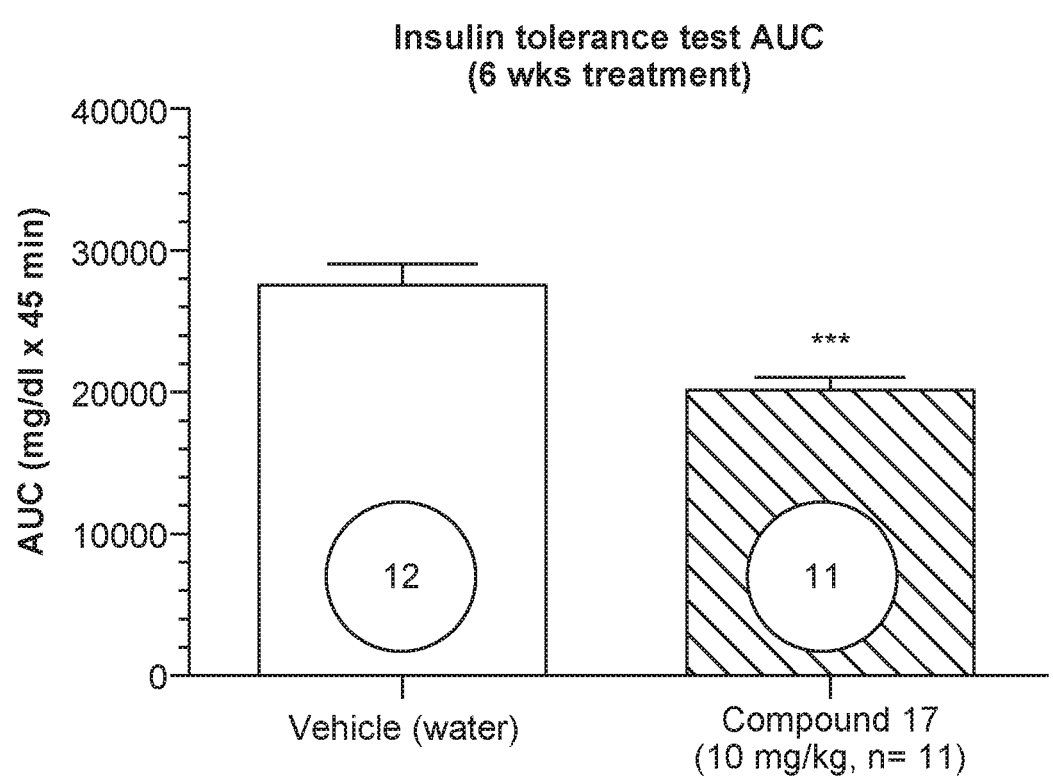
FIG. 4 illustrates the integral of the plasma glucose concentration in mg/dL as a function of time over 45 min (AUC) of Compound 17 as an IGITT.
Figure 5:
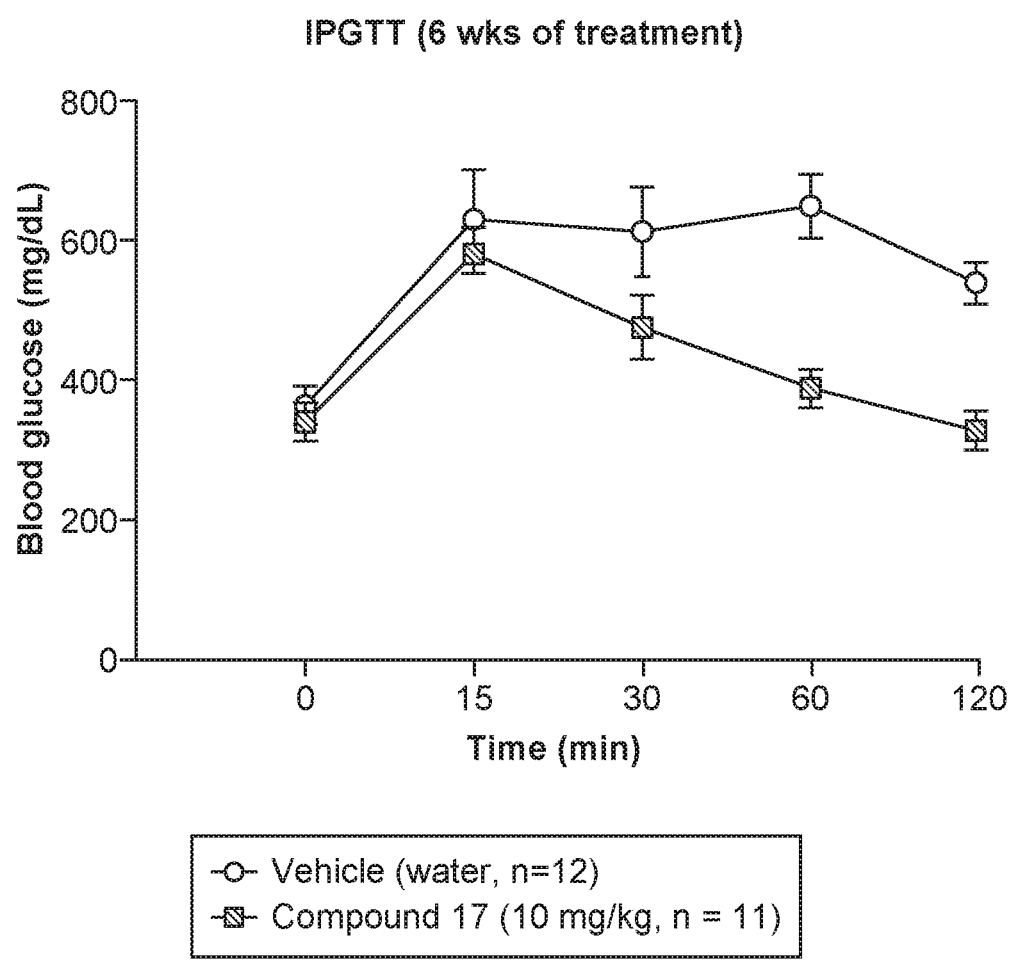
FIG. 5 illustrates the Intra-gastric Glucose Tolerance Test (IPGTT) of Compound 17 on blood glucose level as a function of time over 120 minutes after intraperitoneal injection of 0.75 IU human insulin per gram of mouse body weight after 6 weeks of drug treatment in db/db diabetic mice.
Figure 6:
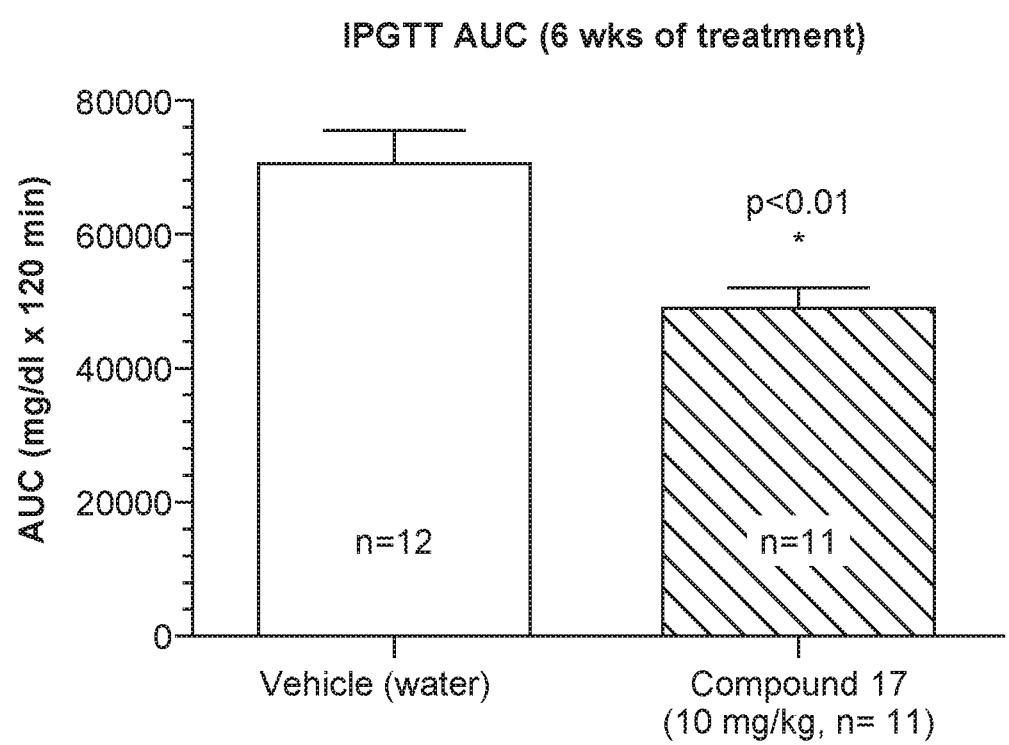
FIG. 6 illustrates an IPGTT of Compound 17 as the integral of the plasma glucose concentration in mg/dL as a function of time over 120 min (AUC).

Results:

Significant lung fibrosis both on day 14 and 28 (FIG. 2) was demonstrated in the disease group as compared with the normal group by the Ashcroft system-based fibrosis grading and Masson's trichrome staining-based percentage collagen proportionate area. There was a notable mitigation of pulmonary fibrosis in both the Pirfenidone, 100 mg/kg and Compound 17, 10 mg/kg groups, when compared with the disease control group as revealed by the reduced Ashcroft score and percentage collagen proportionate area.

Conclusions:

Analysis by H&E staining and Masson's trichrome staining (FIG. 1; p.o.=orally; b.i.d.=twice daily) indicated a severe fibrosis in the lung tissues from disease control group on day 14 and 28 post-Bleomycin instillation. In the therapeutic mode, daily administration of Compound 17, 10 mg/kg from day 14 to 28 post-Bleomycin instillation, decreased lung fibrosis. Based on the histopathological analysis and data, the efficacy of Pirfenidone and Compound 17 (10 mg/kg dose) were comparable.

Example 8: Effect of Compound 17 Treatment on Insulin and Glucose Tolerances

Nitric Oxide (NO) is one of the most critical molecules in maintaining cardiovascular health and is part of the insulin signaling pathway. The generation of NO by the constitutive enzyme, endothelial nitric oxide synthase (eNOS) and of the cellular storage form of NO, S-nitrosoglutathione (GSNO), are essential for normal physiological regulation of blood flow and nutrient delivery to tissues. NO and GSNO are two of the most important signaling molecules in our body; loss of NO and GSNO function is one of the earliest indicators or markers of cardiovascular disease and diabetes. Numerous clinical studies have also clearly documented severe endothelial dysfunction in humans that suffer from diabetes mellitus. Moreover, the dysfunctional NO pathway in diabetics is thought to be the cause of the increased incidence of cardiovascular complications.

The increase in circulating glucose, insulin, and cytokines that occurs in type II diabetes ("T2D") have all been independently shown to impair eNOS enzyme activity in experimental studies. All of these conditions acting independently or in unison could render the eNOS enzyme dysfunctional. Furthermore, advanced glycosylation end products that are generated in the plasma of diabetic patients can very readily quench any NO that is formed by the endothelium and this is thought to be a major mechanism responsible for defective endothelium-dependent vasodilation in diabetics. The physiological significance of impaired eNOS function and reductions in vascular NO bioavailability may serve to reduce blood flow to various organs in patients with diabetes mellitus. Therefore, developing new strategies to restore and replete nitrosylation and nitrosylation based signaling is of paramount importance and could potentially save millions of lives worldwide and reduce the cardiovascular and other burdens in diabetics.

Study Procedure:

Compound 17 was studied in 6 week intra-gastric insulin and glucose tolerance tests in db/db mice dosed orally with Compound 17 at 10 mg/kg for 6 weeks qd. The male db/db mice were started on study at 6 weeks of age and were given a 60% high fat diet to increase the diabetic phenotype.

Vascular reactivity: Db/db mouse aorta segments were equilibrated in oxygenated PBS (95% $O_2$ and 5% $CO_2$) at 37° C. Following equilibration, 1 µM phenylephrine was added to each ring for submaximal contraction. After stabilization, Compound 17 was added to the rings and the effect on the muscle tone of the aorta segments was monitored with a tensometer as dose-responses from 10-8 M to 10-5 M for acetylcholine ("Ach") and A23187 (5-(methylamino)-2-({(2R,3R,6S,8S,9R,11R)-3,9,11-trimethyl-8-[(1S)-1-methyl-2-oxo-2-(1H-pyrrol-2-yl)ethyl]-1,7-dioxaspiro[5.5]undec-2-yl}methyl)-1,3-benzoxazole-4-carboxylic). 8-Isoprostane was measured in plasma and heart homogenates by standard Elisa methods.

Figure 8:
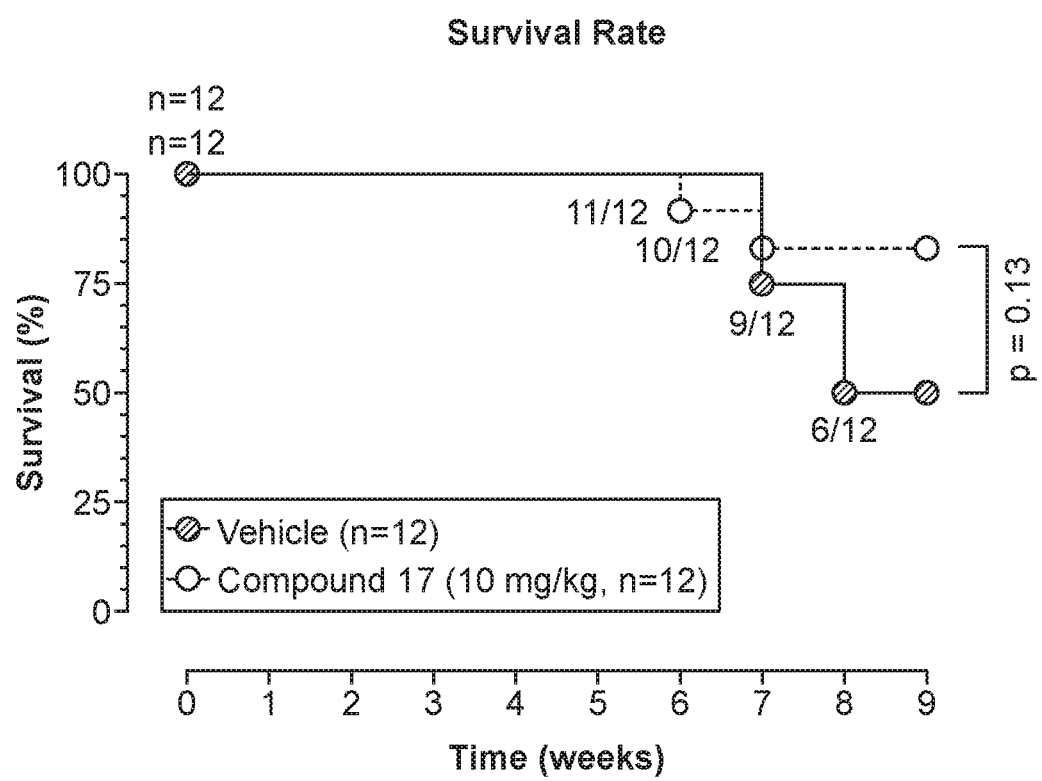
FIG. 8 illustrates survival rate of db/db female mice administered Compound 17 versus vehicle.
Figure 9:
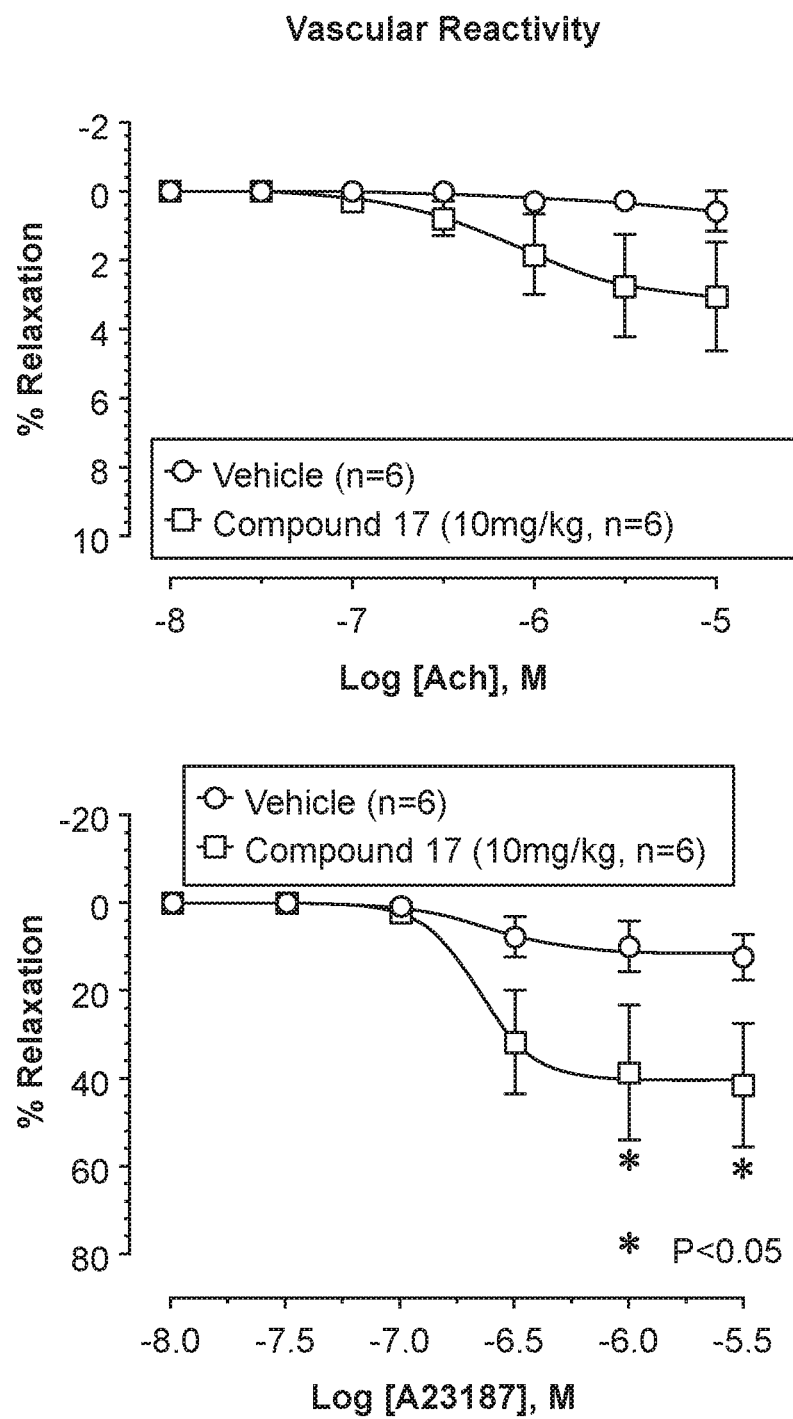
FIG. 9 illustrates vascular reactivity in db/db female mice administered Compound 17 versus vehicle.
Figure 10:
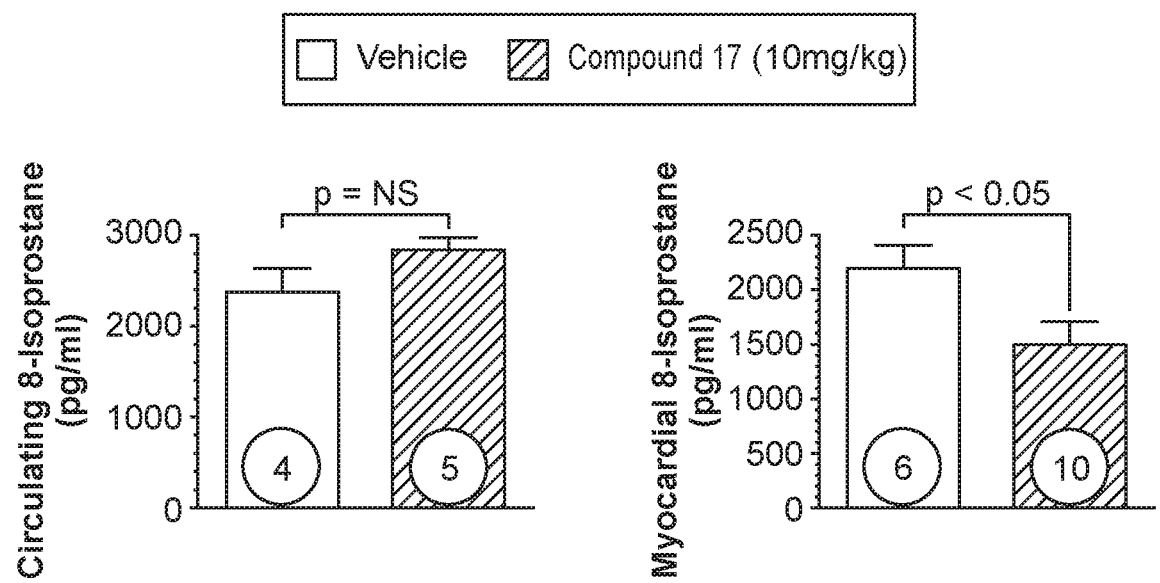
FIG. 10 illustrates circulating 8-isoprostane and myocardial 8-isoprostane in db/db female mice administered Compound 17 versus vehicle.

The results show that Compound 17 statistically significantly reduced insulin and glucose tolerances (FIG. 3 to FIG. 6). In addition, Compound 17 increased survival in severely debilitated diabetic mice by 66% and increased their vascular reactivity (FIG. 8 to FIG. 10).

Oxidative stress, produced by free radical oxygen containing radicals, are among the root causes of many inflammatory, oxidant based, and fibrotic diseases. The products of oxidative stress are best measured by quantitating the amount of F2-isoprostanes in a target tissue of damage in the disease under consideration. The isoprostanes are a unique series of prostaglandin-like compounds formed in vivo via a non-enzymatic mechanism involving the free radical-initiated peroxidation of arachidonic acid. The quantification of F2-Isoprostanes ("F2-IsoPs") represent an accurate method to assess oxidative stress status in vivo. F2-IsoPs are prostaglandin-like compounds which are produced by a noncyclooxygenase free radical-catalyzed mechanism involving the peroxidation of arachidonic and other fatty acids. The data shown in FIG. 10 demonstrates that Compound 17 significantly reduces the amount of F2-IsoPs in cardiac tissue (i.e., myocardial 8-isoprostane), one of the targets of T2D pathology. Compound 17's ability to reduce F2-IsoPs also indicates that Compound 17 may reduce oxidant damage and induce the Nrf-2 anti-oxidant response system. Since oxidant damage drives the pathophysiology underlying many important fibrotic and inflammatory diseases, it is contemplated that Compound 17, and other GSNOR inhibitors of this disclosure, may be active against many of those diseases.

Example 9: Effect of Compound 17 Treatment on Inflammation

Figure 7:
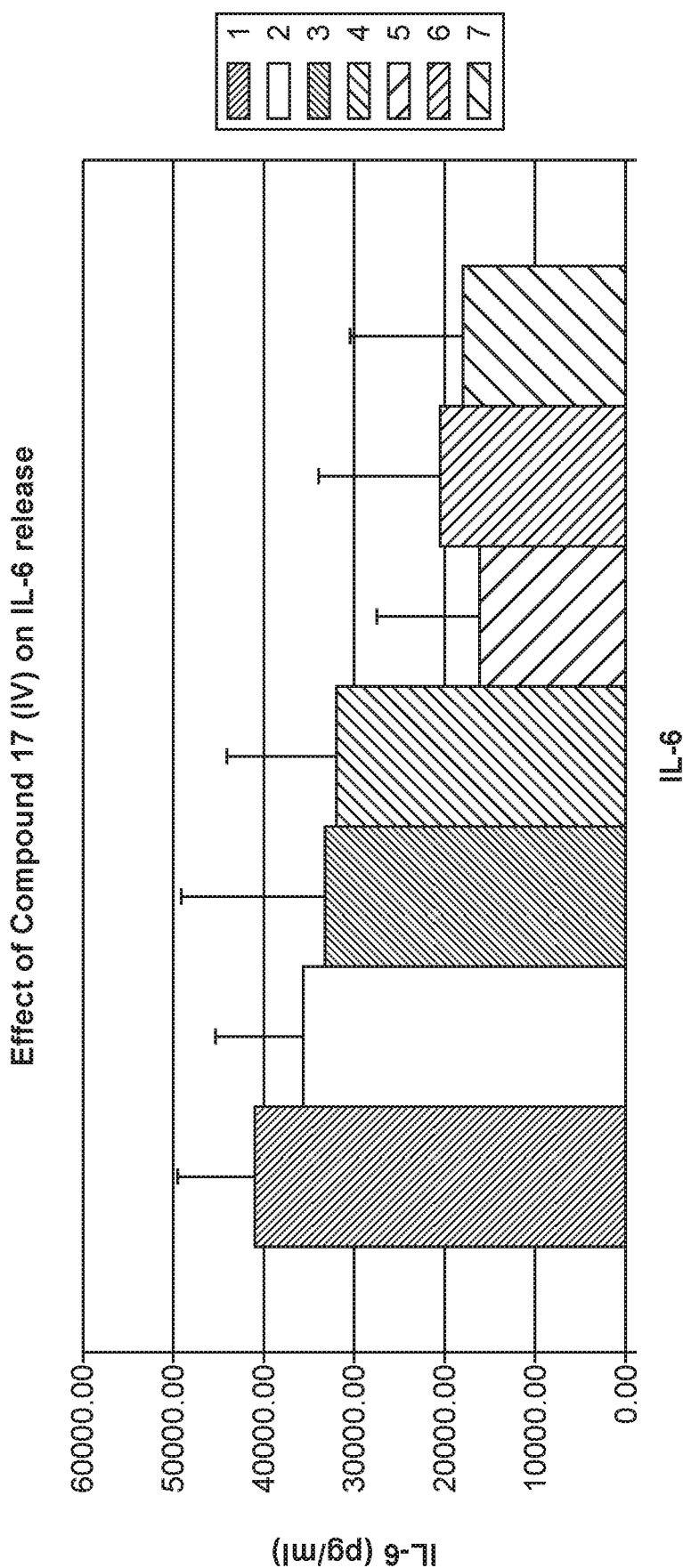
FIG. 7 illustrates the effect of Compound 17 on IL-6 release. The numbered bars refer to the Group numbers of Table 5 below.
Figure 11:
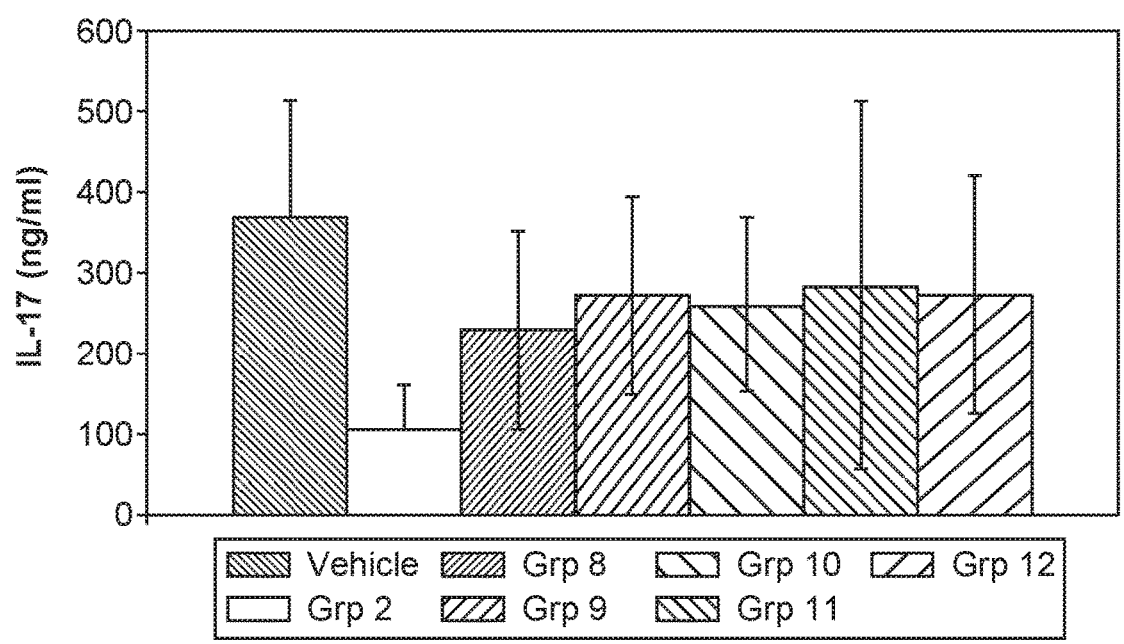
FIG. 11 illustrates the effect of pre-treatment on LPS-induced IL-17 release (i.v.). The numbered bars refer to the Group numbers of Table 6 below.
Figure 12:
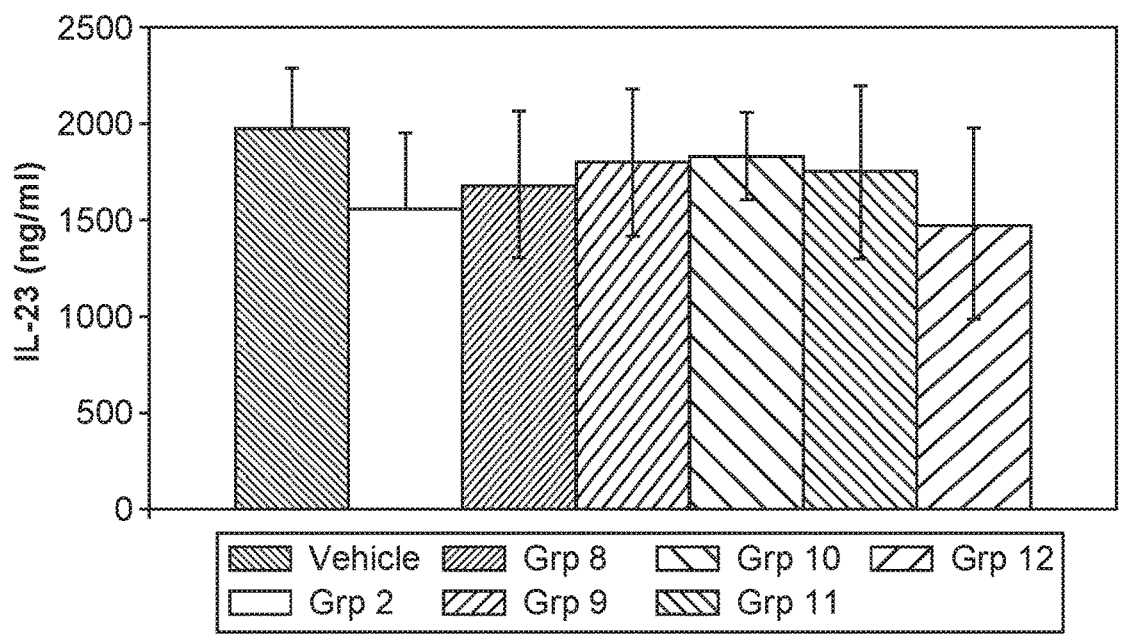
FIG. 12 illustrates the effect of pre-treatment on LPS-induced IL-23 release (i.v.). The numbered bars refer to the Group numbers of Table 6 below.

This LPS/cytokine assay was carried out in healthy mice and measured the level of cytokine IL-6, IL-17, and 23 induction by LPS. Compounds are dosed (either orally ("p.o.") or intravenously ("i.v.") at varying times before and after LPS, and the cytokines are measured at varying times after LPS. The effect of the tested compounds (Table 5) on IL-6 release is shown in FIG. 7. The effect of the tested compounds (Table 6) on IL-17 an IL-23 release is shown in FIG. 11 and FIG. 12, respectively.

TABLE 5

| Group Number | Material | Drug Route | Delivery (mg/kg) | Dose Drug Hours prior LPS | Harvest Hours after LPS |
|---|---|---|---|---|---|
| 1 | Vehicle | p.o. | n/a | 12 | 6 |
| 2 | Dex | p.o. | 1.0 | 12 | 6 |
| 3 | Compound 17 | i.v. | 0.03 | 12 | 6 |
| 4 | Compound 17 | i.v. | 0.10 | 12 | 6 |
| 5 | Compound 17 | i.v. | 0.3 | 12 | 6 |
| 6 | Compound 17 | i.v. | 1.0 | 12 | 6 |
| 7 | Compound 17 | i.v. | 10.0 | 12 | 6 |
| 8 | Compound 17 | p.o. | 0.03 | 12 | 6 |
| 9 | Compound 17 | p.o. | 0.10 | 12 | 6 |
| 10 | Compound 17 | p.o. | 0.3 | 12 | 6 |
| 11 | Compound 17 | p.o. | 1.0 | 12 | 6 |
| 12 | Compound 17 | p.o. | 10.0 | 12 | 6 | n/a = not applicable.
Dex = dexamethasone.

TABLE 6

| Group Number | Material | Drug Route | Delivery (mg/kg) | Dose Drug Hours prior LPS | Harvest Hours after LPS |
|---|---|---|---|---|---|
| 1 | Vehicle | p.o. | n/a | 12 | 6 |
| 2 | Dex | p.o. | 1 | 12 | 6 |
| 3 | Compound 17 | p.o. | 1 | 12 | 6 |
| 4 | Compound 17 | p.o. | 3 | 12 | 6 |
| 5 | Compound 17 | p.o. | 10 | 12 | 6 |
| 6 | Compound 17 | p.o. | 30 | 12 | 6 |

TABLE 6-continued

| Group Number | Material | Drug Route | Delivery (mg/kg) | Dose Drug Hours prior LPS | Harvest Hours after LPS |
|---|---|---|---|---|---|
| 7 | Compound 17 | p.o. | 60 | 12 | 6 |
| 8 | Compound 17 | i.v. | 1 | 12 | 6 |
| 9 | Compound 17 | i.v. | 3 | 12 | 6 |
| 10 | Compound 17 | i.v. | 10 | 12 | 6 |
| 11 | Compound 17 | i.v. | 30 | 12 | 6 |
| 12 | Compound 17 | i.v. | 60 | 12 | 6 | n/a = not applicable.
Dex = dexamethasone.

Example 10: Effect of Compound 17 Treatment on Rheumatoid Arthritis

Figure 13:
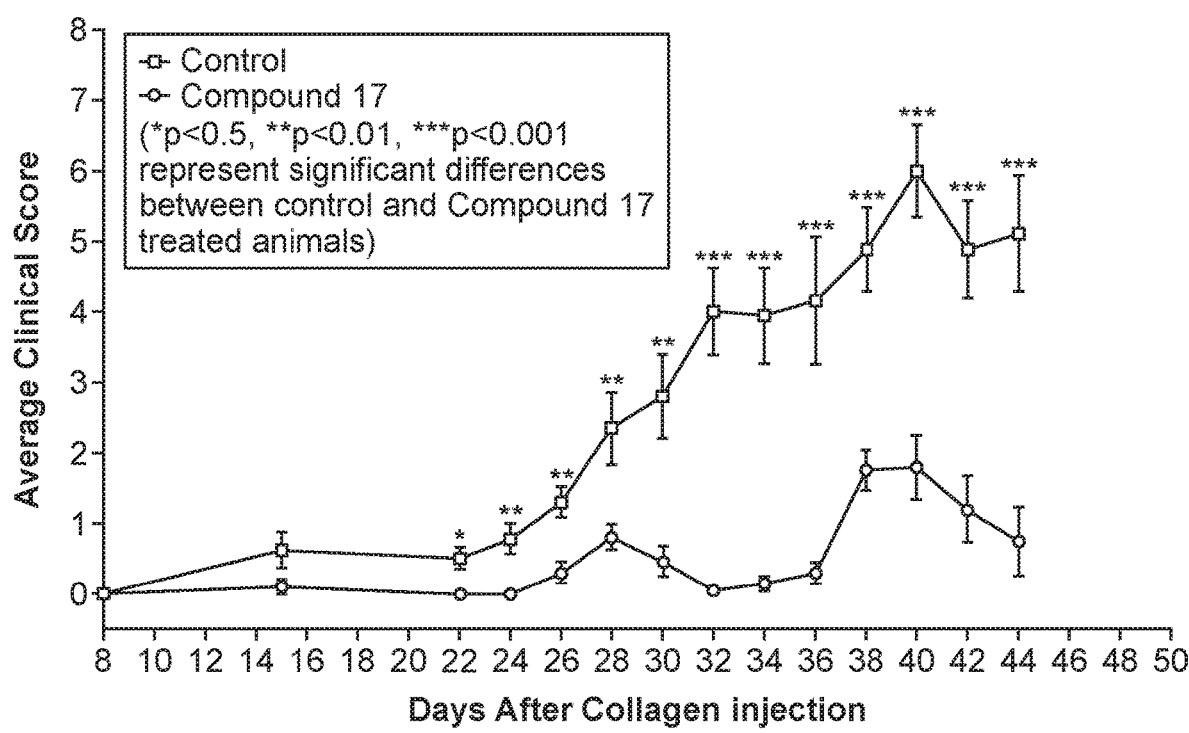
FIG. 13 illustrates the effect of Compound 17, as compared to control, on arthritis in a mouse model.

Compound 17 was tested in a collagen induced arthritis model in DBAJ1 mice. Compound 17 was started on day 8 when the arthritis was established, as in a therapeutic model, and the DBAJ1 mice were then treated daily with Compound 17 (15 mg/kg). Mice were challenged with bovine collagen II+complete adjuvant at day 0. Clinical scores were determined as follows: 0=normal; 0.5=erythema and edema in only one digit; 1=erythema and mild edema of the footpad, or ankle or two to five digits; 2=erythema and moderate edema of two joints (footpad, ankle, two to five digits); 3=erythema and severe edema of the entire paw; 4=reduced swelling and deformation leading to an incapacitated limb. The data is shown in FIG. 13 (10 mice per group, mean±SD), which demonstrates that Compound 17 inhibits arthritis in a mouse model.

Figure 14:
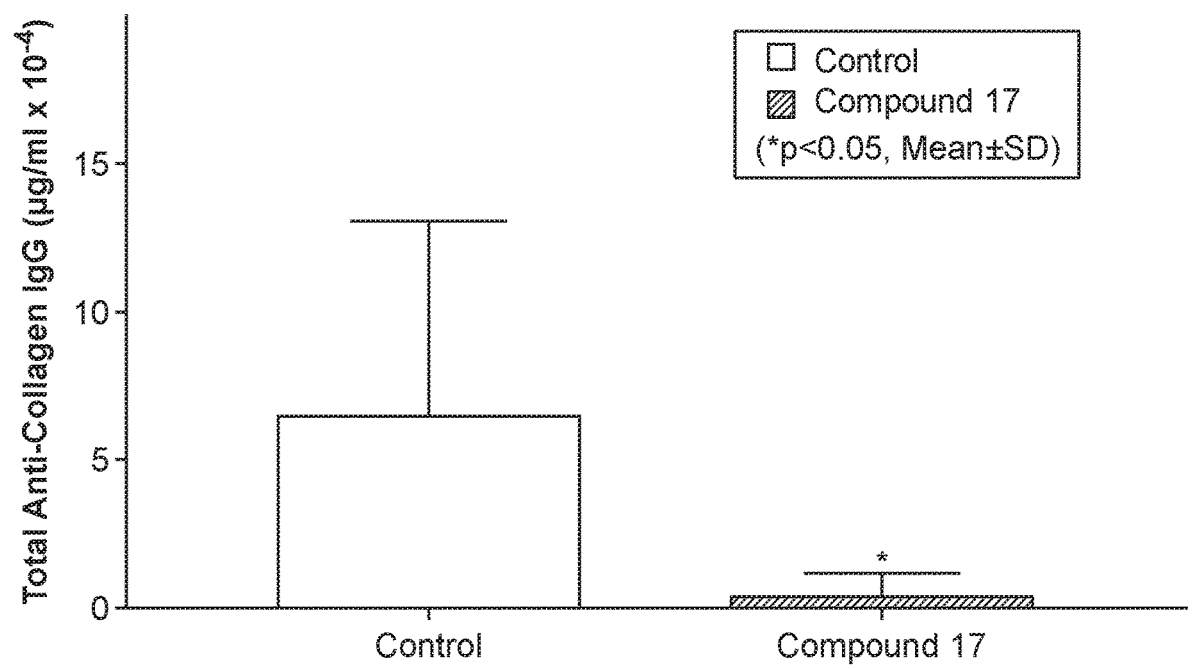
FIG. 14 illustrates the effect of Compound 17, as compared to control, on the production of anti-collagen antibodies in a mouse model of collagen-induced arthritis.

Measurement of anti-collagen antibodies in the collagen induced arthritis model of rheumatoid arthritis in DBAJ1 Mice was by an anti-collagen ELISA kit by standard methods. The data shown in FIG. 14 demonstrates that Compound 17 inhibits production of anti-collagen antibodies in a mouse model of collagen-induced arthritis.

While some embodiments have been illustrated and described, a person with ordinary skill in the art, after reading the foregoing specification, can effect changes, substitutions of equivalents and other types of alterations to the compounds of this disclosure or salts, pharmaceutical compositions, derivatives, prodrugs, metabolites, tautomers or racemic mixtures thereof as set forth herein. Each aspect and embodiment described above can also have included or incorporated therewith such variations or aspects as disclosed in regard to any or all of the other aspects and embodiments.

This disclosure is also not to be limited in terms of the particular aspects described herein, which are intended as single illustrations of individual aspects of this disclosure. Many modifications and variations of this disclosure can be made without departing from its spirit and scope, as will be apparent to those skilled in the art. Functionally equivalent methods within the scope of this disclosure, in addition to those enumerated herein, will be apparent to those skilled in the art from the foregoing descriptions. Such modifications and variations are intended to fall within the scope of the appended claims. It is to be understood that this disclosure is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of this disclosure indicated only by the appended claims, definitions therein and any equivalents thereof.

The embodiments, illustratively described herein, may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of this disclosure. This includes the generic description of this disclosure with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims, along with the full scope of equivalents to which such claims are entitled.

We claim:

1. A compound of Formula V:

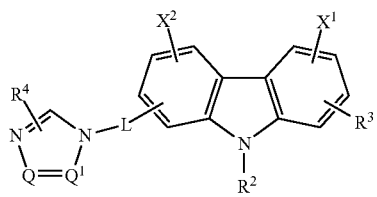

or a tautomer or a pharmaceutically acceptable salt thereof, wherein:
  $X^1$ and $X^2$ are the same and selected from H, F, and $CF_3$;
  $R^2$ is substituted alkyl, substituted aryl, or acyl;
  $R^3$ is selected from the group consisting of carboxyl, carboxyl ester, -arylene-carboxyl, -arylene-carboxyl ester, -oxyalkylene-carboxyl, -oxyalkylene-carboxyl ester, -alkylene-carboxyl, -alkylene-carboxyl ester, -alkenylene-carboxyl, -alkenylene-carboxyl ester, tetrazole, and heteroaryl substituted with 1 to 3 substituents selected from the group consisting of alkyl, substituted alkyl, alkoxy, substituted alkoxy, acyl, acylamino, amino, substituted amino, aryl, substituted aryl, aryloxy, substituted aryloxy, carboxyl, carboxyl ester, cyano, cycloalkyl, substituted cycloalkyl, cycloalkyloxy, substituted cycloalkyloxy, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, and nitro;
  $R^4$ is H, $C_1$-$C_4$ alkyl, or $CF_3$;
  L is a bond or

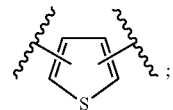;

Q is CH or N; and
  $Q^1$ is CH or N;
  provided that Q and $Q^1$ are not both N.

2. The compound of claim 1, wherein $R^2$ is substituted alkyl.

3. The compound of claim 1, wherein $R^2$ is

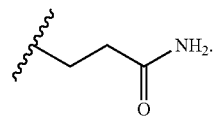

4. The compound of claim 1, wherein $R^2$ is substituted aryl.

5. Compound of claim 1, wherein $R^2$ is

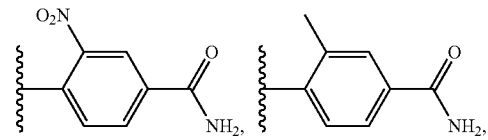

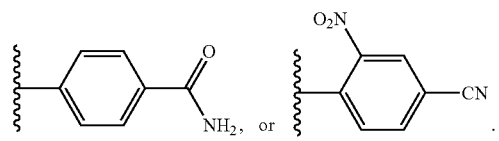

6. The compound of claim 1, wherein $R^2$ is acyl.

7. The compound of claim 1, wherein $R^2$ is alkyl substituted with cyano.

8. The compound of claim 1, wherein $R^3$ is carboxyl or $C_1$-$C_6$ alkylene-carboxyl.

9. The compound of claim 1, wherein Q is CH and $Q^1$ is CH.

10. The compound of claim 1, wherein L is a bond.

11. A compound selected from:

| Compound | Structure |
|---|---|
| 2 | ![structure] |

-continued

| Compound | Structure |
|---|---|
| 3 | (structure: 7-methoxy-9-(4-carbamoylphenyl)-9H-carbazole-2-carboxylic acid) |
| 4 | (structure: 7-[5-(2-methylimidazol-1-yl)thiophen-2-yl]-9H-carbazole-2-carboxylic acid) |
| 5 | (structure: 7-[5-(2-methylimidazol-1-yl)thiophen-2-yl]-9-(2-carbamoylethyl)-9H-carbazole-2-carboxylic acid) |
| 6 | (structure: 7-[5-(2-methylimidazol-1-yl)thiophen-2-yl]-9-(4-carbamoyl-2-methylphenyl)-9H-carbazole-2-carboxylic acid) |
| 7 | (structure: 7-(imidazol-1-ylmethyl)-9H-carbazole-2-carboxylic acid) |
| 8 | (structure: 7-(imidazol-1-ylmethyl)-9-(2-carbamoylethyl)-9H-carbazole-2-carboxylic acid) |

-continued
| Compound | Structure |
|---|---|
| 9 | 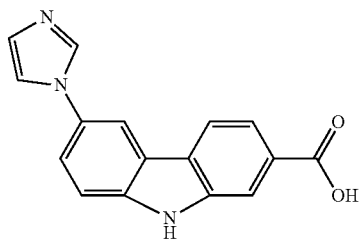 [SMILES: O=C(O)c1ccc2c(c1)[nH]c1ccc(-n3ccnc3)cc12] |
| 10 | 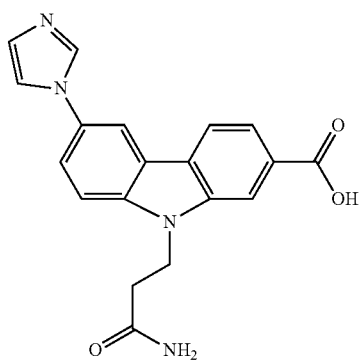 [SMILES: NC(=O)CCn1c2ccc(-n3ccnc3)cc2c2ccc(C(=O)O)cc21] |
| 11 | 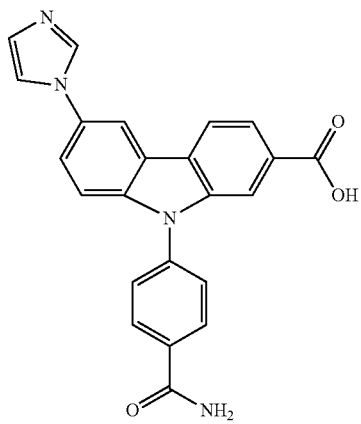 [SMILES: NC(=O)c1ccc(-n2c3ccc(-n4ccnc4)cc3c3ccc(C(=O)O)cc32)cc1] |
| 12 | 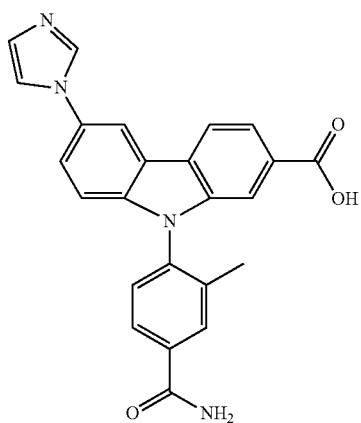 [SMILES: Cc1cc(C(N)=O)ccc1-n1c2ccc(-n3ccnc3)cc2c2ccc(C(=O)O)cc21] |

-continued

| Compound | Structure |
|---|---|
| 13 | 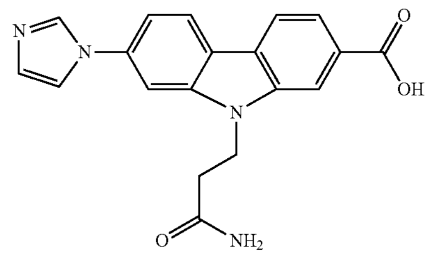 [SMILES: NC(=O)CCn1c2cc(C(=O)O)ccc2c2ccc(-n3ccnc3)cc21] |
| 14 | 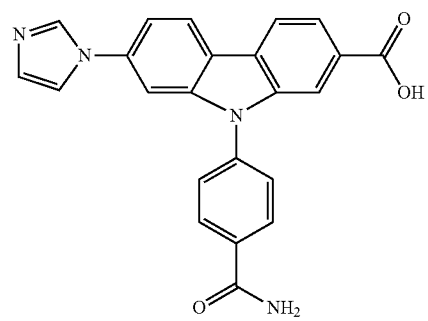 [SMILES: NC(=O)c1ccc(-n2c3cc(C(=O)O)ccc3c3ccc(-n4ccnc4)cc32)cc1] |
| 15 | 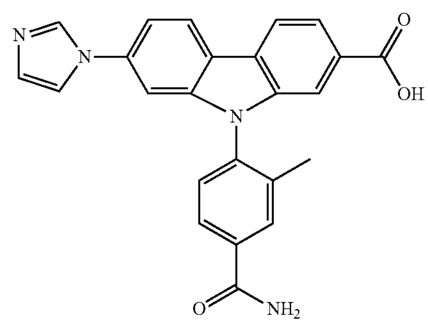 [SMILES: Cc1cc(C(N)=O)ccc1-n1c2cc(C(=O)O)ccc2c2ccc(-n3ccnc3)cc21] |
| 16 | 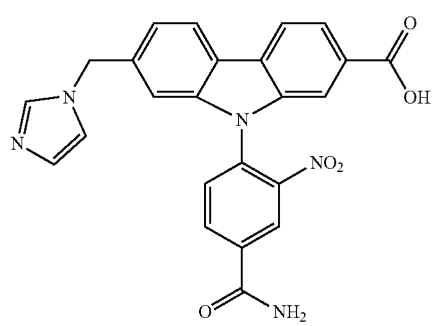 [SMILES: NC(=O)c1ccc(-n2c3cc(Cn4ccnc4)ccc3c3ccc(C(=O)O)cc32)c([N+](=O)[O-])c1] |
| 17 | 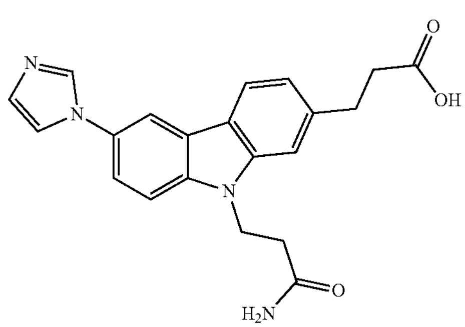 [SMILES: NC(=O)CCn1c2ccc(-n3ccnc3)cc2c2ccc(CCC(=O)O)cc21] |

-continued
| Compound | Structure |
|---|---|
| 18 | 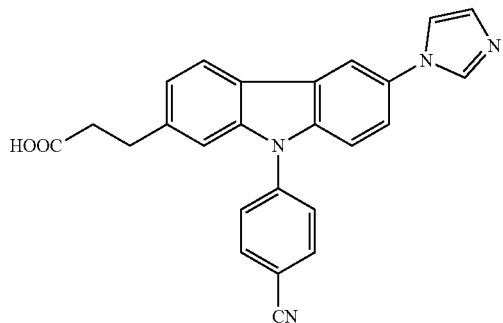 [SMILES: N#Cc1ccc(-n2c3ccc(-n4ccnc4)cc3c3ccc(CCC(=O)O)cc32)cc1] |
| 19 | 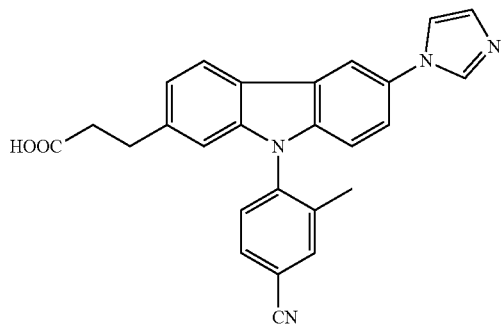 [SMILES: Cc1cc(C#N)ccc1-n1c2ccc(-n3ccnc3)cc2c2ccc(CCC(=O)O)cc21] |
| 20 | 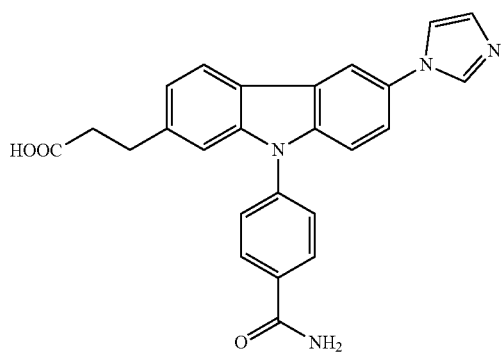 [SMILES: NC(=O)c1ccc(-n2c3ccc(-n4ccnc4)cc3c3ccc(CCC(=O)O)cc32)cc1] |
| 21 | 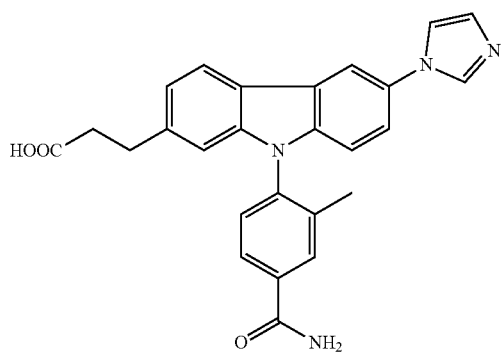 [SMILES: Cc1cc(C(N)=O)ccc1-n1c2ccc(-n3ccnc3)cc2c2ccc(CCC(=O)O)cc21] |

-continued

| Compound | Structure |
|---|---|
| 22 | 9-(4-chlorophenyl)-3-(1H-imidazol-1-yl)-7-carbazolepropanoic acid derivative |
| 23 | 9-(4-hydroxyphenyl)-3-(1H-imidazol-1-yl)-7-carbazolepropanoic acid derivative |
| 24 | 9-(4-methoxyphenyl)-3-(1H-imidazol-1-yl)-7-carbazolepropanoic acid derivative |
| 25 | 9-(2-methyl-4-methoxyphenyl)-3-(1H-imidazol-1-yl)-7-carbazolepropanoic acid derivative |
| 26 | 9-(2-cyanoethyl)-3-(1H-imidazol-1-yl)-7-carbazolepropanoic acid derivative |

-continued
| Compound | Structure |
|---|---|
| 27 | 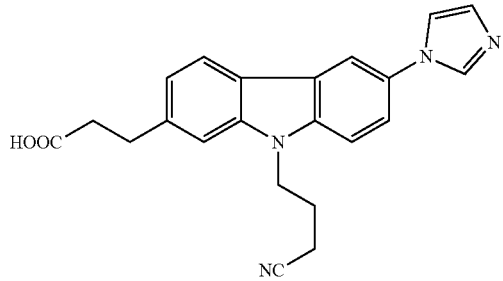 [SMILES: N#CCCCn1c2ccc(-n3ccnc3)cc2c2ccc(CCC(=O)O)cc21] |
| 28 | 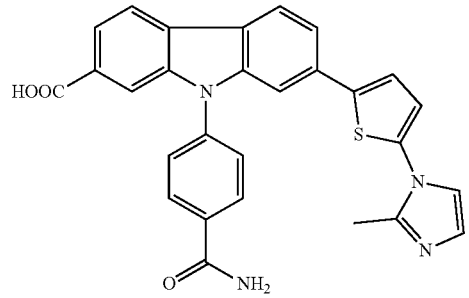 [SMILES: Cc1nccn1-c1ccc(-c2ccc3c4ccc(C(=O)O)cc4n(-c4ccc(C(N)=O)cc4)c3c2)s1] |
| 29 | 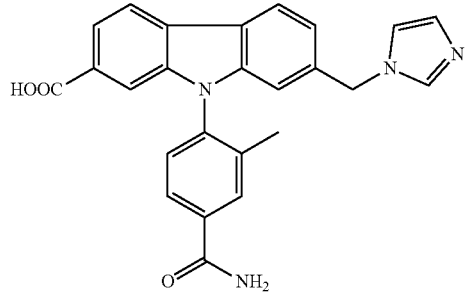 [SMILES: Cc1cc(C(N)=O)ccc1-n1c2cc(Cn3ccnc3)ccc2c2ccc(C(=O)O)cc21] |
| 30 | 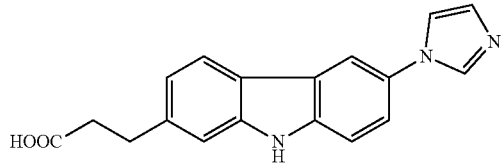 [SMILES: O=C(O)CCc1ccc2c(c1)[nH]c1ccc(-n3ccnc3)cc12] |
| 31 | 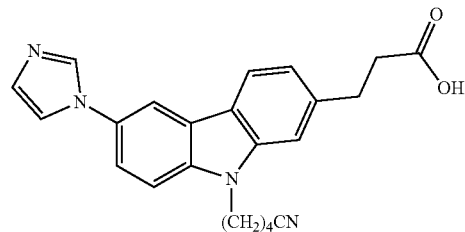 |
| 32 | 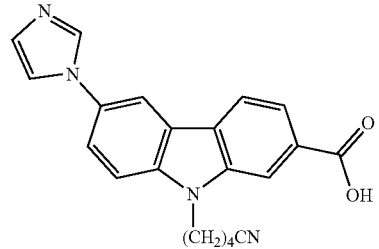 |

US 11,655,244 B2
109                                                                                     110
-continued
| Compound | Structure |
|---|---|
| 33 | 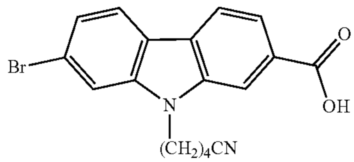 |
| 34 | 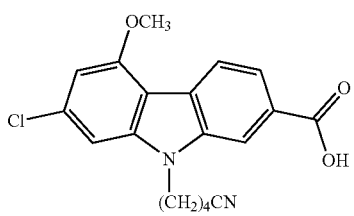 |
| 35 | 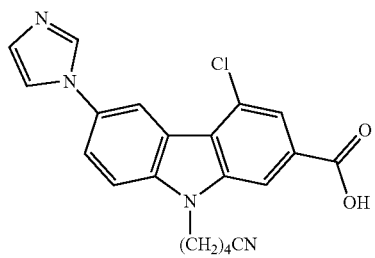 |
| 36 | 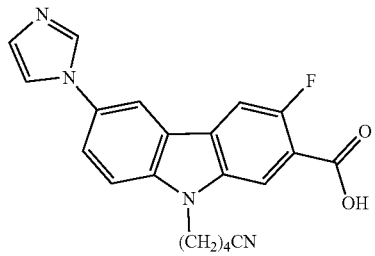 |
| 37 | 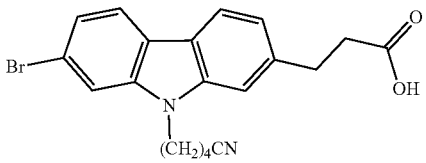 |
| 38 | 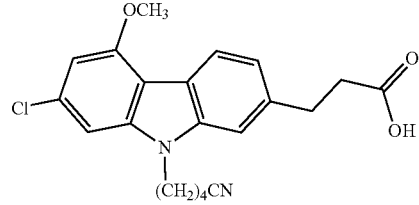 |
| 39 | 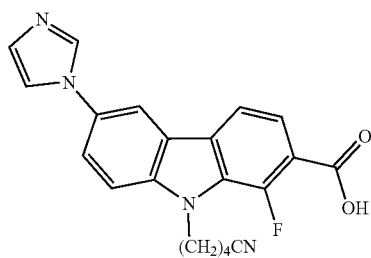 |

-continued

| Compound | Structure |
|---|---|
| 40 | 6-(1H-imidazol-1-yl)-9-(4-cyanobutyl)-carbazol-2-yl acrylic acid |
| 41 | 6-bromo-9-(4-cyanobutyl)-carbazol-2-yl acrylic acid |
| 42 | 5-methoxy-6-chloro-9-(4-cyanobutyl)-carbazol-2-yl acrylic acid |
| 43 | 6-(1H-imidazol-1-yl)-9-(4-cyanobutyl)-2-(1H-tetrazol-5-yl)-carbazole |
| 44 | 5-methoxy-6-chloro-9-(4-cyanobutyl)-2-(1H-tetrazol-5-yl)-carbazole |
| 45 | 6-bromo-9-(4-cyanobutyl)-2-(1H-tetrazol-5-yl)-carbazole |
| 46 | 6-(1H-imidazol-1-yl)-9-(4-cyanobutyl)-carbazol-2-yloxy acetic acid |

-continued

| Compound | Structure |
|---|---|
| 47 | 7-bromo-9-(4-cyanobutyl)-carbazol-2-yloxy acetic acid |
| 48 | 7-chloro-9-(4-cyanobutyl)-8-methoxy-carbazol-2-yloxy acetic acid |
| 49 | 2-(7-guanidino-9-propyl-carbazol-2-yl)acetic acid |
| 50 | 2-(9-(3-amino-3-oxopropyl)-7-(2-hydroxypyridin-4-yl)-carbazol-2-yloxy)acetic acid |
| 51 | 2-(9-(4-cyanobutyl)-7-(6-hydroxypyridin-3-yl)-carbazol-2-yloxy)-2-methylpropanoic acid |
| 52 | 2-(9-(2-cyanoethyl)-7-(5-fluoro-6-hydroxypyridin-3-yl)-carbazol-2-yl)-2,2-difluoroacetic acid |
| 53 | 7-(2-amino-6-imino-1-hydroxy-1,6-dihydropyrimidin-4-yl)-9-propyl-carbazole-2-carboxylic acid |

-continued

| Compound | Structure |
|---|---|
| 54 | 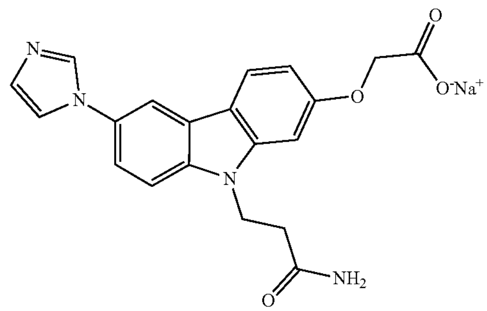 |
| C1 | 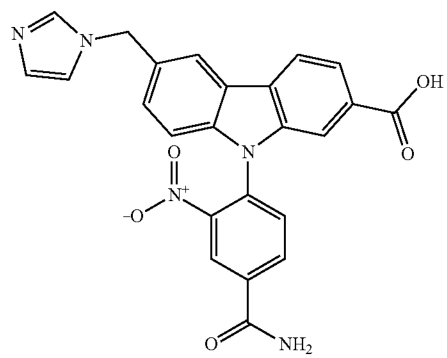 |
| D1 | 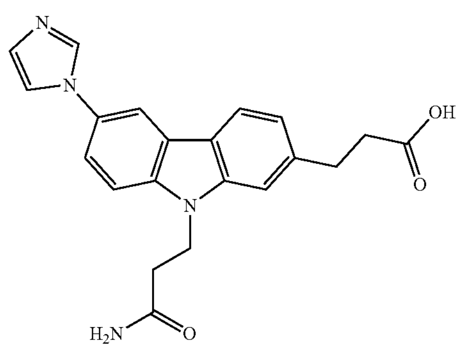 [SMILES: NC(=O)CCn1c2ccc(-n3ccnc3)cc2c2ccc(CCC(=O)O)cc21] |
| E1 | 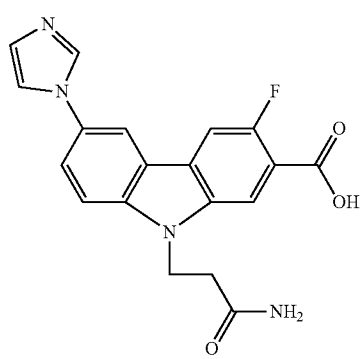 [SMILES: NC(=O)CCn1c2ccc(-n3ccnc3)cc2c2cc(F)c(C(=O)O)cc21] |
| F1 | 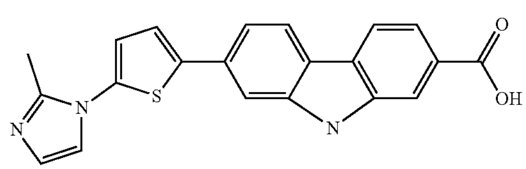 [SMILES: Cc1nccn1-c1ccc(-c2ccc3c(c2)[nH]c2cc(C(=O)O)ccc23)s1] |

-continued

| Compound | Structure |
|---|---|
| G1 | (carbazole with 2-carboxylic acid, 7-(thiazol-2-ylamino)methyl, N-(4-cyano-2-nitrophenyl)) |
| H1 | (carbazole with 2-carboxylic acid, 7-(oxazol-2-ylamino)methyl, N-(4-cyano-2-nitrophenyl)) |
| I1 | (carbazole with 2-carboxylic acid, 7-(oxazol-2-ylamino)methyl, N-(4-carbamoyl-2-nitrophenyl)) |
| J1 | (carbazole with 2-carboxylic acid, 7-(thiazol-2-ylamino)methyl, N-(4-carbamoyl-2-nitrophenyl)) |
| L1 | (7-methoxy-9-(3-amino-3-oxopropyl)-carbazole-2-carboxylic acid) |

-continued
| Compound | Structure |
|---|---|
| M1 | 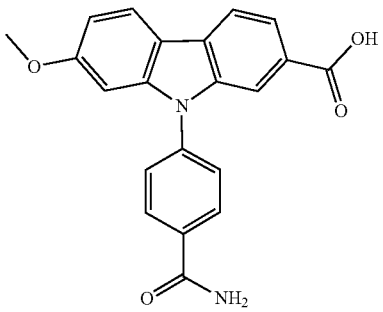 [SMILES: COc1ccc2c3ccc(C(=O)O)cc3n(-c3ccc(C(N)=O)cc3)c2c1] |
| N1 | 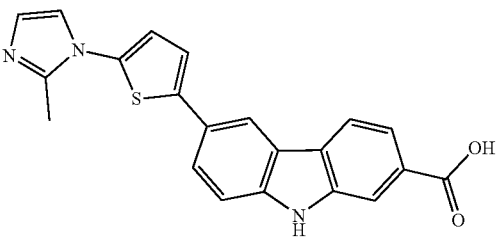 [SMILES: Cc1nccn1-c1ccc(-c2ccc3[nH]c4cc(C(=O)O)ccc4c3c2)s1] |
| O1 | 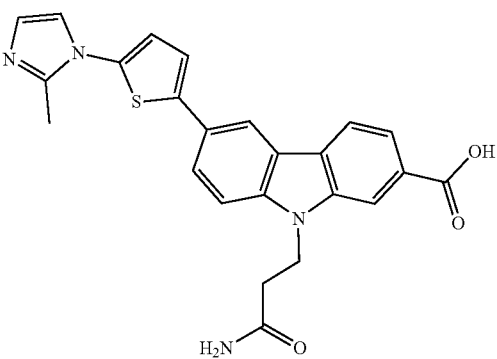 [SMILES: Cc1nccn1-c1ccc(-c2ccc3c(c2)c2ccc(C(=O)O)cc2n3CCC(N)=O)s1] |
| P1 | 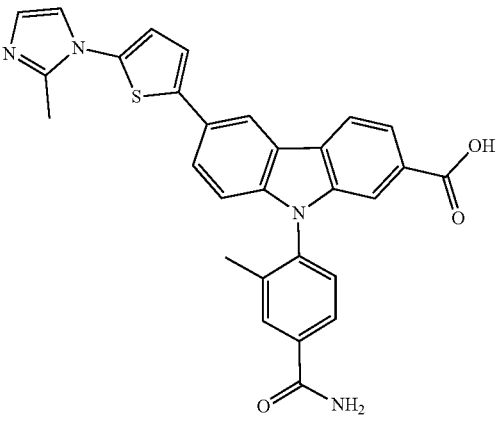 [SMILES: Cc1cc(C(N)=O)ccc1-n1c2ccc(-c3ccc(-n4ccnc4C)s3)cc2c2ccc(C(=O)O)cc21] |
| Q1 | 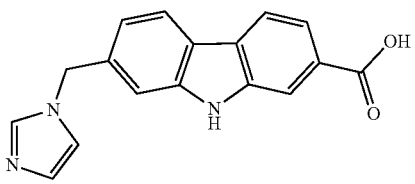 [SMILES: O=C(O)c1ccc2c(c1)[nH]c1cc(Cn3ccnc3)ccc12] |

-continued
| Compound | Structure |
|---|---|
| R1 | 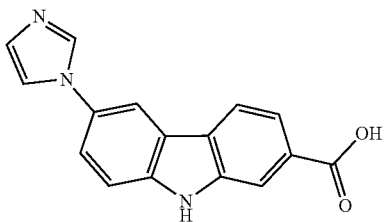 |
| S1 | 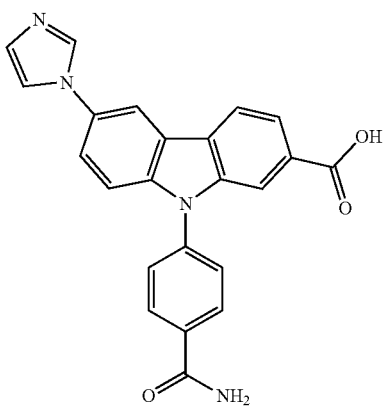 [SMILES: NC(=O)c1ccc(-n2c3ccc(-n4ccnc4)cc3c3ccc(C(=O)O)cc32)cc1] |
| T1 | 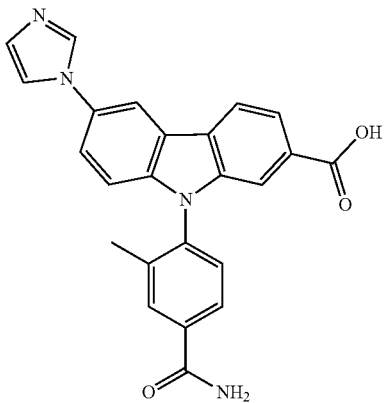 [SMILES: Cc1cc(C(N)=O)ccc1-n1c2ccc(-n3ccnc3)cc2c2ccc(C(=O)O)cc21] |
| U1 | 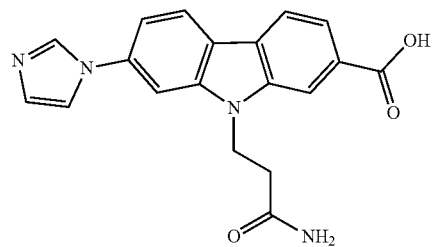 [SMILES: NC(=O)CCn1c2cc(C(=O)O)ccc2c2ccc(-n3ccnc3)cc21] |

-continued

| Compound | Structure |
|---|---|
| V1 | 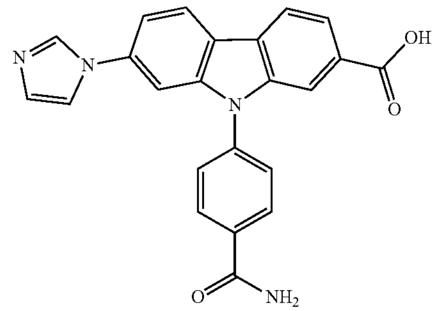 [SMILES: NC(=O)c1ccc(-n2c3cc(C(=O)O)ccc3c3ccc(-n4ccnc4)cc32)cc1] |
| W1 | 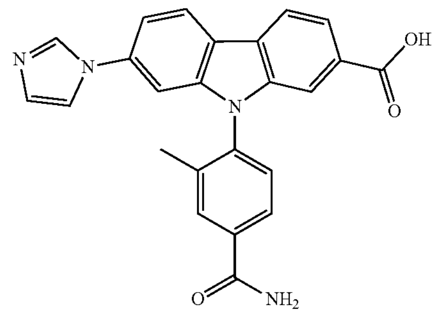 [SMILES: Cc1cc(C(N)=O)ccc1-n1c2cc(C(=O)O)ccc2c2ccc(-n3ccnc3)cc21] |
| A2 | 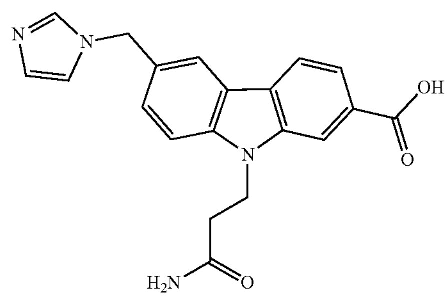 [SMILES: NC(=O)CCn1c2ccc(Cn3ccnc3)cc2c2ccc(C(=O)O)cc21] |
| F2 | 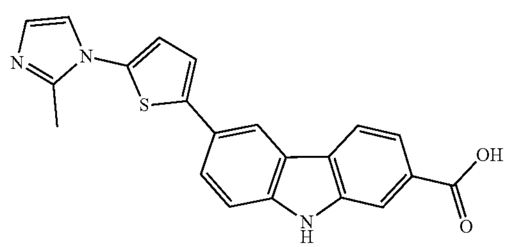 [SMILES: Cc1nccn1-c1ccc(-c2ccc3[nH]c4cc(C(=O)O)ccc4c3c2)s1] |
| G2 | 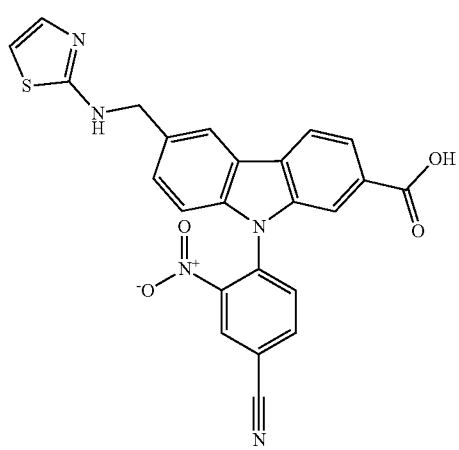 |

-continued

| Compound | Structure |
|---|---|
| H2 | 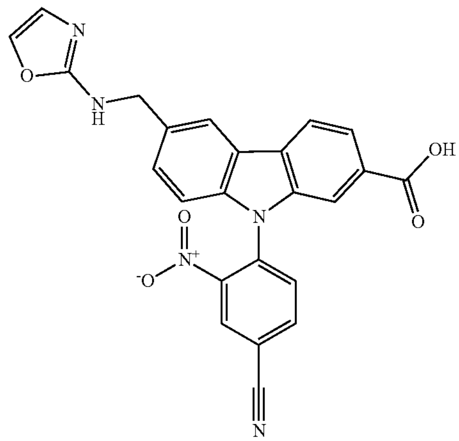 |
| I2 | 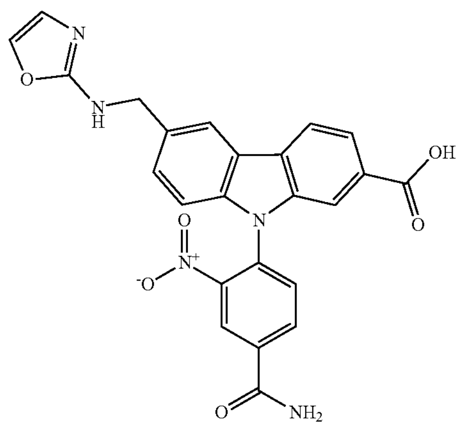 |
| J2 | | or a pharmaceutically acceptable salt thereof.

12. A pharmaceutical composition comprising a pharmaceutically acceptable excipient and one or more compounds of claim 1.

13. A method for inhibiting S-nitrosoglutathione reductase, the method comprising contacting cells with an effective amount of a compound of claim 1.

14. A method for inhibiting, arresting development of, ameliorating, or causing regression of a disease or disorder mediated at least in part by S-nitrosoglutathione reductase, the method comprising administering to a subject an effective amount of a compound of claim 1.

* * * * *